US012807676B2

(12) United States Patent
Li

(10) Patent No.: US 12,807,676 B2
(45) Date of Patent: Nov. 24, 2026

(54) MODIFIED CTLA4 AND METHODS OF USE THEREOF

(71) Applicant: Beijing VDJBio Co., Ltd., Beijing (CN)

(72) Inventor: Ziqiang Li, Beijing (CN)

(73) Assignee: BEIJING VDJBIO CO., LTD., Beijing (CN)

( * ) Notice: Subject to any disclaimer, the term of this patent is extended or adjusted under 35 U.S.C. 154(b) by 1599 days.

(21) Appl. No.: 17/222,881

(22) Filed: Apr. 5, 2021

(65) Prior Publication Data

US 2021/0340213 A1 Nov. 4, 2021

Related U.S. Application Data

(63) Continuation of application No. PCT/CN2019/114991, filed on Nov. 1, 2019, which is a continuation of application No. PCT/CN2018/113643, filed on Nov. 12, 2018.

(51) Int. Cl.
*A61K 38/00* (2006.01)
*C07K 14/705* (2006.01)

(52) U.S. Cl.
CPC ........ *C07K 14/70521* (2013.01); *A61K 38/00* (2013.01); *C07K 2319/30* (2013.01)

(58) Field of Classification Search
CPC .......... C07K 14/70521; C07K 2319/30; A61K 38/00
See application file for complete search history.

(56) References Cited

U.S. PATENT DOCUMENTS

| | | | | |
|---|---|---|---|---|
| 8,088,736 | B2 | 1/2012 | Franks et al. | |
| 8,642,557 | B2 * | 2/2014 | Akamatsu ............... | A61P 35/00 514/21.2 |
| 9,884,802 | B2 | 2/2018 | Gagnon et al. | |
| 11,753,458 | B2 * | 9/2023 | Evans ................ | C07K 14/7051 424/93.21 |
| 2003/0007968 | A1 | 1/2003 | Larsen et al. | |
| 2003/0138908 | A1 | 7/2003 | Koduri et al. | |
| 2011/0182898 | A1 | 7/2011 | Karrer et al. | |
| 2015/0051158 | A1 | 2/2015 | Akamatsu et al. | |
| 2016/0264643 | A1 | 9/2016 | Lazar et al. | |

FOREIGN PATENT DOCUMENTS

| | | | |
|---|---|---|---|
| CN | 105601741 | A | 5/2016 |
| CN | 106432473 | A | 2/2017 |
| CN | 106589132 | A | 4/2017 |
| EP | 0757099 | A2 | 2/1997 |
| EP | 3207938 | A2 | 8/2017 |
| JP | 2010506581 | A | 3/2010 |
| JP | 2013520176 | A | 6/2013 |
| JP | 2015523328 | A | 8/2015 |
| WO | WO-2005103081 | A2 | 11/2005 |
| WO | WO-2008047150 | A2 | 4/2008 |
| WO | WO-2011113019 | A2 | 9/2011 |
| WO | WO-2019074983 | A1 | 4/2019 |
| WO | WO-2020088645 | A1 | 5/2020 |

OTHER PUBLICATIONS

P16410 CTLA4_Human. UniProt. Accessed Dec. 1, 2025. https://www.uniprot.org/uniprotkb/P16410/variant-viewer (Year: 2025).*
Azhar, et al., "Recent advances in the development of novel protein scaffolds based therapeutics" International Journal of Biological Macromolecules 102 (2017) 630-641.
International Search Report and Written Opinion for corresponding Application No. PCT/CN2019/114991 issued Nov. 1, 2019.
"Larsen, et al., "Rational Development of LEA29Y (belatacept), a High-Affinity Variant of CTLA4-Ig with Potent Immunosuppressive Properties" American Journal of Transplantation;, 2005, p. 443-453".
EP19880624.2 Extended European Search Report dated Jun. 2, 2022.
PCT/CN2019/114991 International Search Report and Written Opinion dated Jan. 23, 2020.

* cited by examiner

*Primary Examiner* — Joanne Hama
(74) *Attorney, Agent, or Firm* — WILSON SONSINI GOODRICH & ROSATI

(57) ABSTRACT

In some aspects, the present disclosure provides polypeptides with high binding affinities for ligands, as well as compositions comprising the same, and methods of using the same. In some embodiments, polypeptides having high binding affinity for CD80, CD86, or both are provided.

21 Claims, 7 Drawing Sheets

Specification includes a Sequence Listing.

| | Abatacept | Belatacept | CA4-Fc-142# |
|---|---|---|---|
| IC50 | 164.7 | 3.074 | 0.4187 |

| | Abatacept | Belatacept | CA4-Fc-82# | CA4-Fc-142# |
|---|---|---|---|---|
| IC50 | 6.695 | 0.4519 | 0.3498 | 0.05593 |

| | Aabatacept | Belatacept | CA4-Fc-142# |
|---|---|---|---|
| IC50 | 1.030 | 0.04691 | 0.01226 |

| | Aabatacept | Belatacept | CA4-Fc-142# |
|---|---|---|---|
| IC50 | 1.835 | 0.1298 | 0.02483 |

SEQUENCE LISTING

<160> NUMBER OF SEQ ID NOS: 90

<210> SEQ ID NO 1
<211> LENGTH: 223
<212> TYPE: PRT
<213> ORGANISM: Homo sapiens

<400> SEQUENCE: 1

Met Ala Cys Leu Gly Phe Gln Arg His Lys Ala Gln Leu Asn Leu Ala
1 5 10 15

Thr Arg Thr Trp Pro Cys Thr Leu Leu Phe Phe Leu Leu Phe Ile Pro
20 25 30

Val Phe Cys Lys Ala Met His Val Ala Gln Pro Ala Val Val Leu Ala
35 40 45

Ser Ser Arg Gly Ile Ala Ser Phe Val Cys Glu Tyr Ala Ser Pro Gly
50 55 60

Lys Ala Thr Glu Val Arg Val Thr Val Leu Arg Gln Ala Asp Ser Gln
65 70 75 80

Val Thr Glu Val Cys Ala Ala Thr Tyr Met Met Gly Asn Glu Leu Thr
85 90 95

Phe Leu Asp Asp Ser Ile Cys Thr Gly Thr Ser Ser Gly Asn Gln Val
100 105 110

Asn Leu Thr Ile Gln Gly Leu Arg Ala Met Asp Thr Gly Leu Tyr Ile
115 120 125

Cys Lys Val Glu Leu Met Tyr Pro Pro Pro Tyr Tyr Leu Gly Ile Gly
130 135 140

Asn Gly Thr Gln Ile Tyr Val Ile Asp Pro Glu Pro Cys Pro Asp Ser
145 150 155 160

Asp Phe Leu Leu Trp Ile Leu Ala Ala Val Ser Ser Gly Leu Phe Phe
165 170 175

Tyr Ser Phe Leu Leu Thr Ala Val Ser Leu Ser Lys Met Leu Lys Lys
180 185 190

Arg Ser Pro Leu Thr Thr Gly Val Tyr Val Lys Met Pro Pro Thr Glu
195 200 205

Pro Glu Cys Glu Lys Gln Phe Gln Pro Tyr Phe Ile Pro Ile Asn
210 215 220

<210> SEQ ID NO 2
<211> LENGTH: 357
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu

-continued

```
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355


<210> SEQ ID NO 3
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80
```

```
Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355


<210> SEQ ID NO 4
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Trp Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80
```

```
Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355
```

<210> SEQ ID NO 5
<211> LENGTH: 357
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met His Val Ala Gln Pro Ala Val Val Leu Ala Ser Ser Arg Gly Ile
1               5                   10                  15

Ala Ser Phe Val Cys Glu Tyr Glu Ser Pro His Lys Ala Asn Glu Ile
            20                  25                  30

Arg Val Thr Val Leu Arg Gln Ala Asn Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
```

-continued

```
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355


<210> SEQ ID NO 6
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met His Val Ala Gln Pro Ala Val Val Leu Ala Ser Ser Arg Gly Ile
1               5                   10                  15

Ala Ser Phe Val Cys Glu Tyr Ala Ser Pro Asp Lys Ala Lys Ala Thr
            20                  25                  30

Glu Val Arg Val Thr Val Leu Arg Gln Thr Asp Ser Gln Val Thr Glu
        35                  40                  45

Val Cys Ala Ala Thr Tyr Met Met Gly Asn Glu Leu Thr Phe Leu Asp
    50                  55                  60
```

Asp Ser Ile Cys Thr Phe Thr Ser Ser Gly Asn Gln Val Asn Leu Thr
65 70 75 80

Ile Gln Gly Leu Arg Ala Met Asp Thr Gly Leu Tyr Ile Cys Met Val
85 90 95

Glu Leu Met Tyr Pro Pro Pro Tyr Tyr Leu Gly Ile Gly Asn Gly Thr
100 105 110

Gln Ile Tyr Val Ile Asp Pro Glu Pro Cys Pro Asp Ser Asp Gln Glu
115 120 125

Pro Lys Ser Ser Asp Lys Thr His Thr Ser Pro Pro Ser Pro Ala Pro
130 135 140

Glu Leu Leu Gly Gly Ser Ser Val Phe Leu Phe Pro Pro Lys Pro Lys
145 150 155 160

Asp Thr Leu Met Ile Ser Arg Thr Pro Glu Val Thr Cys Val Val Val
165 170 175

Asp Val Ser His Glu Asp Pro Glu Val Lys Phe Asn Trp Tyr Val Asp
180 185 190

Gly Val Glu Val His Asn Ala Lys Thr Lys Pro Arg Glu Glu Gln Tyr
195 200 205

Asn Ser Thr Tyr Arg Val Val Ser Val Leu Thr Val Leu His Gln Asp
210 215 220

Trp Leu Asn Gly Lys Glu Tyr Lys Cys Lys Val Ser Asn Lys Ala Leu
225 230 235 240

Pro Ala Pro Ile Glu Lys Thr Ile Ser Lys Ala Lys Gly Gln Pro Arg
245 250 255

Glu Pro Gln Val Tyr Thr Leu Pro Pro Ser Arg Asp Glu Leu Thr Lys
260 265 270

Asn Gln Val Ser Leu Thr Cys Leu Val Lys Gly Phe Tyr Pro Ser Asp
275 280 285

Ile Ala Val Glu Trp Glu Ser Asn Gly Gln Pro Glu Asn Asn Tyr Lys
290 295 300

Thr Thr Pro Pro Val Leu Asp Ser Asp Gly Ser Phe Phe Leu Tyr Ser
305 310 315 320

Lys Leu Thr Val Asp Lys Ser Arg Trp Gln Gln Gly Asn Val Phe Ser
325 330 335

Cys Ser Val Met His Glu Ala Leu His Asn His Tyr Thr Gln Lys Ser
340 345 350

Leu Ser Leu Ser Pro Gly Lys
355

<210> SEQ ID NO 7
<211> LENGTH: 227
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

```
His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 8
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
```

```
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 9
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225


<210> SEQ ID NO 10
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Lys Thr His Thr Cys Pro Pro Cys Pro Ala Pro Glu Leu Leu Gly
```

```
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 11
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ser Ser Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 12
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 13
```

<211> LENGTH: 227
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Gly Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Asp Glu Leu Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 14
<211> LENGTH: 226
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 15
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gln Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
```

```
        195                 200                 205

His Glu Ala Leu His Asn His Tyr Thr Gln Lys Ser Leu Ser Leu Ser
    210                 215                 220

Pro Gly Lys
225


<210> SEQ ID NO 16
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ser Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 17
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
```

```
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 18
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr His Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 19
<211> LENGTH: 233
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Asp Lys Arg Val Glu Ser Lys Tyr Gly Pro Pro Cys Pro Ser Cys Pro
1 5 10 15

Ala Pro Glu Phe Leu Gly Gly Pro Ser Val Phe Leu Phe Pro Pro Lys
20 25 30

Pro Lys Asp Thr Leu Met Ile Ser Arg Thr Pro Glu Val Thr Cys Val
35 40 45

Val Val Asp Val Ser Gln Glu Asp Pro Glu Val Gln Phe Asn Trp Tyr
50 55 60

Val Asp Gly Val Glu Val His Asn Ala Lys Thr Lys Pro Arg Glu Glu
65 70 75 80

Gln Phe Asn Ser Thr Tyr Arg Val Val Ser Val Leu Thr Val Leu His
85 90 95

Gln Asp Trp Leu Asn Gly Lys Glu Tyr Lys Cys Lys Val Ser Asn Lys
100 105 110

Gly Leu Pro Ser Ser Ile Glu Lys Thr Ile Ser Lys Ala Lys Gly Gln
115 120 125

Pro Arg Glu Pro Gln Val Tyr Thr Leu Pro Pro Ser Gln Glu Glu Met
130 135 140

Thr Lys Asn Gln Val Ser Leu Thr Cys Leu Val Lys Gly Phe Tyr Pro
145 150 155 160

Ser Asp Ile Ala Val Glu Trp Glu Ser Asn Gly Gln Pro Glu Asn Asn
165 170 175

Tyr Lys Thr Thr Pro Pro Val Leu Asp Ser Asp Gly Ser Phe Phe Leu
180 185 190

Tyr Ser Arg Leu Thr Val Asp Lys Ser Arg Trp Gln Glu Gly Asn Val
195 200 205

Phe Ser Cys Ser Val Met His Glu Ala Leu His Asn His Tyr Thr Gln
210 215 220

Lys Ser Leu Ser Leu Ser Leu Gly Lys
225 230

<210> SEQ ID NO 20
<211> LENGTH: 233
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 20

Asp Lys Arg Val Glu Ser Lys Tyr Gly Pro Pro Cys Pro Pro Cys Pro
1               5                   10                  15

Ala Pro Glu Phe Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230


<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ala Gly Gly Gly Gly Ser Gly
1               5


<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Pro Lys Ser Ser Asp
1               5
```

```
<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Ser Pro Lys Ala Gln Ala Ser Ser Val Pro Thr Ala Gln Pro Gln
1               5                   10                  15

Ala Glu Gly Leu Ala
            20


<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Leu Gln Leu Glu Glu Ser Ala Ala Glu Ala Gln Asp Gly Glu Leu
1               5                   10                  15

Asp


<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gln Pro Asp Glu Pro Gly Gly Ser
1               5


<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Ser Gly Ser Gly Ser Gly Ser Gly Ser Gly Ser
1               5                   10


<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Leu Gln Leu Glu Glu Ser Ala Ala Glu Ala Gln Glu Gly Glu Leu
1               5                   10                  15

Glu


<210> SEQ ID NO 28
```

<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Gly Ser Gly Ser Gly
1 5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Gly Ser Gly Cys
1

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Ala Gly Gly Gly Gly Ser Gly
1 5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Gly Ser Gly Ser
1

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gln Pro Asp Glu Pro Gly Gly Ser
1 5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Gly Ser Gly Ser Gly Ser
1 5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Thr Val Ala Ala Pro Ser
1 5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Lys Ala Gly Gly Gly Gly Ser Gly
1 5

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Lys Gly Ser Gly Ser Gly Ser Gly Ser Gly Ser Gly Ser
1 5 10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Lys Gln Pro Asp Glu Pro Gly Gly Ser
1 5

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Lys Glu Leu Gln Leu Glu Glu Ser Ala Ala Glu Ala Gln Asp Gly Glu
1 5 10 15

Leu Asp

<210> SEQ ID NO 39
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 39

Lys Thr Val Ala Ala Pro Ser
1               5


<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Ala Gly Gly Gly Gly Ser Gly Gly
1               5


<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Gly Ser Gly Ser Gly Ser Gly Ser Gly Ser Gly Ser Gly
1               5                   10


<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Gln Pro Asp Glu Pro Gly Gly Ser Gly
1               5                   10


<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Glu Leu Gln Leu Glu Glu Ser Ala Ala Glu Ala Gln Asp Gly Glu
1               5                   10                  15

Leu Asp Gly


<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Lys Thr Val Ala Ala Pro Ser Gly Ala Gly Gly Gly Gly Ser Gly Gly
1               5                   10                  15


<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Gly Gly Gly Gly Ser Gly
1               5


<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ser Gly Ser Gly Ser Gly Ser Gly Ser Gly Ser Gly
1               5                   10


<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Pro Asp Glu Pro Gly Gly Ser Gly
1               5


<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Val Ala Ala Pro Ser Gly
1               5


<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Ser Gly Gly Gly Ser Gly Gly Gly Gly Gly Ser Gly
1               5                   10                  15

Gly Gly Ser Gly Gly Gly Gly Ser Gly Gly Gly Ser
            20                  25


<210> SEQ ID NO 50
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Ser Pro Glu Pro Pro Thr Pro Glu Pro Pro Ser Pro Glu Pro
1               5                   10                  15


<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Leu Gln Leu Glu Glu Ser Ala Ala Glu Ala Gln Glu Gly Glu Leu
1               5                   10                  15

Glu


<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Ser Gly Gly Gly Gly Ser Gly Gly Gly Ser Gly Gly Gly Gly Gly
1               5                   10                  15

Ser


<210> SEQ ID NO 53
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser
1


<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Gly Ser
1               5


<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 55

Glu Glu Glu Glu Asp Glu Glu Glu Glu Asp
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Pro Ser Pro Glu Pro Pro Thr Pro Glu Pro
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Gly Ser His His His His His His His His Gly Ser
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Gly Gly Gly Gly Ser Gly Gly Gly Gly Ser Gly Gly Gly Gly Ser
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Gly Gly Gly Gly Gly Ser Gly Gly Gly Ser Gly Gly Gly Gly Ser
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Gly Ser Gly Ser Gly Ser Gly Ser Gly Ser Gly Ser Gly Ser Gly Ser
1               5                   10                  15

<210> SEQ ID NO 61
<211> LENGTH: 18

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Pro Ser Thr Pro Pro Thr Pro Ser Pro Ser Thr Pro Pro Thr Pro Ser
1 5 10 15

Pro Ser

<210> SEQ ID NO 62
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Arg Gly Gly Glu Glu Lys Lys Lys Glu Lys Glu Lys Glu Glu Gln Glu
1 5 10 15

Glu Arg Glu Thr Lys Thr Pro
20

<210> SEQ ID NO 63
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 64
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Pro Ser Pro Glu Pro Pro Thr Pro Glu Pro Pro Ser Pro Glu Pro Pro
1 5 10 15

Thr Pro Glu Pro Pro Ser Pro Glu Pro Pro Thr Pro Glu Pro
20 25 30

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Pro Ser Thr Pro Pro Thr Pro Ser Pro Ser Thr Pro Pro Thr Pro Ser
1 5 10 15

Pro Ser Pro Ser Thr Pro Pro Thr Pro Ser Pro Ser Thr Pro Pro Thr

```
            20                  25                  30

Pro Ser Pro Ser
        35


<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Ser Pro Glu Pro
1               5


<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Ser Pro Glu Pro Pro Thr Pro Glu Pro Pro Ser Pro Glu Pro Pro
1               5                   10                  15

Thr Pro Glu Pro
            20


<210> SEQ ID NO 68
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Pro Ser Pro Glu Pro Pro Thr Pro Glu Pro Pro Ser Pro Glu Pro Pro
1               5                   10                  15

Thr Pro Glu Pro Pro Ser Pro Glu Pro Pro Thr Pro Glu Pro Pro Ser
            20                  25                  30

Pro Glu Pro Pro Thr Pro Glu Pro
        35                  40


<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Thr Pro Glu Pro Pro Ser Pro Glu Pro Pro Thr Pro Glu Pro Pro
1               5                   10                  15

Ser Pro Glu Pro
            20


<210> SEQ ID NO 70
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 70

```
Pro Ser Pro Glu Pro Gly Gly Gly Ser Pro Thr Pro Glu Pro
1               5                   10
```

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Pro Ser Pro Glu Pro Glu Glu Glu Asp Pro Thr Pro Glu Pro
1               5                   10
```

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Pro Ser Pro Glu Pro Pro Thr Pro Glu Pro Glu Glu Glu Asp Pro Ser
1               5                   10                  15

Pro Glu Pro Pro Thr Pro Glu Pro
            20
```

<210> SEQ ID NO 73
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Pro Thr Pro Glu Pro Pro Ser Pro Glu Pro Pro Thr Pro Glu Pro Glu
1               5                   10                  15

Glu Glu Asp Pro Ser Pro Glu Pro Pro Thr Pro Glu Pro Pro Ser Pro
            20                  25                  30

Glu Pro
```

<210> SEQ ID NO 74
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Pro Thr Pro Glu Pro Pro Ser Pro Glu Pro Pro Thr Pro Glu Pro Gly
1               5                   10                  15

Gly Gly Gly Ser Pro Ser Pro Glu Pro Pro Thr Pro Glu Pro Pro Ser
            20                  25                  30

Pro Glu Pro
        35
```

<210> SEQ ID NO 75
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Pro Ser Pro Glu Pro Thr Pro Glu Pro Ser Pro Glu Pro Pro Thr Pro
1 5 10 15

Glu Pro Ser Pro Glu Pro Thr Pro Glu Pro
20 25

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Gly Glu Thr Gly Ser
1 5

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Gly Gly Gly Gly Ser Gly Gly Gly Gly Ser
1 5 10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Gly Glu Thr Gly Ser Ser Gly Glu Gly Thr
1 5 10

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Gly Glu Thr Gly Ser Ser Gly Glu Gly Thr Gly Ser Thr Gly Ser
1 5 10 15

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Gly Gly Gly Gly Ser Gly Gly Gly Gly Ser Gly Gly Gly Gly Ser Gly
1 5 10 15

Gly Gly Gly Ser
20

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Gly Glu Thr Gly Ser Ser Gly Glu Gly Thr Gly Ser Thr Gly Ser Gly
1 5 10 15

Ala Gly Glu Ser Gly Thr Gly Glu Ser Gly Glu Gly Gly Ser
20 25 30

<210> SEQ ID NO 82
<211> LENGTH: 1
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gln
1

<210> SEQ ID NO 83
<211> LENGTH: 16
<212> TYPE: PRT
<213> ORGANISM: Homo sapiens

<400> SEQUENCE: 83

Asp Lys Thr His Thr Cys Pro Pro Cys Pro Ala Pro Glu Leu Leu Gly
1 5 10 15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Gly Ser Thr His Thr Cys Pro Pro Cys Pro Ala Pro Glu Leu Leu Gly
1 5 10 15

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Glu Pro Lys Ser Ser Asp Lys Thr His Thr Cys Pro Pro Cys Pro Ala
1 5 10 15

```
Pro Glu Leu Leu Gly Gly Pro Ser
            20


<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Pro Lys Ser Ser Asp Lys Thr His Thr Cys Pro Pro Cys Pro Ala
1               5                   10                  15

Pro Glu Leu Leu Gly Gly Ser Ser
            20


<210> SEQ ID NO 87
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Pro Lys Ser Ser Gly Ser Thr His Thr Cys Pro Pro Cys Pro Ala
1               5                   10                  15

Pro Glu Leu Leu Gly Gly Ser Ser
            20


<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Lys Thr His Thr Cys Pro Pro Cys Pro Ala Pro Glu Leu Leu Gly
1               5                   10                  15

Gly Pro Ser


<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Lys Thr His Thr Cys Pro Pro Cys Pro Ala Pro Glu Leu Leu Gly
1               5                   10                  15

Gly Ser Ser


<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

-continued

<400> SEQUENCE: 90

His His His His His His
1 5

MODIFIED CTLA4 AND METHODS OF USE THEREOF

CROSS-REFERENCE

This application is a continuation of International Patent Application No. PCT/CN2019/114991, filed Nov. 1, 2019, which claims priority to PCT Application No. PCT/CN2018/113643, filed on Nov. 2, 2018, each of which is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Jun. 8, 2021, is named 46198-702_301_SL.txt and is 67,008 bytes in size.

BACKGROUND OF THE DISCLOSURE

Immune system is host defense system that protects organism against diseases. Dysfunction of the immune system can result in a wide range of diseases, such as autoimmune diseases, inflammatory diseases and cancer. There remains great need for improved therapeutic compositions and methods that can help tuning the proper functions of immune system, thereby protecting human body against various diseases and conditions.

SUMMARY OF THE DISCLOSURE

Described herein, in certain embodiments, is a polypeptide comprising a first amino acid sequence with about or greater than 70%, 75%, 80%, 85%, 90%, 95%, 96%, 97%, 98%, 99%, or 99.5% sequence identity to amino acids 1-124 of SEQ ID NO: 2, wherein the polypeptide comprises a mutation at one or more positions selected from positions 18, 40, 68, 77, 86, 92, 107, 117, 118, and 122 with respect to SEQ ID NO: 2.

In some embodiments, the polypeptide exhibits enhanced binding affinity for CD80 and/or CD86 as compared to abatacept (SEQ ID NO: 2), as determined by surface plasmon resonance at 37° C. In some embodiments, the polypeptide comprises a mutation at position 68 with respect to SEQ ID NO: 2. In some embodiments, the polypeptide comprises a mutation at position 40 with respect to SEQ ID NO: 2. In some embodiments, the polypeptide further comprises a mutation at one or more positions selected from positions 16, 24, 25, 27, 28, 29, 33, 41, 42, 48, 49, 50, 51, 52, 53, 54, 58, 59, 60, 61, 63, 64, 65, 69, 70, 80, 85, 93, 94, 96, and 105 with respect to SEQ ID NO: 2. In some embodiments, the mutation comprises amino acid substitution or deletion.

Described herein, in certain embodiments, is a polypeptide comprising an amino acid sequence with about or greater than 70%, 75%, 80%, 85%, 90%, 95%, 96%, 97%, 98%, 99%, or 99.5% sequence identity to amino acids 1-124 of SEQ ID NO: 2, wherein the polypeptide comprises an amino acid substitution selected from the group consisting of: S18R, S18N, A24S, G27DKA, G27DK, G27K, G27R, G27W, G27Y, G27E, G27KK, A29T, A40T, A49P, A50T, G68F, G68K, G68W, G68Y, G68H, G68D, G68E, L77V, D86N, C92S, C92Y, K93V, K93W, K93P, K93C, K93F, K93R, V94L, G105S, G107D, P117S, E118K, D122H, and any combinations thereof, with respect to SEQ ID NO: 2.

In some embodiments, the polypeptide exhibits enhanced binding affinity for CD80 and/or CD86 as compared to abatacept (SEQ ID NO: 2), as determined by surface plasmon resonance at 37° C. In some embodiments, the polypeptide comprises amino acid substitution G27DKA with respect to SEQ ID NO: 2. In some embodiments, the polypeptide comprises amino acid substitution G68F with respect to SEQ ID NO: 2. In some embodiments, the polypeptide comprises amino acid substitution A40T with respect to SEQ ID NO: 2. In some embodiments, the polypeptide further comprises amino acid substitution K93M with respect to SEQ ID NO: 2. In some embodiments, the polypeptide further comprises amino acid substitution G27DK with respect to SEQ ID NO: 2. In some embodiments, the polypeptide further comprises amino acid substitution G27H with respect to SEQ ID NO: 2. In some embodiments, the polypeptide comprises amino acid substitution P117S with respect to SEQ ID NO: 2. In some embodiments, the polypeptide further comprises at least one amino acid substitution selected from the group consisting of: A24E, G27H, G27D, A29S, R33W, D41G, T51N, K93M, K93N, and G105D, with respect to SEQ ID NO: 2.

In some embodiments, the polypeptide comprises a combination of amino acid substitutions selected from the group consisting of: G27DKA/R33W, G27DKA/G68F, R33W/G68F, G27R/G68Y, G27H/G68F, G27DK/G68F, G27DK/G68D, G27DK/G68E, G27D/G68F, G27E/G68F, G27H/G68D, G27H/G68E, G27DKA/G68F, G27DK/G68F, G27DKA/G68F/D122H, G27H/G68F, G27DKA/G68F/A40T/D122H, G27DKA/G68F/A40T/P117S, G27DKA/G68F/L77V, G27DKA/G68F/C92S/K93M, G27DK/G68F/A49P/A50T, G27DK/G68F/A40T/D86N/G105S, G27KK/G68F, G27DKA/G68F/P117S, G27DKA/G68F/A49P/A50T, G27DK/G68F/A40T, G27DK/G68F/L77V/G105S/P117S, G27DK/G68F/L77V, G27DK/G68F/C92S/K93M, G27DK/G68F/P117S, G27DKA/G68F/G105S, G27DKA/G68F/D86N, G27DK/G68F/D122H, G27DK/G68F/A40T/G105S, G27DK/G68F/G105S, G27DK/G68F/D86N, G27DKA/G68F/A40T, G27DKA/G68F/K93M, G27DK/G68F/K93M, and G27DKA/A40T/G68F/K93M, with respect to SEQ ID NO: 2. In some embodiments, the polypeptide comprises a combination of amino acid substitutions G27DKA/A40T/G68F/K93M with respect to SEQ ID NO: 2. In some embodiments, the polypeptide comprises a combination of amino acid substitutions G27DKA/G68F/A40T with respect to SEQ ID NO: 2. In some embodiments, the polypeptide comprises a combination of amino acid substitutions G27DKA/G68F/K93M with respect to SEQ ID NO: 2. In some embodiments, the polypeptide comprises a combination of amino acid substitutions G27DKA/G68F/A40T/P117S with respect to SEQ ID NO: 2. In some embodiments, the polypeptide comprises a combination of amino acid substitutions G27DKA/G68F/P117S with respect to SEQ ID NO: 2. In some embodiments, the polypeptide comprises a combination of amino acid substitutions G27H/G68F with respect to SEQ ID NO: 2. In some embodiments, the polypeptide comprises a combination of amino acid substitutions G27DKA/G68F with respect to SEQ ID NO: 2. In some embodiments, the polypeptide comprises a combination of amino acid substitutions G27DK/G68F/K93M with respect to SEQ ID NO: 2. In some embodiments, the polypeptide comprises a combination of amino acid substitutions G27DK/G68F/A40T with respect to SEQ ID NO: 2. In some embodiments, the polypeptide comprises a combination of amino acid substitutions G27DK/G68F/L77V/G105S/P117S with respect to SEQ ID NO: 2. In some embodiments, the polypeptide comprises a combination of amino acid substitutions G27DK/G68F/L77V with respect to SEQ ID NO: 2. In some embodiments, the polypeptide comprises a combination of amino acid substitutions G27DK/G68F/P117S with respect to SEQ ID NO: 2. In some embodiments, the polypeptide comprises a combination of amino acid substitutions G27DK/G68F/D122H with respect to SEQ ID NO: 2.

In some embodiments, the polypeptide comprises at least 1, at least 2, at least 3, at least 4, at least 5, at least 6, at least 7, at least 8, at least 9, or at least 10 amino acid substitutions with respect to amino acids 1-124 of SEQ ID NO: 2. In some embodiments, the polypeptide comprises at most 1, at most 2, at most 3, at most 4, at most 5, at most 6, at most 7, at most 8, at most 9, or at most 10 amino acid substitutions with respect to amino acids 1-124 of SEQ ID NO: 2.

Described herein, in certain embodiments, is a polypeptide comprising an amino acid sequence with about or greater than 70%, 75%, 80%, 85%, 90%, 95%, 96%, 97%, 98%, 99%, or 99.5% sequence identity to amino acids 1-124 of SEQ ID NO: 2, wherein amino acid substitutions of the polypeptide with respect to amino acids 1-124 of SEQ ID NO: 2 are selected from the amino acid substitutions as described herein.

In some embodiments, the polypeptide further comprises a second amino acid sequence fused to the first amino acid sequence. In some embodiments, the second amino acid sequence codes for an IgG Fc region. In some embodiments, the IgG Fc region is from a human IgG molecule.

In some embodiments, the second amino acid sequence has about or greater than 70%, 75%, 80%, 85%, 90%, 95%, 96%, 97%, 98%, 99%, 99.5% or 100% sequence identity to amino acids 125-357 of SEQ ID NO: 2. In some embodiments, the polypeptide has about or greater than 70%, 75%, 80%, 85%, 90%, 95%, 96%, 97%, 98%, 99%, 99.5% or 100% sequence identity to amino acids 1-359 of SEQ ID NO: 6. In some embodiments, the first and second amino acid sequences are fused together via a linker. In some embodiments, the linker comprises 1 to 10 amino acids. In some embodiments, the linker comprises an amino acid sequence selected from Table 7. In some embodiments, the linker comprises an amino acid sequence Q (SEQ ID NO: 82) or GGGGS (SEQ ID NO: 54).

In some embodiments, the polypeptide exhibits a binding affinity for CD80 at least 1.5, at least 2, at least 3, at least 4, at least 5, at least 10, at least 15, at least 20, at least 25, at least 30, at least 40, at least 50, at least 100, at least 150, at least 200, at least 250, or at least 300 times greater than affinity of abatacept (SEQ ID NO: 2) for CD80, as determined by surface plasmon resonance at 37° C. In some embodiments, the polypeptide exhibits a binding affinity for CD86 at least 1.5, at least 2, at least 3, at least 4, at least 5, at least 10, at least 15, at least 20, at least 25, at least 30, at least 40, at least 50, at least 100, at least 150, at least 200, at least 250, or at least 300 times greater than affinity of abatacept (SEQ ID NO: 2) for CD86, as determined by surface plasmon resonance at 37° C. In some embodiments, the polypeptide exhibits a greater binding affinity for CD80 than affinity of belatacept (SEQ ID NO: 3) for CD80, as determined by surface plasmon resonance at 37° C. In some embodiments, the polypeptide exhibits a greater binding affinity for CD86 than affinity of belatacept (SEQ ID NO: 3) for CD86, as determined by surface plasmon resonance at 37° C. In some embodiments, the polypeptide exhibits a binding affinity for CD80 at least 1.5, at least 2, at least 3, at least 4, at least 5, at least 10, at least 15, at least 20, at least 25, or at least 30 times greater than affinity of belatacept (SEQ ID NO: 3) for CD80, as determined by surface plasmon resonance at 37° C. In some embodiments, the polypeptide exhibits a binding affinity for CD86 at least 1.5, at least 2, at least 3, at least 4, at least 5, at least 10, at least 15, at least 20, at least 25, or at least 30 times greater than affinity of belatacept (SEQ ID NO: 3) for CD86, as determined by surface plasmon resonance at 37° C. In some embodiments, the polypeptide exhibits a greater binding affinity for CD80 than affinity of SEQ ID NO: 4 for CD80, as determined by surface plasmon resonance at 37° C. In some embodiments, the polypeptide exhibits a greater binding affinity for CD86 than affinity of SEQ ID NO: 4 for CD86, as determined by surface plasmon resonance at 37° C. In some embodiments, the polypeptide exhibits a binding affinity for CD80 at least 1.5, at least 2, at least 3, at least 4, at least 5, at least 10, at least 15, at least 20, at least 25, or at least 30 times greater than affinity of SEQ ID NO: 4 for CD80, as determined by surface plasmon resonance at 37° C. In some embodiments, the polypeptide exhibits a binding affinity for CD86 at least 1.5, at least 2, at least 3, at least 4, at least 5, at least 10, at least 15, at least 20, at least 25, or at least 30 times greater than affinity of SEQ ID NO: 4 for CD86, as determined by surface plasmon resonance at 37° C. In some embodiments, the polypeptide exhibits a greater binding affinity for CD80 than affinity of SEQ ID NO: 5 for CD80, as determined by surface plasmon resonance at 37° C. In some embodiments, the polypeptide exhibits a greater binding affinity for CD86 than affinity of SEQ ID NO: 5 for CD86, as determined by surface plasmon resonance at 37° C. In some embodiments, the polypeptide exhibits a binding affinity for CD80 at least 1.5, at least 2, at least 3, at least 4, at least 5, at least 10, at least 15, at least 20, at least 25, or at least 30 times greater than affinity of SEQ ID NO: 4 for CD80, as determined by surface plasmon resonance at 37° C. In some embodiments, the polypeptide exhibits a binding affinity for CD86 at least 1.5, at least 2, at least 3, at least 4, at least 5, at least 10, at least 15, at least 20, at least 25, or at least 30 times greater than affinity of SEQ ID NO: 4 for CD86, as determined by surface plasmon resonance at 37° C.

Described herein, in certain embodiments, is a polypeptide-drug conjugate comprising the polypeptide as disclosed herein.

Described herein, in certain embodiments, is a method of treating a disease or condition comprising administering the polypeptide as disclosed herein or the polypeptide-drug conjugate as disclosed herein to a subject in need thereof.

In some embodiments, the disease or condition comprises infection, endotoxic shock associated with infection, arthritis, rheumatoid arthritis, psoriatic arthritis, systemic onset juvenile idiopathic arthritis (JIA), inflammatory bowel disease (IBD), systemic lupus erythematosus (SLE), asthma, pelvic inflammatory disease, Alzheimer's Disease, Crohn's disease, ulcerative colitis, irritable bowel syndrome, multiple sclerosis, ankylosing spondylitis, dermatomyositis, uveitis, Peyronie's Disease, coeliac disease, gallbladder disease, Pilonidal disease, peritonitis, psoriasis, vasculitis, surgical adhesions, stroke, Type I Diabetes, Lyme arthritis, meningoencephalitis, immune mediated inflammatory disorders of the central and peripheral nervous system, autoimmune disorders, pancreatitis, trauma from surgery, graft-versus-host disease, transplant rejection, heart disease, bone resorption, burns patients, myocardial infarction, Paget's disease, osteoporosis, sepsis, liver/lung fibrosis, periodontitis, hypochlorhydria, solid tumors (renal cell carcinoma), liver cancer, multiple myeloma, prostatic cancer, bladder cancer, pancreatic cancer, neurological cancers, and B-cell malignancies (e.g., Castleman's disease, certain lymphomas, chronic lymphocytic leukemia, and multiple myeloma).

Described herein, in certain embodiments, is a polypeptide for use in treating a condition of a subject.

In some embodiments, the condition comprises transplant rejection, infection, endotoxic shock associated with infection, arthritis, rheumatoid arthritis, psoriatic arthritis, systemic onset juvenile idiopathic arthritis (JIA), inflammatory bowel disease (IBD), systemic lupus erythematosus (SLE), asthma, pelvic inflammatory disease, Alzheimer's Disease, Crohn's disease, ulcerative colitis, irritable bowel syndrome, multiple sclerosis, ankylosing spondylitis, dermatomyositis, uveitis, Peyronie's Disease, coeliac disease, gallbladder disease, Pilonidal disease, peritonitis, psoriasis, vasculitis, surgical adhesions, stroke, Type I Diabetes, Lyme arthritis, meningoencephalitis, immune mediated inflammatory disorders of the central and peripheral nervous system, autoimmune disorders, pancreatitis, trauma from surgery, graft-versus-host disease, heart disease, bone resorption, burns patients, myocardial infarction, Paget's disease, osteoporosis, sepsis, liver/lung fibrosis, periodontitis, hypochlorhydria, solid tumors (renal cell carcinoma), liver cancer, multiple myeloma, prostatic cancer, bladder cancer, pancreatic cancer, neurological cancers, and B-cell malignancies (e.g., Castleman's disease, certain lymphomas, chronic lymphocytic leukemia, and multiple myeloma).

Described herein, in certain embodiments, is a pharmaceutical composition comprising the polypeptide as disclosed herein or the polypeptide-drug conjugate as disclosed herein and a pharmaceutically acceptable excipient.

Described herein, in certain embodiments, is a kit comprising the polypeptide as disclosed herein or the polypeptide-drug conjugate as disclosed herein in a container.

Described herein, in certain embodiments, is use of a polypeptide as provided herein or a polypeptide-drug conjugate as provided herein for the manufacture of a medicament for treating a condition of a subject.

Described herein, in certain embodiments, is an isolated polynucleotide encoding the polypeptide as disclosed herein.

Described herein, in certain embodiments, is a vector comprising the isolated polynucleotide as disclosed herein.

Described herein, in certain embodiments, is a cell comprising the vector as disclosed herein.

In some embodiments, the cell is a eukaryotic cell. In some embodiments, the cell is a prokaryotic cell. In some embodiments, the cell is a mammalian cell, bacterial cell, fungal cell, or an insect cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
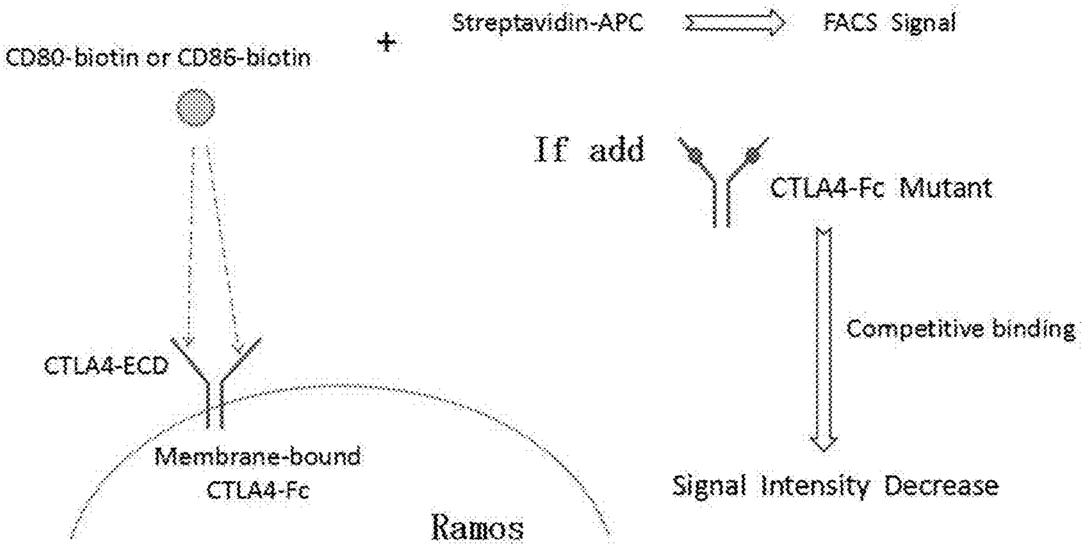
FIG. 1 is an illustration of a competitive binding assay for exemplary polypeptides (CTLA4-Fc mutants).

The systems and methods of this disclosure as described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Green, *Molecular Cloning: A Laboratory Manual,* 4th Edition (2012) (all from Cold Spring Harbor Laboratory Press); Stryer, L., *Biochemistry* (4th Ed.) W.H. Freeman, N.Y. (1995); Gait, "*Oligonucleotide Synthesis: A Practical Approach*" IRL Press, London (1984); Nelson and Cox, *Lehninger, Principles of Biochemistry,* 6th Ed., W.H. Freeman Pub., New York (2012); R. I. Freshney, *Culture of Animal Cells: A Manual of Basic Technique and Specialized Applications,* $6^{th}$ Ed., Wiley-Blackwell (2010); and Berg et al., *Biochemistry,* $5^{th}$ Ed., W.H. Freeman Pub., New York (2002), all of which are herein incorporated by reference in their entirety for all purposes. Before the present compositions, research tools and systems and methods are described, it is to be understood that this disclosure is not limited to the specific systems and methods, compositions, targets and uses described, as such may, of course, vary. It is also to be understood that the terminology used herein is for the purpose of describing particular aspects only and is not intended to limit the scope of the present disclosure, which will be limited only by appended claims.

As used in the specification and claims, the singular form "a," "an," and "the" include plural references unless the context clearly dictates otherwise. For example, the term "a cell" includes a plurality of cells, including mixtures thereof.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polypeptide," "oligopeptide," "peptide" and "protein" are used interchangeably herein to refer to polymers of amino acids of any length. The polymer may be linear or branched, it May comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides as described herein are based upon an antibody, the polypeptides can occur as single chains or associated chains.

The term "amino acid" refers to natural, unnatural, and synthetic amino acids, including but not limited to both the D or L optical isomers, and amino acid analogs and peptidomimetics. Standard single or three letter codes are used to designate amino acids.

The term "natural L-amino acid" means the L optical isomer forms of glycine (G), proline (P), alanine (A), valine (V), leucine (L), isoleucine (I), methionine (M), cysteine (C), phenylalanine (F), tyrosine (Y), tryptophan (W), histidine (H), lysine (K), arginine (R), glutamine (Q), asparagine (N), glutamic acid (E), aspartic acid (D), serine(S), and threonine (T).

The term "non-naturally occurring," as applied to sequences and as used herein, means polypeptide or polynucleotide sequences that do not have a counterpart to, are not complementary to, or do not have a high degree of homology with a wild-type or naturally-occurring sequence found in a mammal, or comprise non-naturally occurring residues (e.g. nucleotide analogues). For example, a non-naturally occurring polypeptide or fragment may share no more than 99%, 98%, 95%, 90%, 80%, 70%, 60%, 50% or even less amino acid sequence identity as compared to a natural sequence when suitably aligned.

The terms "hydrophilic" and "hydrophobic" refer to the degree of affinity that a substance has with water. A hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be characterized based on their hydrophobicity. A number of scales have been developed. An example is a scale developed by Levitt, M, et al., J Mol Biol (1976) 104:59, which is listed in Hopp, T P, et al., Proc Natl Acad Sci USA (1981) 78:3824. Examples of "hydrophilic amino acids" are arginine, lysine, threonine, alanine, asparagine, and glutamine. Of particular interest are the hydrophilic amino acids aspartate, glutamate, and serine, and glycine. Examples of "hydrophobic amino acids" are tryptophan, tyrosine, phenylalanine, methionine, leucine, isoleucine, and valine.

A "fragment" when applied to a protein, is a truncated form of a native biologically active protein that may or may not retain at least a portion of the therapeutic and/or biological activity. A "variant" when applied to a protein is a protein with sequence homology to the native biologically active protein that retains at least a portion of the therapeutic and/or biological activity of the biologically active protein. For example, a variant protein may share at least 70%, 75%, 80%, 85%, 90%, 95%, 96%, 97%, 98% or 99% amino acid sequence identity compared with the reference biologically active protein. As used herein, the term "biologically active protein moiety" includes proteins modified deliberately, as for example, by site directed mutagenesis, synthesis of the encoding gene, insertions, or accidentally through mutations.

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide that is known to comprise additional residues in one or both directions.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, «-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)$NR_2$ ("amidate"), P(O)R, P(O)OR', CO or $CH_2$ ("formacetal"), in which each R or R' is independently H or substituted or unsubstituted alkyl (1-20C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Fusion partner" refers to a peptide or polypeptide fused to the CTLA4 variant sequence described herein. The fusion partner may be fused to the CTLA4 variant sequence on the N- and/or C-terminus. Exemplary fusion partners include, but are not limited to, albumin, transferrin, adnectins (e.g., albumin-binding or pharmacokinetics extending (PKE) adnectins), Fc domain, and unstructured polypeptide, such as XTEN and PAS polypeptide (e.g. conformationally disordered polypeptide sequences composed of the amino acids Pro, Ala, and/or Ser), or a fragment of any of the foregoing. The fusion partner may be fused to the modified CTLA4 variant sequence for any purpose, including but not limited to, purification, manufacturability, half-life extension, enhanced biophysical properties (e.g. solubility or stability), reduced immunogenicity or toxicity, etc.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, ($5^{th}$ ed., 1991, National Institutes of Health, Bethesda M D)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

A "linker sequence" refers to an amino acid sequence having both its N- and C-termini fused to other peptides or polypeptides. A linker sequence may be present in a fusion protein, e.g., having its termini fused (in either order) to a CTLA4 variant sequence and a fusion partner sequence. Exemplary linker sequences may comprise between 0 amino acids (i.e., no linker sequence present) and 1, 2, 3, 4, 5, 6, 7, 8, 9, 10, 11, 12, 13, 14, 15, 16, 17, 18, 19, 20, 25, 30, 35, 40, 45, 50, 60, or 100 amino acids, or more. In some embodiments, the linker sequence may comprise between 1 and 40, between 1 and 30, between 1 and 20, between 1 and 10, between 1 and 5, between 2 and 40, between 2 and 30, between 2 and 20, between 2 and 10, between 5 and 40, between 5 and 30, between 5 and 20, or between 5 and 10 amino acids. In some embodiments, the linker sequence may comprise between 5 and 20 amino acids. In some embodiments, the linker sequence may comprise between 10 and 20 amino acids. Certain exemplary linker sequence described herein may be rich in serine and glycine residues, however, it is to be understood that the linker sequence is not limited to such sequences.

A "host cell" includes an individual cell or cell culture that can be or has been a recipient for vector(s) comprising exogenous polynucleotides. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

The term "Fc region" is used to define the C-terminal region of an immunoglobulin heavy chain, which may be generated by papain digestion of an intact antibody. The Fc region as described herein may be a native sequence Fc region or a variant Fc region. The Fc region as described herein, in some cases, comprises two constant domains, a CH2 domain, and a CH3 domain. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Imunological Interest, $5^{th}$ Ed. Public Health Service, National Institutes of Health, Bethesda, Md., 1991. The Fc region of an immunoglobulin generally comprises two constant domains, $CH_2$ and $CH_3$.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. In some cases, a variant Fc region still retains at least one effector function of the native sequence Fc region. In other cases, a variant Fc region may not have effector function of the native sequence Fc region. The variant Fc region can have at least one amino acid substitution compared to a native sequence Fc region or to the Fc region of a parent polypeptide, e.g. from about one to about ten amino acid substitutions, or from about one to about five amino acid substitutions in a native sequence Fc region or in the Fc region of the parent polypeptide. The variant Fc region herein can possess at least about 80% sequence identity with a native sequence Fc region and/or with an Fc region of a parent polypeptide, or at least about 90%, at least about 95%, at least about 96%, at least about 97%, at least about 98%, or at least about 99% sequence identity therewith.

An "individual" or a "subject" is a mammal, more preferably a human. Mammals also include, but are not limited to, farm animals, sport animals, pets, primates, horses, dogs, cats, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective to produce a desired result, such as that associated with a particular goal or purpose, such as any described herein.

The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, $18^{th}$ edition, A. Gennaro, ed., Mack Publishing Co., Easton, PA, 1990; and Remington, The Science and Practice of Pharmacy $20^{th}$ Ed. Mack Publishing, 2000).

OVERVIEW

In one aspect, the present disclosure provides a polypeptide comprising a CTLA4 (cytotoxic T-lymphocyte-associated antigen 4) variant sequence with improved target binding affinities, e.g., a modified CTLA4 fusion protein, compositions and kits comprising the same, and methods of use thereof.

T-cell lymphocytes play a critical role in cell-mediated immunity by providing for an adaptive response to specific pathogens. In some cases, a T-helper cell antigenic response requires activation of a first signaling pathway by the binding of the T-cell receptor to an antigen bound to MHC (major histocompatibility complex) on the surface of an antigen presenting cell (APC), and in the meantime, it also requires activation of a second signaling pathway, which can produce a co-stimulatory signal, by the binding of CD28 protein on the surface of the T-cell to CD80 (B7-1) and CD86 (B7-2) on the surface of the APC. The co-stimulatory pathway mediated by the binding of CD28 to CD80 and CD86 on the surface of APC can play a role in T-cell activation and differentiation, it can also be important in tissue migration and peripheral tolerance induction. Activated T-cells can also express on their cell surface CTLA4, a homologue of CD28 that can bind to CD80 and CD86 with higher affinity. In some cases, CTLA4 expression results in competitive binding to CD80 and CD86, blocking the CD80/86-CD28 interaction and terminating T-cell activation. In some cases, these signaling pathways determine the magnitude of a T-cell response to antigen, as well as downstream responses to antigen, agents that modulate one or more costimulatory signals, e.g., by blocking one or more of the interactions between CD80/CD86 and CD28 and/or CTLA4, can be effective in treating disorders that result from dysregulated immune responses.

In some embodiments, polypeptides comprising a CTLA4 variant sequence are provided herein with improved binding affinity for CD80 or CD86. In some embodiments, CTLA4 variant sequence-containing polypeptides as provided herein have improved immunosuppressive activity, e.g., enhanced inhibitory effect on T cell activation. Without wishing to be bound to a certain theory, in some embodiments, the improvement of the binding affinity for CD80 or CD86 is at least partly a result of a mutation at one or more positions as compared to a native human CTLA4 protein that has amino acid sequence SEQ ID NO: 1. In some embodiments, the subject polypeptide sequence comprises a mutation at one or more positions in the binding domain for CD80 or CD86 as compared to a native CTLA4 protein (SEQ ID NO: 1), thereby potentially inducing configurational change that affects the binding affinity for its ligand CD80 or CD86.

In some embodiments, a polypeptide that is a fusion protein comprising a CTLA4 variant sequence fuses to a fusion partner sequence is provided herein. In some embodiments, without wishing to be bound to a certain theory, the choice of the fusion partner sequence as described herein contributes to various advantages (e.g., stability, solubility, deliverability, bioavailability, or productivity) of the subject polypeptide as compared to a native CTLA4 protein (SEQ ID NO: 1) or some other CTLA4 fusion proteins, such as abatacept that has amino acid sequence SEQ ID NO: 2 or belatacept that has amino acid sequence SEQ ID NO: 3.

Sequence Identity

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity.

Optimal alignment of sequences for comparison may be conducted using the Megalign™ program in the Lasergene suite of bioinformatics software (DNASTAR, Inc., Madison, WI), using default parameters. This program embodies several alignment schemes described in the following references: Dayhoff, M. O. (1978) A model of evolutionary change in proteins-Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730. Alternative alignment programs are available, including but not limited to the BLAST algorithm, which may also be used to evaluate sequence identify, such as by using default parameters.

Preferably, the "percentage of sequence identity" is determined by comparing two optimally aligned sequences over a window of comparison (e.g. of at least 20 positions), wherein the portion of the polynucleotide or polypeptide sequence in the comparison window may comprise additions or deletions (i.e. gaps), such as gaps of 20 percent or less (e.g. 5 to 15 percent, or 10 to 12 percent), as compared to the reference sequences (which does not comprise additions or deletions) for optimal alignment of the two sequences. The percentage is typically calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

The sequence identity with respect to the amino acid sequences identified herein, is defined as the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign™ (DNASTAR, Inc., Madison, WI) software. Those skilled in the art can determine appropriate parameters for measuring alignment, including any algorithms needed to achieve maximal alignment over the full length of the sequences being compared. Percent identity may be measured over the length of an entire defined polypeptide sequence, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured. In some embodiments, percent identity is determined with respect to the full length of a noted reference sequence, such as a sequence provided herein. For example, sequence comparison between two amino acid sequences (or a shorter length thereof) of the present disclosure may be carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

CTLA4 Variant

The present disclosure provides compositions comprising polypeptides capable of binding to CD80 or CD86, uses thereof, and methods of making the same. In one aspect, the present disclosure provides a polypeptide comprising an amino acid sequence that is a variant of CTLA4 (CTLA4 variant sequence). A variant of CTLA4 as provided herein can be a polypeptide comprising a sequence related to a native CTLA4 sequence. A variant of CTLA4 be a polypeptide comprising a sequence having with about or greater than 50%, 55%, 60%, 65%, 70%, 75%, 80%, 85%, 90%, 95%, 96%, 97%, 98%, 99%, or 99.5% sequence identity to at least part of a native CTLA4 sequence (SEQ ID NO: 1).

Native CTLA4 protein can bind to CD80 and CD86 via its extracellular domain or more specifically, its binding domain that can form a three-dimensional configuration receiving and binding to CD80 or CD86. A variant of CTLA4 as provided herein can have binding capacity to CD80, CD86, or both via at least a portion of its amino acid sequence that is related to the extracellular domain or the binding domain of a native CTLA4 protein. In some cases, a variant of CTLA4 is a polypeptide comprising a sequence with about or greater than 50%, 55%, 60%, 65%, 70%, 75%, 80%, 85%, 90%, 95%, 96%, 97%, 98%, 99%, or 99.5% sequence identity to a portion or an entirety of an extracellular domain of a native CTLA4 sequence, e.g., amino acids 36-161 of SEQ ID NO: 1, or amino acids 1-124 of abatacept (SEQ ID NO: 2). In some cases, a variant of CTLA4 is a polypeptide comprising a sequence with about or greater than 50%, 55%, 60%, 65%, 70%, 75%, 80%, 85%, 90%, 95%, 96%, 97%, 98%, 99%, or 99.5% sequence identity to a binding domain of a native CTLA4 sequence, e.g., amino acids 58-149 of SEQ ID NO: 1, or, or amino acids 21-112 of SEQ ID NO: 2.

Extracellular domain of a native CTLA4 protein can comprise a sequence as amino acids 36-161 in SEQ ID NO: 1 or amino acids 1-124 of SEQ ID NO: 2, and binding domain of a native CTLA4 protein can comprise an amino acid sequence starting from anywhere between amino acids 1 and 21 and ending anywhere between amino acids 112 and 124. In some cases, a variant of CTLA4 as provided herein can comprise an amino sequence with about or greater than 50%, 55%, 60%, 65%, 70%, 75%, 80%, 85%, 90%, 95%, 96%, 97%, 98%, 99%, or 99.5% sequence identity to an amino acid sequence starting from anywhere between amino acids 1 and 8, 8 and 16, or 16 and 21, and ending anywhere between amino acids 112 and 124 of SEQ ID NO: 2. In some cases, a variant of CTLA4 as provided herein can comprise an amino sequence with about or greater than 50%, 55%, 60%, 65%, 70%, 75%, 80%, 85%, 90%, 95%, 96%, 97%, 98%, 99%, or 99.5% sequence identity to an amino acid sequence starting from anywhere between amino acids 1 and 21, and ending anywhere between amino acids 112 and 115, 115 and 118, 118 and 121, or 121 and 124 of SEQ ID NO: 2. In some cases, a variant of CTLA4 as provided herein can comprise an amino sequence with about or greater than 50%, 55%, 60%, 65%, 70%, 75%, 80%, 85%, 90%, 95%, 96%, 97%, 98%, 99%, or 99.5% sequence identity to an amino acid sequence starting from anywhere between amino acids 1 and 8, 8 and 16, or 16 and 21, and ending anywhere between amino acids 112 and 115, 115 and 118, 118 and 121, or 121 and 124 of SEQ ID NO: 2.

As provided herein, a variant of CTLA4 can comprise an amino acid sequence that has one or more mutations as compared to at least a portion of a native CTLA4 sequence, e.g., SEQ ID NO: 1, e.g., an extracellular domain or a binding domain of a native CTLA4 sequence, e.g., amino acids 36-161 of SEQ ID NO: 1 or amino acids 1-124 of SEQ ID NO: 2, or amino acids 56-147 of SEQ ID NO: 1 or amino acids 21-112 of SEQ ID NO: 2. In some cases, a variant of CTLA4 has at least 1, 2, 3, 4, 5, 6, 7, 8, 9, 10, 15, 20, 25, 30, 35, 40, or 50 mutations as compared to at least a portion of a native CTLA4 sequence, e.g., amino acids 36-161 of SEQ ID NO: 1, amino acids 1-124 of SEQ ID NO: 2, amino acids 56-147 of SEQ ID NO: 1, or amino acids 21-112 of SEQ ID NO: 2. In some cases, a variant of CTLA4 has up to 2, 3, 4, 5, 6, 7, 8, 9, 10, 15, 20, 25, 30, 35, 40, or 50 mutations as compared to at least a portion of a native CTLA4 sequence, e.g., amino acids 36-161 of SEQ ID NO: 1, amino acids 1-124 of SEQ ID NO: 2, amino acids 56-147 of SEQ ID NO: 1, or amino acids 21-112 of SEQ ID NO: 2.

Mutation

In some embodiments provided herein, a subject polypeptide as described herein may have one or more mutations with respect to a reference sequence, e.g., at least a portion of a CTLA4 protein. A mutation may be a deletion, an insertion or addition, or a replacement or substitution to an amino acid residue. A "deletion" refers to a change in an amino acid sequence due to the absence of one or more amino acid residues. An "insertion" or "addition" refers to changes in an amino acid sequence resulting in the addition of one or more amino acid residues as compared to a reference sequence. A "replacement" or "substitution" refers to the replacement of one or more amino acids by different amino acids. In the context of the present disclosure, the mutations of a subject polypeptide with respect to a reference sequence, e.g., at least a portion of a native CTLA4 protein, may be determined by comparison of the subject polypeptide or a fraction thereof to the reference sequence. Optimal alignment of sequences for comparison may be conducted according to any of the known methods in the art.

A mutation may be identified by the mutation site. The mutation site is the position on a reference sequence where a deletion, an addition, or a substitution takes place. The amino acid residues on a reference sequence are numbered from the N-terminus to the C-terminus, and the mutation site is the numbering of the amino acid residue on which a deletion, an addition, or a substitution takes place. For example, position 26 on a reference sequence is the position where the $26^{th}$ amino acid residue locates starting from the N-terminus.

In the context of the present disclosure, the scenario where addition of one or more amino acid residues between a specific position and the position immediately after the specific position (or after the specific position when the amino acid residue at the specific position is the last amino acid residue) on the reference sequence is considered as a substitution of an amino acid residue at the specific position with more than one amino acid residues. For instance, a mutant amino acid sequence XYYZ is considered to have a substitution of Y at the second position with YY when compared to a reference amino acid sequence XYZ, where X, Y, and Z represent individual amino acid residues, respectively. Therefore, in the context of the present disclosure, one mutation at a specific position is intended to mean a deletion of one amino acid residue at the specific position, or a substitution of an amino acid residue at the specific position with another amino acid residue or more than one amino acid residues.

For the purpose of describing a mutation with respect to a reference sequence, the one-letter amino acid code may be used. In this respect, for example, when a subject polypeptide is said to comprise a mutation from G to I at position 26, which may be described as "G26I," with respect to a reference sequence, it is intended to mean that the $26^{th}$ amino acid residue, which is a glycine (G) residue according to the reference sequence, is substituted by an alanine residue in a subject polypeptide or a fraction thereof. In the context of the present disclosure, for example, when a subject polypeptide is said to comprise a deletion of a glycine (G) residue at position 26, which may be described as "G26del" with respect to a reference sequence, it is intended to mean that the $26^{th}$ amino acid residue, which is a glycine (G) residue according to the reference sequence, does not exist in a subject polypeptide or a fraction thereof. In the context of the present disclosure, for example, when a subject polypeptide is said to comprise an addition of one or more amino acid residues after the glycine (G) residue at position 26, which may be described by "G26_ins" followed by a list of the added amino acid residues, it is intended to mean that the listed one or more amino acid residues are added between the $26^{th}$ amino acid residue, which is glycine (G), and the $27^{th}$ amino acid or (in a case where the $26^{th}$ amino acid residue is the last amino acid residue according to the reference sequence) after the $26^{th}$ amino acid residue, which is glycine (G).

In some embodiments, a subject polypeptide comprises a CTLA4 variant sequence having one or more mutations with respect to amino acids 1-124 of SEQ ID NO. 2. In some embodiments, the CTLA4 variant sequence in the subject polypeptide comprises a mutation at any one or more positions with respect to amino acids 1-124 of SEQ ID NO: 2. In some embodiments, the CTLA4 variant sequence in the subject polypeptide comprises a mutation at any one or more positions with respect to amino acids 1-124 of SEQ ID NO: 2, like positions 16, 18, 24, 25, 27, 28, 29, 30, 32, 33, 40, 41, 42, 48, 49, 50, 51, 52, 53, 54, 56, 58, 59, 60, 61, 63, 64, 65, 68, 69, 70, 77, 80, 85, 86, 92, 93, 94, 96, 105, 106, 107, 122, 117, 118, or any combinations thereof. In some embodiments, the CTLA4 variant sequence in the subject polypeptide comprises a mutation at any one or more positions with respect to amino acids 1-124 of SEQ ID NO: 2, like positions 18, 24, 27, 29, 33, 40, 41, 49, 50, 51, 68, 77, 86, 92, 93, 94, 105, 107, 122, 117, 118, or any combinations thereof. In some embodiments, the CTLA4 variant sequence in the subject polypeptide comprises a mutation at any one or more positions with respect to amino acids 1-124 of SEQ ID NO: 2, like positions 18, 40, 68, 77, 86, 92, 107, 117, 118, and 122.

In some embodiments, the CTLA4 variant sequence in the subject polypeptide comprises any type of mutation at any one or more positions with respect to amino acids 1-124 of SEQ ID NO: 2. For instance, the CTLA4 variant sequence in the subject polypeptide can have deletion at any one or more positions with respect to amino acids 1-124 of SEQ ID NO: 2. In some embodiments, the CTLA4 variant sequence in the subject polypeptide comprises a deletion at any one or more positions with respect to amino acids 1-124 of SEQ ID NO: 2, like positions 16, 18, 24, 25, 27, 28, 29, 30, 32, 33, 40, 41, 42, 48, 49, 50, 51, 52, 53, 54, 56, 58, 59, 60, 61, 63, 64, 65, 68, 69, 70, 77, 80, 85, 86, 92, 93, 94, 96, 105, 106, 107, 122, 117, 118, or any combinations thereof. The CTLA4 variant sequence in the subject polypeptide comprises any type of substitution at any one or more positions with respect to amino acids 1-124 of SEQ ID NO: 2. In some embodiments, the CTLA4 variant sequence in the subject polypeptide comprises any type of substitution at any one or more positions with respect to amino acids 1-124 of SEQ ID NO: 2, like positions 16, 18, 24, 25, 27, 28, 29, 30, 32, 33, 40, 41, 42, 48, 49, 50, 51, 52, 53, 54, 56, 58, 59, 60, 61, 63, 64, 65, 68, 69, 70, 77, 80, 85, 86, 92, 93, 94, 96, 105, 106, 107, 122, 117, 118, or any combinations thereof. In some embodiments, the CTLA4 variant sequence in the subject polypeptide comprises any type of substitution at any one or more positions with respect to amino acids 1-124 of SEQ ID NO: 2, like positions 18, 24, 27, 29, 33, 40, 41, 49, 50, 51, 68, 77, 86, 92, 93, 94, 105, 107, 122, 117, 118, or any combinations thereof. In some embodiments, the CTLA4 variant sequence in the subject polypeptide comprises any type of substitution at any one or more positions with respect to amino acids 1-124 of SEQ ID NO: 2, like positions 18, 40, 68, 77, 86, 92, 107, 117, 118, and 122.

In some embodiments, the CTLA4 variant sequence in the subject polypeptide comprises one or more amino acid substitutions like S18R, S18N, A24S, A24E, G27D, G27DK, G27DKA, G27E, G27H, G27K, G27KK, G27R, G27W, G27Y, A29S, A29T, A29H, A29Y, T30N, V321, R33W, A40T, D41G, D41N, A49P, A50T, A50M, T51N, M53Y, M54K, N56D, L61E, S64P, 165S, G68D, G68E, G68F, G68H, G68K, G68W, G68Y, S70F, L77V, M85A, D86N, C92S, C92Y, K93C, K93N, K93F, K93M, K93P, K93R, K93V, K93W, K93Q, V94L, G105S, G105D, I106F, G107D, P117S, E118K, D122H, or any appropriate combinations thereof with respect to amino acids 1-124 of SEQ ID NO: 2. In some embodiments, the CTLA4 variant sequence in the subject polypeptide comprises one or more amino acid substitutions like S18R, S18N, A24S, G27DKA, G27DK, G27K, G27R, G27W, G27Y, G27E, G27KK, A29T, A40T, A49P, A50T, G68F, G68K, G68W, G68Y, G68H, G68D, G68E, L77V, D86N, C92S, C92Y, K93V, K93W, K93P, K93C, K93F, K93R, V94L, G105S, G107D, P117S, E118K, D122H, or any appropriate combinations thereof with respect to amino acids 1-124 of SEQ ID NO: 2. As described above, the CTLA4 variant sequence in the subject polypeptide can have any type of mutation at any one or more positions, for instance, amino acid G at position 27 with respect to amino acids 1-124 of SEQ ID NO: 2 can be substituted for any type of amino acid or group of amino acid residues, e.g., D, DK, DKA, E, H, K, KK, R, W, or Y, or amino acid K at position 93 with respect to amino acids 1-124 of SEQ ID NO: 2 can also be substituted for any type of amino acid or group of amino acid residues, e.g., N, F, M, V, W, P, C, F, or R.

In some embodiments, the CTLA4 variant sequence in the subject polypeptide can have any combination of mutations with respect to amino acids 1-124 of SEQ ID NO: 2. For instance, the CTLA4 variant sequence in the subject polypeptide can have any combination of mutations with respect to amino acids 1-124 of SEQ ID NO: 2, like any one in Table 5, e.g., G27DKA/R33W, G27DKA/G68F, R33W/G68F, G27R/G68Y, G27H/G68F, G27DK/G68F, G27DK/G68D, G27DK/G68E, G27D/G68F, G27E/G68F, G27H/G68D, G27H/G68E, G27DKA/G68F, G27H/G68F, G27DK/G68F, G27DKA/G68F/D122H, G27DKA/G68F/A40T/D122H, G27DKA/G68F/A40T/P117S, G27DKA/G68F/L77V, G27DKA/G68F/C92S/K93M, G27DK/G68F/A49P/A50T, G27DK/G68F/A40T/D86N/G105S, G27KK/G68F, G27DKA/G68F/P117S, G27DKA/G68F/A49P/A50T, G27DK/G68F/A40T, G27DK/G68F/L77V/G105S/P117S, G27DK/G68F/L77V, G27DK/G68F/C92S/K93M, G27DK/G68F/P117S, G27DKA/G68F/G105S, G27DKA/G68F/D86N, G27DK/G68F/D122H, G27DK/G68F/A40T/G105S, G27DK/G68F/G105S, G27DK/G68F/D86N, G27DKA/G68F/A40T, G27DKA/G68F/K93M, G27DK/G68F/K93M, or G27DKA/A40T/G68F/K93M. In some embodiments, the CTLA4 variant sequence in the subject polypeptide comprises a combination of amino acid substitutions G27DKA/A40T/G68F/K93M with respect to SEQ ID NO: 2. In some embodiments, the CTLA4 variant sequence in the subject polypeptide comprises a combination of amino acid substitutions G27DKA/G68F/A40T with respect to SEQ ID NO: 2. In some embodiments, the CTLA4 variant sequence in the subject polypeptide comprises a combination of amino acid substitutions G27DKA/G68F/K93M with respect to SEQ ID NO: 2. In some embodiments, the CTLA4 variant sequence in the subject polypeptide comprises a combination of amino acid substitutions G27DKA/G68F/A40T/P117S with respect to SEQ ID NO: 2. In some embodiments, the CTLA4 variant sequence in the subject polypeptide comprises a combination of amino acid substitutions G27DKA/G68F/P117S with respect to SEQ ID NO: 2. In some embodiments, the CTLA4 variant sequence in the subject polypeptide comprises a combination of amino acid substitutions G27H/G68F with respect to SEQ ID NO: 2. In some embodiments, the CTLA4 variant sequence in the subject polypeptide comprises a combination of amino acid substitutions G27DKA/G68F with respect to SEQ ID NO: 2. In some embodiments, the CTLA4 variant sequence in the subject polypeptide comprises a combination of amino acid substitutions G27DK/G68F/K93M with respect to SEQ ID NO: 2. In some embodiments, the CTLA4 variant sequence in the subject polypeptide comprises a combination of amino acid substitutions G27DK/G68F/A40T with respect to SEQ ID NO: 2. In some embodiments, the CTLA4 variant sequence in the subject polypeptide comprises a combination of amino acid substitutions G27DK/G68F/L77V/G105S/P117S with respect to SEQ ID NO: 2. In some embodiments, the CTLA4 variant sequence in the subject polypeptide comprises a combination of amino acid substitutions G27DK/G68F/L77V with respect to SEQ ID NO: 2. In some embodiments, the CTLA4 variant sequence in the subject polypeptide comprises a combination of amino acid substitutions G27DK/G68F/P117S with respect to SEQ ID NO: 2. In some embodiments, the CTLA4 variant sequence in the subject polypeptide comprises a combination of amino acid substitutions G27DK/G68F/D122H with respect to SEQ ID NO: 2.

In some embodiments, the CTLA4 variant sequence in a subject polypeptide comprises an amino acid sequence with about or greater than 70%, 75%, 80%, 85%, 90%, 95%, 96%, 97%, 98%, 99%, 99.5% or 100% sequence identity to amino acids 1-126 of SEQ ID NO: 6.

Binding Affinity

As described above, a subject polypeptide as provided herein comprises a CTLA4 binding domain and is capable of binding to CD80, CD86, or both. A subject polypeptide can typically exhibit high binding affinity to CD80, Cd86, or both. In some embodiments, the CD80 is human CD80. In some embodiments, the CD86 is human CD86.

Binding affinity of molecules to CD80 or CD86 in solution or immobilized on an array can be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques;

surface plasmon resonance (SPR), by which changes in mass of materials adsorbed at surfaces are measured; techniques using radioisotopes, including conventional radioisotope binding and scintillation proximity assays (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as atomic force microscopy (AFM), scanning force microscopy (SFM) or scanning electron microscopy (SEM); and techniques such as electrochemical, impedance, acoustic, microwave, and IR/Raman detection. See, e.g., Mere L, et al., "*Miniaturized FRET assays and microfluidics: key components for ultra-high-throughput screening,*" *Drug Discovery Today* 4(8): 363-369 (1999), and references cited therein; Lakowicz J R, *Principles of Fluorescence Spectroscopy,* 2nd Edition, *Plenum Press* (1999), or Jain K K: *Integrative Omics, Pharmacoproteomics, and Human Body Fluids. In: Thongboonkerd V, ed., ed. Proteomics of Human Body Fluids: Principles, Methods and Applications*. Volume 1: Totowa, N.J.: *Humana Press,* 2007, each of which is herein incorporated by reference in its entirety.

In some embodiments provided herein, binding affinity of a subject polypeptide to CD80 or CD86 is measured by surface plasmon resonance. Biacore™ surface plasmon resonance (SPR) system (GE Healthcare, Chicago IL) may be used to measure binding affinity of a subject polypeptide. Exemplary SPR analysis systems include, but are not limited to, Biacore™ X100, Biacore™ T200, Biacore™ 3000 or Biacore™ 4000 instrument, and commercial sensor chips series. In a typical application of the Biacore™ systems, interaction kinetics are analyzed by monitoring the interaction as a function of time over a range of analyte concentrations, and then fitting the whole data set to a mathematical model describing the interaction. The association phase (during sample injection) contains information on both association and dissociation processes, while only dissociation occurs during the dissociation phase (after sample injection, when buffer flow removes dissociated analyte molecules). Those skilled in the art can choose or determine appropriate parameters and/or conditions for carrying out the binding affinity assay according to manufacturer's manual. In some embodiments, the binding affinity of a subject polypeptide is determined by surface plasmon resonance at 37° C. In some embodiments, the binding affinity of a subject polypeptide is determined by surface plasmon resonance at room temperature, e.g. around 22 to 25° C. In some embodiments, the binding affinity of a subject polypeptide is determined by surface plasmon resonance at a temperature no higher than 37° C.

In one aspect, the present disclosure provides a polypeptide having a high binding affinity for CD80, CD86, or both. In some embodiments, the polypeptide has a binding affinity for CD80, CD86, or both that is greater than that of abatacept, e.g., SEQ ID NO: 2. For instance, the polypeptide as provided herein has a binding affinity for CD80, CD86, or both that is at least 1.1, at least 1.2, at least 1.3, at least 1.4, at least 1.5, at least 1.6, at least 1.7, at least 1.8, at least 1.9, at least 2, at least 2.2, at least 2.4, at least 2.6, at least 2.8, at least 3, at least 3.5, at least 4, at least 4.5, at least 5, at least 6, at least 7, at least 8, at least 9, at least 10, at least 12, at least 15, at least 20, at least 25, at least 30, at least 40, at least 50, at least 100, at least 150, at least 200, at least 250, or at least 300 times greater than that of abatacept (SEQ ID NO: 2). In the context of the present disclosure, the binding affinity for CD80, CD86, or both is compared between two different molecules as determined by the same binding assay under the same experimental conditions, for instance, as determined by surface plasmon resonance at 37° C.

In some embodiments, the polypeptide as provided herein has an improved binding affinity for CD80 as compared to SEQ ID NO: 2, but relatively similar or lower binding affinity for CD86 as compared to SEQ ID NO:2. In some embodiments, the polypeptide as provided herein has an improved binding affinity for CD86 as compared to SEQ ID NO: 2, but relatively similar or lower binding affinity for CD80 as compared to SEQ ID NO:2. In some embodiments, the polypeptide as provided herein has an improved binding affinity for both CD80 and CD86 as compared to SEQ ID NO: 2.

In some embodiments, the polypeptide has a binding affinity for CD80, CD86, or both that is greater than that of belatacept, e.g., SEQ ID NO: 3. For instance, the polypeptide as provided herein has a binding affinity for CD80, CD86, or both that is at least 1.1, at least 1.2, at least 1.3, at least 1.4, at least 1.5, at least 1.6, at least 1.7, at least 1.8, at least 1.9, at least 2, at least 2.2, at least 2.4, at least 2.6, at least 2.8, at least 3, at least 3.5, at least 4, at least 4.5, at least 5, at least 6, at least 7, at least 8, at least 9, at least 10, at least 12, at least 15, at least 20, at least 25, at least 30, at least 40, at least 50, or at least 100 times greater than that of belatacept (SEQ ID NO: 3).

In some embodiments, the polypeptide has a binding affinity for CD80, CD86, or both that is greater than that of SEQ ID NO: 4, 5, or both. For instance, the polypeptide has a binding affinity for CD80, CD86, or both that is at least 1.1, at least 1.2, at least 1.3, at least 1.4, at least 1.5, at least 1.6, at least 1.7, at least 1.8, at least 1.9, at least 2, at least 2.2, at least 2.4, at least 2.6, at least 2.8, at least 3, at least 3.5, at least 4, at least 4.5, at least 5, at least 6, at least 7, at least 8, at least 9, at least 10, at least 12, at least 15, at least 20, at least 25, at least 30, at least 40, at least 50, or at least 100 times greater than that of SEQ ID NO: 4, 5, or both.

In another aspect, the present disclosure provides a polypeptide having a low binding affinity for CD80, CD86, or both. In some embodiments, a polypeptide has a binding affinity for CD80, CD86, or both that is lower than that of SEQ ID NO: 2. For instance, a polypeptide as provided herein has a binding affinity for CD80, CD86, or both that is at least 1.1, at least 1.2, at least 1.3, at least 1.4, at least 1.5, at least 1.6, at least 1.7, at least 1.8, at least 1.9, at least 2, at least 2.2, at least 2.4, at least 2.6, at least 2.8, at least 3, at least 3.5, at least 4, at least 4.5, at least 5, at least 6, at least 7, at least 8, at least 9, at least 10, at least 12, at least 15, at least 20, at least 25, at least 30, at least 40, at least 50, or at least 100 times greater than that of SEQ ID NO: 2.

The binding affinity of a subject polypeptide for CD80 or CD86 may be characterized by $k_a$, $k_d$ or $K_D$. The term "$k_a$," as used herein, can to refer to the rate constant for association of an polypeptide to an antigen. The term "$k_d$," as used herein, can refer to the rate constant for dissociation of an polypeptide from the protein-protein complex. The term "$K_D$," as used herein, can to refer to the equilibrium dissociation constant of a protein-protein interaction. For purposes of the present disclosure, $K_D$ is defined as the ratio of the two kinetic rate constants $k_d/k_a$. The smaller the equilibrium dissociation constant the tighter the subject polypeptide and CD80 or CD86 bind to each other.

In some embodiments, a polypeptide as disclosed herein binds to CD80 with a $k_a$ of at least $10^2$ $M^{-1}s^{-1}$, at least $5\times10^2 M^{-1}s^{-1}$, at least $10^3$ $M^{-1}s^{-1}$, at least $5\times10^3 M^{-1}s^{-1}$, at least $10^4$ M$^{-1}$s$^{-1}$, at least $5\times10^4$ M$^{-1}$s$^{-1}$, at least $10^5$ M$^{-1}$s$^{-1}$, at least $5\times10^5$ M$^{-1}$s$^{-1}$, at least $10^6$ M$^{-1}$s$^{-1}$, at least $5\times10^6$ M$^{-1}$s$^{-1}$, at least $10^7$ M$^{-1}$s$^{-1}$, at least $5\times10^7$ M$^{-1}$s$^{-1}$, at least $10^8$ M$^{-1}$s$^{-1}$, at least $5\times10^8$ M$^{-1}$s$^{-1}$, at least $10^9$ M$^{-1}$s$^{-1}$, at least $5\times10^9$ M$^{-1}$s$^{-1}$ or with a $k_a$ of any range between any two of these values. In some embodiments, a polypeptide as disclosed herein binds to CD80 with a $k_a$ between $10^5$ M$^{-1}$s$^{-1}$ and $10^5$ M$^{-1}$s$^{-1}$, between $5\times10^5$ M$^{-1}$s$^{-1}$ and $1\times10^6$M$^{-1}$s$^{-1}$, between $7.5\times10^5$ M$^{-1}$s$^{-1}$ and $2.5\times10^6$ M$^{-1}$s$^{-1}$, or between $1\times10^5$ M$^{-1}$s$^{-1}$ and $5\times10^6$ M$^{-1}$s$^{-1}$.

In some embodiments, a polypeptide as disclosed herein binds to CD86 with a $k_a$ of at least $10^2$ M$^{-1}$s$^{-1}$, at least $5\times10^2$M$^{-1}$s$^{-1}$, at least $10^3$ M$^{-1}$s$^{-1}$, at least $5\times10^3$M$^{-1}$s$^{-1}$, at least $10^4$ M$^{-1}$s$^{-1}$, at least $5\times10^4$ M$^{-1}$s$^{-1}$, at least $10^5$ M$^{-1}$s$^{-1}$, at least $5\times10^5$ M$^{-1}$s$^{-1}$, at least $10^6$ M$^{-1}$s$^{-1}$, at least $5\times10^6$ M$^{-1}$s$^{-1}$, at least $10^7$ M$^{-1}$s$^{-1}$, at least $5\times10^7$ M$^{-1}$s$^{-1}$, at least $10^8$ M$^{-1}$s$^{-1}$, at least $5\times10^8$ M$^{-1}$s$^{-1}$, at least $10^9$ M$^{-1}$s$^{-1}$, at least $5\times10^9$ M$^{-1}$s 1 or with a $k_a$ of any range between any two of these values. In some embodiments, a polypeptide as disclosed herein binds to CD86 with a $k_a$ between $10^5$ M$^{-1}$s$^{-1}$ and $10^5$ M$^{-1}$s$^{-1}$, between $5\times10^5$ M$^{-1}$s$^{-1}$ and $1\times10^6$M$^{-1}$s$^{-1}$, between $7.5\times10^5$M$^{-1}$s$^{-1}$ and $2.5\times10^6$M$^{-1}$s$^{-1}$, or between $1\times10^5$ M$^{-1}$s$^{-1}$ and $5\times10^6$M$^{-1}$s$^{-1}$.

In certain embodiments, a polypeptide as disclosed herein binds to CD80 with a $k_a$ of 2 s 1 or less, 1.5 s$^{-1}$ or less, 1 s$^{-1}$ or less, 0.5 s$^{-1}$ or less, 0.1 s$^{-1}$ or less, $5\times10^{-2}$ s$^{-1}$ or less, $10^{-2}$ s$^{-1}$ or less, $5\times10^{-3}$ s$^{-1}$ or less, $10^{-3}$ s$^{-1}$ or less, $5\times10^{-4}$ s$^{-1}$ or less, $10^{-4}$ s$^{-1}$ or less, $5\times10^{-5}$ s$^{-1}$ or less, $10^{-5}$ s$^{-1}$ or less, $5\times10^{-6}$ s$^{-1}$ or less, $10^{-6}$ s$^{-1}$ or less, $5\times10^{-7}$s$^{-1}$ or less, $10^{-1}$ s$^{-1}$ or less, $5\times10^{-8}$ s 1 or less, $10^{-8}$ s$^{-1}$ or less, or with a karate of any range between any two of these values. In certain embodiments, a polypeptide as disclosed herein binds to CD86 with a $k_a$ of 2 s 1 or less, 1.5 s$^{-1}$ or less, 1 s$^{-1}$ or less, 0.5 s$^{-1}$ or less, 0.1 s$^{-1}$ or less, $5\times10^{-2}$ s$^{-1}$ or less, $10^{-2}$ s$^{-1}$ or less, $5\times10^{-3}$ s$^{-1}$ or less, $10^{-3}$ s$^{-1}$ or less, $5\times10^{-4}$ s$^{-1}$ or less, $10^{-4}$ s$^{-1}$ or less, $5\times10^{-5}$ s$^{-1}$ or less, $10^{-5}$ s$^{-1}$ or less, $5\times10^{-6}$ s$^{-1}$ or less, $10^{-6}$ s$^{-1}$ or less, $5\times10^{-7}$ s$^{-1}$ or less, $10^{-7}$ s$^{-1}$ or less, $5\times10^{-8}$ s$^{-1}$ or less, $10^{-8}$ s 1 or less, or with a karate of any range between any two of these values.

In some embodiments, a polypeptide as disclosed herein binds to CD80 with a $K_D$ of $5\times10^{-6}$M or less, $10^{-6}$ M or less, $5\times10^{-7}$ M or less, $10^{-7}$M or less, $5\times10^{-8}$ M or less, $10^{-8}$ M or less, $5\times10^{-9}$M or less, $10^{-9}$ M or less, $5\times10^{-10}$M or less, $10^{10}$ M or less, $5\times10^{-11}$ M or less, $10^{-11}$ M or less, $5\times10^{-12}$ M or less, $10^{-12}$ M or less, $5\times10^{-13}$ M or less, $10^{-13}$M or less, $5\times10^{44}$ M or less, $10^{-14}$ M or less, $5\times10^{-15}$M or less, $10^{-15}$ M or less, or with a Kp of any range between any two of these values.

In some embodiments, a polypeptide as disclosed herein binds to CD86 with a $K_D$ of $5\times10^{-6}$M or less, $10^{-6}$ M or less, $5\times10^{-7}$M or less, $10^{-7}$M or less, $5\times10^{-8}$ M or less, $10^{-8}$ M or less, $5\times10^{-9}$M or less, $10^{-9}$ M or less, $5\times10^{-10}$M or less, $10^{10}$ M or less, $5\times10^{-11}$ M or less, $10^{-11}$ M or less, $5\times10^{-12}$ M or less, $10^{-12}$ M or less, $5\times10^{-13}$ M or less, $10^{-13}$M or less, $5\times10^{44}$ M or less, $10^{-14}$ M or less, $5\times10^{-15}$M or less, $10^{-15}$ M or less, or with a $K_D$ of any range between any two of these values.

In certain embodiments, the kinetic properties of a polypeptide as disclosed herein are improved as compared to abatacept (SEQ ID NO: 2) in a comparable assay. For example, in certain embodiments, a polypeptide of the present disclosure binds to CD80, CD86, or both with a $k_a$ rate ranging from approximately 1.1 to 1000 times of the corresponding $k_a$ of abatacept. In some embodiments, a polypeptide of the present disclosure binds to CD80, CD86, or both with a $k_a$ rate that is about 1.1, about 1.2, about 1.5, about 2, about 2.5, about 3, about 3.5, about 4, about 5, about 7.5, about 10, about 20, about 50, about 100, about 200, about 500, about 750, or about 1000 times of the corresponding $k_a$ of abatacept, or with a $k_a$ rate within any range between any two of these values. In some embodiments, a polypeptide of the present disclosure binds to CD80, CD86, or both with a $k_d$ rate ranging from approximately 0.0001 to 0.99 times of the corresponding $k_d$ of abatacept. In some embodiments, a polypeptide of the present disclosure binds to CD80, CD86, or both with a karate that is about 0.0001, about 0.0002, about 0.001, about 0.002, about 0.005, about 0.01, about 0.02, about 0.05, about 0.075, about 0.1, about 0.2, about 0.25, about 0.3, about 0.4, about 0.5, about 0.075, about 0.75, about 0.8, about 0.9, about 0.92, about 0.94, about 0.96, about 0.98, or about 0.99 times of the corresponding $k_a$ of abatacept, or with a $k_d$ rate within any range between any two of these values. In some embodiments, a polypeptide of the present disclosure binds to CD80, CD86, or both with a $K_D$ rate ranging from approximately 0.0001 to 0.99 times of the corresponding $K_D$ of abatacept. In some embodiments, a polypeptide of the present disclosure binds to CD80, CD86, or both with a karate that is about 0.0001, about 0.0002, about 0.001, about 0.002, about 0.005, about 0.01, about 0.02, about 0.05, about 0.075, about 0.1, about 0.2, about 0.25, about 0.3, about 0.4, about 0.5, about 0.075, about 0.75, about 0.8, about 0.9, about 0.92, about 0.94, about 0.96, about 0.98, or about 0.99 times of the corresponding $K_D$ of abatacept, or with a $K_D$ rate within any range between any two of these values.

In some embodiments, the binding of a subject polypeptide has pH dependence. In some embodiments, pH dependence is defined as the ratio between the binding affinity for CD80, CD86, or both at pH7.4 and at pH6.0. The pH dependence can be in the form of the fold of decrease of binding affinity from pH7.4 to pH6.0, or the fold of increase of binding affinity from pH7.4 to pH6.0. In some embodiments, the pH dependence is calculated as the ratio between the $K_D$ value at pH 6.0 and the $K_D$ value at pH 7.4, and the pH dependence, i.e., the ratio, indicates the fold of affinity decrease from the pH7.4 to pH6.0. If the pH dependence of a subject polypeptide described herein is over 1, it means that the polypeptide binds to CD80, CD86, or both in such a pH-dependent manner that its binding to CD80, CD86, or both at pH7.4 is higher than at pH6.0. If the pH dependence of a subject polypeptide described herein is lower than 1, it means that the polypeptide binds to CD80, CD86, or both in such a pH-dependent manner that its binding to CD80, CD86, or both at pH6.0 is higher than at pH7.4. The ability to maintain binding under neutral condition (e.g., pH is about 7.0, 7.1, 7.2, 7.3, 7.4, or 7.5) but significantly reduce under acidic conditions allows a subject polypeptide's dissociation from its binding partner (e.g., CD80 or CD86) in acidic condition (e.g., inside lysosome, e.g., pH is less than 7.0, or about 6.5, 6.0, 5.5, or 5.0). In some embodiments, the ability to maintain binding under neutral condition but significantly reduce under acidic conditions allows the subject polypeptide to escape the degradation by lysosomes under acidic conditions and to return to the plasma where it can bind to its binding partner (e.g., CD80 and CD86) under neutral condition again. Not wishing to be bound by any theory, it is believed that a subject polypeptide having such pH dependent binding pattern (e.g., higher binding affinity under neutral condition than under acidic condition) has superior properties in terms of antigen neutralization and clearance relative to an otherwise identical polypeptide that binds in a pH-independent mode.

In some embodiments, a subject polypeptide provided herein has a pH dependence of binding affinity for CD80, CD86, or both higher than 1, such as at least 2, 3, 4, 5, 6, 7, 8, 9, 10, 15, 20, 25, 30, 35, 40, 45, 50, 55, 60, 70, 80, 90, 100 or more. In some embodiments, a subject polypeptide has a pH dependence of binding affinity for CD80, CD86, or both higher than that of SEQ ID NO: 2. In some embodiments, a subject polypeptide has a pH dependence of binding affinity for CD80, CD86, or both at least 1, 2, 5, 10, 15, 20, 25, 30, 35, 40, 45, 50, 55, 60, 65, 70, 75, or 80 times higher than that of SEQ ID NO: 2. In some embodiments, a subject polypeptide has a pH dependence of binding affinity for CD80, CD86, or both higher than that of SEQ ID NO: 3. In some embodiments, a subject polypeptide has a pH dependence of binding affinity for CD80, CD86, or both at least 1, 2, 5, 10, 15, 20, 25, 30, 35, 40, 45, or 50 times higher than that of SEQ ID NO: 3.

In some embodiments, a subject polypeptide exhibits competitive inhibitory effect on other proteins for binding to CD80 or CD86. The binding affinity of a subject polypeptide for CD80 or CD86 can be evaluated by measuring the competitive inhibition on other protein having binding affinity for CD80 or CD86. For instance, a competitive inhibition assay can be performed where a reference polypeptide, e.g., a native CTLA4 protein (SEQ ID NO: 1), abatacept (SEQ ID NO: 2), belatacept (SEQ ID NO: 3), SEQ ID NOS: 4 or 5, CD28 or a functional equivalent thereof, or a different subject polypeptide as provided herein, is expressed in a host cells, e.g., an immune cell, e.g., a Ramos cell (human Burkitt's lymphoma cell). In some cases, a reference polypeptide is purified and attached to a solid support, like a micro-bead. CD80 or CD86 molecules tagged with a detectable label, e.g., conjugated with biotin or a fluorescent tag, are then incubated with the reference polypeptide expressed by the host cell or attached to the solid support. In some examples, a subject polypeptide is added to the incubation where the subject polypeptide can compete with the reference polypeptide for binding to the detectably labeled CD80 or CD86 molecules. Such competition can be measured by examining the detectably labeled CD80 or CD86 molecules that remains on the surface of the host cell or attached to the solid support. The measurement can be carried out by any technique available to one skilled in the art, depending on the detectably labels used to tag the CD80 or CD86 molecules, for instance, flow cytometry, fluorescence imaging, or fluorescent spectrometry can be used when fluorescent labels are used, while other approaches measuring magnetic forces or electrical impedance can be used when magnetic or electrically conductive labels are used, respectively. In these cases, the relative binding affinity of the subject polypeptide for CD80 or CD86 as compared to the reference polypeptide is inversely proportional to the CD80 or CD86 molecules remaining on the cell surface or attached to the solid support. In other cases, the relative binding affinity of the subject polypeptide for CD80 or CD86 as compared to the reference polypeptide is proportional to the CD80 or CD86 molecules remaining on the cell surface or attached to the solid support, where a subject polypeptide to be tested is expressed by the host cells or attached to the solid support, and a reference polypeptide is used to compete for the binding to CD80 or CD86 molecules. Other formats of the competitive inhibition assay available to one skilled in the art can be used to examine the binding affinity of a subject polypeptide as well. For instance, a luminescent oxygen channeling (LOCI) competition assay, such as described in U.S. Pat. No. 6,251,581 or the variants thereof, e.g., AlphaLISA® competition assay, can be applied to measure the binding affinity of a subject polypeptide.

In some embodiments, a subject polypeptide exhibits immunosuppressive activity. For example, a subject polypeptide can inhibit activation of immune cells, e.g., immune cell proliferation or secretion of cytokines, e.g., IL2.

Different types of assays are available to evaluate the proliferation of cells, comprising but not limited to DNA synthesis cell proliferation assays, metabolic cell proliferation assays, assays detecting proliferation markers and assays measuring ATP concentration. In a DNA synthesis cell proliferation assay, DNA of proliferating cells are labeled to be radioactive, and the label can be washed, adhered to filters and then measured using a scintillation counter. In a metabolic cell proliferation assay, tetrazolium salts such as MTT, XTT, MTS and WSTs may be used which are reduced in metabolically active cells, forming a formazan dye that subsequently changes the color of the media. In an assay detecting proliferation markers, a monoclonal antibody may be used to target common markers for cell proliferation and/or cell cycle regulation such as Ki-67, PCNA, topoisomerase IIB, and phospho-histone H3. For a measurement of ATP concentration, a bioluminescence-based detection of ATP may be used using the enzyme luciferase and its substrate luciferin.

An CFSE (carboxyfluorescein succinimidyl ester) cell-proliferation assay can be used to measure proliferation of lymphocytes and the effect of a subject polypeptide on the proliferation of T cells. CFSE is an effective and popular means to monitor lymphocyte division. CFSE can covalently label long-lived intracellular molecules with the fluorescent dye, carboxyfluorescein. Thus, when a CFSE-labeled cell divides, its progeny are endowed with half the number of carboxyfluorescein-tagged molecules and thus each cell division can be assessed by measuring the corresponding decrease in cell fluorescence, for instance, via flow cytometry or fluorescent imaging. In some cases, primary T cells or immortalized cell lines like Jurkat cells, can be used for this assay upon activation. Other cell proliferation labels, like MTS (3-(4,5-dimethylthiazol-2-yl)-5-(3-carboxymethoxyphenyl)-2-(4-sulfophenyl)-2H-tetrazolium) or BrdU, or measurement techniques, like label-free cell proliferation counting, that are available to one skilled in the art can also be used for examining the inhibitory effect of a subject polypeptide on T cell proliferation, indicative of its immunosuppressive activity.

In some embodiments, a subject polypeptide inhibits proliferation of T cells at least as effectively as a native CTLA4 protein (SEQ ID NO: 1), abatacept (SEQ ID NO: 2), belatacept (SEQ ID NO: 3), or SEQ ID NOS: 4 or 5. In further embodiments, a subject polypeptide inhibits proliferation of T cells at least as effectively as abatacept (SEQ ID NO: 2) or belatacept (SEQ ID NO: 3). In some embodiments, a subject polypeptide as described herein inhibits proliferation of T cells by at least 10%, 20%, 30%, 40%, 50%, 60%, 70%, 80%, 90% or more at a concentration of 0.001-100 μg/mL, 0.01-100 μg/mL, 0.1-100 μg/mL, 1-100 μg/mL, 10-100 μg/mL, 0.01-1 μg/mL, 0.01-10 μg/mL or 0.1-10 μg/mL.

Another aspect of T cells includes production and release of cytokines, like IL2. The immunosuppressive activity of a subject polypeptide can be measured by an assay where IL2 secretion from an activated T cell is measured in the presence of a subject polypeptide. IL2 secretion can be measured by any available techniques in the art, for instance, by ELISA (enzyme-linked immunosorbent assay).

In some embodiments, in either a cell proliferation assay or cytokine production assay, the inhibitory effect of a subject polypeptide can be examined by testing the inhibitory effects of a series of different concentrations of the subject polypeptide. In some embodiments, $IC_{50}$ of a subject polypeptide can be calculated in such assays. In certain embodiments, a subject polypeptide binds to CD80 and/or CD86 and inhibits cell growth, like T cell proliferation, or cytokine production, like IL2 production, at a $IC_{50}$ value ranging from about 0.0001 to 10 times of the $IC_{50}$ of a native CTLA4 protein (SEQ ID NO: 1), abatacept (SEQ ID NO: 2), belatacept (SEQ ID NO: 3), or SEQ ID NOS: 4 or 5. In certain embodiments, a subject polypeptide binds to CD80 and/or CD86 and inhibits cell growth, like T cell proliferation, or cytokine production, like IL2 production, at a $IC_{50}$ value ranging from about 0.0001 to 0.0005 times, from about 0.0005 to 0.001 times, from about 0.001 to 0.002 times, from about 0.002 to 0.005 times, from about 0.005 to 0.0075 times, from about 0.0075 to 0.01 times, from about 0.01 to 0.02 times, from about 0.02 to 0.05 times, from about 0.05 to 0.075 times, from about 0.075 to 0.1 times, from about 0.1 to 0.2 times, from about 0.2 to 0.5 times, from about 0.5 to 0.75 times, from about 0.75 times to 1 time, from about 1 to 5 times, or from about 5 to 10 times of the $IC_{50}$ of a native CTLA4 protein (SEQ ID NO: 1), abatacept (SEQ ID NO: 2), belatacept (SEQ ID NO: 3), or SEQ ID NOS: 4 or 5, or a $IC_{50}$ value within a range of any two of the aforementioned values.

In some embodiments, a subject polypeptide inhibits T cell proliferation at a $IC_{50}$ value ranging from about 0.001 to 0.01 times, from about 0.002 to 0.0075 times, from about 0.0025 to about 0.005 times, or from about 0.003 to 0.004 times of the $IC_{50}$ of abatacept (SEQ ID NO:2). In some embodiments, a subject polypeptide inhibits T cell proliferation at a $IC_{50}$ value ranging from about 0.075 to 0.75 times, from about 0.1 to 0.5 times, or from about 0.2 to about 0.3 times of the $IC_{50}$ of belatacept (SEQ ID NO:3).

In some embodiments, a subject polypeptide inhibits IL2 secretion by T cells at a $IC_{50}$ value ranging from about 0.005 to 0.05 times, from about 0.0075 to 0.025 times, or from about 0.01 to about 0.015 times of the $IC_{50}$ of abatacept (SEQ ID NO:2). In some embodiments, a subject polypeptide inhibits IL2 secretion by T cells at a $IC_{50}$ value ranging from about 0.075 to 0.75 times, from about 0.1 to 0.5 times, or from about 0.2 to about 0.3 times of the $IC_{50}$ of belatacept (SEQ ID NO:3).

Fusion Protein and Other Modifications

In some aspects, the present disclosure provides a polypeptide that is a fusion protein comprising a CTLA4 variant sequence as described herein and a fusion partner sequence.

A fusion partner sequence as provided herein can confer a functional property, including but not limited to, half-life extension, facilitating protein purification and/or manufacturing, enhanced biophysical properties such as increase solubility or stability, and reduced immunogenicity or toxicity, or any other purpose. For example, a subject fusion protein may exhibit extended in vivo half-life, thereby facilitating a less frequent dosing (such as dosing twice per week, once per week, or once every other week, etc.) in a therapeutic regimen. Exemplary subject polypeptides comprise a CTLA4 variant sequence as described herein fused to a fusion partner sequence such as an albumin (e.g., human serum albumin), PK extending (PKE) adnectin, XTEN, Fc domain, or a fragment of any of the foregoing, or a combination of any of the foregoing. A fusion protein can be produced by expressing a nucleic acid which encodes the CTLA4 variant sequence and a fusion partner sequence in the same reading frame, optionally separated by a sequence encoding a linker sequence. The fusion protein may comprise the CTLA4 variant sequence and fusion partner sequence in any order, e.g., one or more fusion partners linked to the N-terminus and/or C-terminus of the CTLA4 variant sequence, or one or more fusion partners linked to both the N-terminus and C-terminus of the CTLA4 variant sequence. The fusion may be formed by attaching a fusion partner to either end (i.e., either the N- or C-terminus) of a CTLA4 variant sequence, i.e., fusion partner-CTLA4 variant or CTLA4 variant-fusion partner arrangements. Additionally, the CTLA4 variant sequence may be fused to one or more fusion partners at both ends, optionally with a linker sequence at either end or both ends.

In some embodiments, the CTLA4 variant sequence may be fused to an immunoglobulin Fc domain ("Fc domain"), or a fragment or variant thereof, such as a functional Fc region. A functional Fc region can bind to FcRn, but does not possess effector function. The ability of the Fc region or fragment thereof to bind to FcRn can be determined by standard binding assays known in the art. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions can be assessed using various assays known in the art for evaluating such antibody effector functions.

In an exemplary embodiment, the Fc domain is derived from an IgG1 subclass, however, other subclasses (e.g., IgG2, IgG3, and IgG4) may also be used. In some embodiments, exemplary sequences of a human IgG1 immunoglobulin Fc domain that can be used in a subject polypeptide include SEQ ID NO: 7 in Table 6 or amino acids 131-357 of SEQ ID NO: 2.

In some embodiments, the Fc region used in the fusion protein may comprise the hinge region of an Fc molecule. An exemplary hinge region comprises the core hinge residues spanning positions 1-16 (i.e., DKTHTCPPCPAPELLG (SEQ ID NO: 83) of the exemplary human IgG1 immunoglobulin Fc domain sequence provided above. In certain embodiments, the fusion protein may adopt a multimeric structure (e.g., dimer) owing, in part, to the cysteine residues at positions 6 and 9 within the hinge region of the exemplary human IgG1 immunoglobulin Fc domain sequence provided above. In some embodiments, the cysteine residues at positions 6 and 9 within the hinge region of the exemplary human IgG1 immunoglobulin Fc domain sequence can be replaced with serine, e.g., amino acids 131-257 of SEQ ID NO: 2. In other embodiments, the hinge region as used herein, may further include residues derived from the $CH_1$ and $CH_2$ regions that flank the core hinge sequence of the exemplary human IgG1 immunoglobulin Fc domain sequence provided above. In yet other embodiments, the hinge sequence may comprise or consist of GSTHTCPPCPAPELLG (SEQ ID NO: 84).

In some embodiments, the hinge sequence may include one or more substitutions that confer desirable pharmacokinetic, biophysical, and/or biological properties. Some exemplary hinge sequences include EPKSSDKTHTCPPCPAPELLGGPS (SEQ ID NO: 85), EPKSSDKTHTCPPCPAPELLGGSS (SEQ ID NO: 86), EPKSSGSTHTCPPCPAPELLGGSS (SEQ ID NO: 87), DKTHTCPPCPAPELLGGPS (SEQ ID NO: 88), and DKTHTCPPCPAPELLGGSS (SEQ ID NO: 89). In one embodiment, the residue P at position 18 of the exemplary human IgG1 immunoglobulin Fc domain sequence provided above may be replaced with S to ablate Fc effector function; this replacement is exemplified in hinges having the sequences EPKSSDKTHTCPPCPAPELLGGSS (SEQ ID NO: 86), EPKSSGSTHTCPPCPAPELLGGSS (SEQ ID NO: 87), and DKTHTCPPCPAPELLGGSS (SEQ ID NO: 89). In another embodiment, the residues DK at positions 1-2 of the exemplary human IgG1 immunoglobulin Fc domain sequence provided above may be replaced with GS to remove a potential clip site; this replacement is exemplified in the sequence EPKSSGSTHTCPPCPAPELLGGSS (SEQ ID NO: 87). In another embodiment, the C at the position 103 of the heavy chain constant region of human IgG1 (i.e., domains $CH_1$-$CH_3$), may be replaced with S to prevent improper cysteine bond formation in the absence of a light chain; this replacement is exemplified in the sequences EPKSSDKTHTCPPCPAPELLGGPS (SEQ ID NO: 85), EPKSSDKTHTCPPCPAPELLGGSS (SEQ ID NO: 86), and EPKSSGSTHTCPPCPAPELLGGSS (SEQ ID NO: 87).

In some embodiments, the Fc domain comprises an amino acid sequence selected from Table 6. In some embodiments, the Fc domain comprises an amino acid sequence having about or greater than 70%, 75%, 80%, 85%, 90%, 95%, 96%, 97%, 98%, 99%, or 99.5% sequence identity to amino acids 125-357 of SEQ ID NO: 2. It should be understood that the C-terminal lysine of an Fc domain is an optional component of a fusion protein comprising an Fc domain. In some embodiments, the Fc domain comprises an amino acid sequence selected from Table 6, except that the C-terminal lysine thereof is omitted.

In some embodiments, a subject polypeptide as provided herein comprises an amino acid sequence with about or greater than 70%, 75%, 80%, 85%, 90%, 95%, 96%, 97%, 98%, 99%, 99.5% or 100% sequence identity to amino acids 1-359 of SEQ ID NO: 6.

In some embodiments, a subject polypeptide comprising a CTLA4 variant sequence fused to an albumin binding sequence is provided. In some embodiments, fusion to serum albumin can increase the half-life of the subject polypeptide or fragment thereof. Exemplary albumin binding sequences include, but are not limited to, the albumin binding domain from streptococcal protein G (see. e.g., Makrides et al., *J Pharmacol. Exp. Ther.* 277:534-542 (1996) and Sjolander et al., *J, Immunol. Methods* 201:115-123 (1997)), or albumin-binding peptides such as those described in, e.g., Dennis, et al., J Biol. Chem. 277:35035-35043 (2002).

In some embodiments, the CTLA4 variant sequences of the present disclosure are fused directly with serum albumin (including but not limited to, human serum albumin). In some embodiments, the CTLA4 variant sequences of the present disclosure are acylated with fatty acids. In some cases, the fatty acids promote binding to serum albumin. See, e.g., Kurtzhals, et al., Biochem. J 312:725-731 (1995). A CTLA4 variant sequence can be produced as a fusion protein comprising human serum albumin (HSA) or a portion thereof. Such fusion constructs may be suitable for enhancing expression of the CTLA4 variant, or fragment thereof, in a eukaryotic host cell, such as CHO, or in a bacterium such as *E. coli*. Exemplary HSA portions include the N-terminal polypeptide (amino acids 1-369, 1-419, and intermediate lengths starting with amino acid 1), as disclosed in U.S. Pat. No. 5,766,883, and PCT publication WO 97/24445, which is incorporated by reference herein. In some embodiments, the fusion protein may comprise a HSA protein with a CTLA4 variant, or fragments thereof, attached to each of the C-terminal and N-terminal ends of the HSA. Exemplary HSA constructs are disclosed in U.S. Pat. No. 5,876,969, which is incorporated by reference herein.

The CTLA4 variant sequence may be fused an XTEN molecule. XTEN molecules are also referred to as unstructured recombinant polymers, unstructured recombinant polypeptides (URPs), and are generally described in Schellenberger et al., Nat Biotechnol., 2009 December; 27 (12): 1186-90, U.S. Pub. No. 2012/0220011, U.S. Pat. No. 7,846,445, and WO/2012/162542, each of which is hereby incorporated by reference in its entirety. The half-life of the CTLA4 variant sequence may be varied by varying the constitution of the XTEN molecule, e.g., by varying its size. For example, an XTEN molecule may be selected in order to achieve a desired half-life, such as in the range of 1 to 50 hours, such as at least 1, 2, 5, 10, 12, 15, 20, or 25 hours, or longer.

In some embodiments, a subject polypeptide comprises a CTLA4 variant sequence fused to an adnectin, e.g. an albumin-binding or PKE adnectin. Exemplary adnectins are disclosed in U.S. Pub. No. 2011/0305663, which is hereby incorporated by reference in its entirety. The adnectin may be based on a tenth fibronectin type III domain and may bind to serum albumin. The adnectin may comprise one or more of a BC loop comprising the amino acid sequence set forth in SEQ ID NO: 45, a DE loop comprising the amino acid sequence set forth in SEQ ID NO: 46, and an FG loop comprising the amino acid sequence set forth in SEQ ID NO: 47, or comprises a polypeptide selected from SEQ ID NO: 48, 49, 50, 51, and 52-72, or comprises a polypeptide at least 60%, at least 70%, at least 75%, at least 80%, at least 85%, at least 90% or at least 95% identical to SEQ ID NO: 48, 49, 50, 51, or 52-72, which respectively correspond to SEQ ID NOS 5, 6, 7, 8, 12, 16, 20, and 24-44 of U.S. Pub. No. 2011/0305663.

In certain embodiments, the fusion partner and CTLA4 variant are fused via a linker sequence. Exemplary linker sequences may comprise or consist of a sequence selected from Table 7, or a combination thereof. Exemplary linker sequences can have lengths of between 0 (i.e., no linker sequence present) and 100 or more amino acids, such as between at least 1, 2, 3, 4, 5, 6, 7, 8, 9, or 10 and up to 60, 50, 40, 30, 29, 28, 27, 26, 25, 24, 23, 22, 21, 20, 19, 18, 17, 16, 15, 14, 13, 12, or 11 amino acids. Exemplary non-limiting lengths of a linker sequence include between 1 and 100 amino acids, 1 and 40 amino acids, between 1 and 20 amino acids, between 1 and 10 amino acids, or between 3 and 5 amino acids in length.

In some embodiments, a subject polypeptide described herein is fused to a polymer, e.g., polyethylene glycol (PEG). A polypeptide or fragment thereof can be pegylated to, for example, increase the biological (e.g., serum) half-life of the polypeptide. To pegylate a polypeptide, the polypeptide typically is reacted with polyethylene glycol (PEG), such as a reactive ester or aldehyde derivative of PEG, under conditions in which one or more PEG groups become attached to the polypeptide. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C1$-$C_{10}$) alkoxy- or aryloxy-polyethylene glycol or polyethylene glycol-maleimide. Methods for pegylating proteins such as those disclosed in for example, EP 0 154 316 by Nishimura et al. and EP 0 401 384 by Ishikawa et al may be used. In some embodiments, a polymer, e.g., PEG, may be covalently attached to a subject polypeptide described herein, either at the N- or C-terminus or at an internal location, using conventional chemical methods, e.g., chemical conjugation. Without being bound by a theory, PEG moieties may contribute to, once attached to the polypeptide as described herein, the water solubility, high mobility in solution, lack of toxicity and low immunogenicity, extended circulating life, increased stability, ready clearance from the body, and altered distribution in the body.

Other half-life extension technologies that may be used to increase the serum half-life of the subject polypeptides, but are not limited to, XTEN (Schellenberger et al., *Nat. Biotechnol.* 27:1186-1192, 2009) and Albu tag (Trussel et al., *Bioconjug Chem.* 20:2286-2292, 2009).

In some aspects, the present disclosure provides a polypeptide comprising a CTLA4 variant sequence with chemical modifications, such as, but not limited to, conjugation, fusion, and attachment chemistry for various functional purposes.

Agents that alter immunologic reactivity of a subject polypeptide can be used to modify the subject polypeptide as provided herein.

In some embodiments, it is preferred to have low immunogenicity for the subject polypeptide. In some embodiments, agents that reduce immunogenicity of the subject polypeptide are used for the modification. Agents that reduce immunologic reactivity include, but are not limited to anti-inflammatory agents and immunosuppressants. Anti-inflammatory agents include non-steroidal anti-inflammatory drugs (NSAIDs) and corticosteroids. NSAIDs include but are not limited to, salicylates, such as acetylsalicylic acid; diflunisal, salicylic acid, and salsalate; propionic acid derivatives, such as ibuprofen; naproxen; dexibuprofen, dexketoprofen, flurbiprofen, oxaprozin, fenoprofen, loxoprofen, and ketoprofen; acetic acid derivatives, such as indomethacin, diclofenac, tolmetin, aceclofenac, sulindac, nabumetone, etodolac, and ketorolac; enolic acid derivatives, such as piroxicam, lornoxicam, meloxicam, isoxicam, tenoxicam, phenylbutazone, and droxicam; anthranilic acid derivatives, such as mefenamic acid, flufenamic acid, meclofenamic acid, and tolfenamic acid; selective COX-2 inhibitors, such as celecoxib, lumiracoxib, rofecoxib, etoricoxib, valdecoxib, firocoxib, and parecoxib; sulfonanilides, such as nimesulide; and others such as clonixin, and licofelone. Corticosteroids include but are not limited to, cortisone, dexamethasone, hydrocortisone, methylprednisolone, prednisone, and prednisolone. The immunosuppressants include but are not limited to hydroxychloroquine, sulfasalazine, leflunomide, etanercept, infliximab, adalimumab, D-penicillamine, oral gold compound, injectable gold compound (intramuscular injection), minocycline, sodium gold thiomalate, auranofin, D-penicillamine, lobenzarit, bucillamine, actarit, cyclophosphamide, azathioprine, methotrexate, mizoribine, cyclosporine, and tacrolimus.

In some embodiments, it is preferred to have high immunogenicity for the subject polypeptide. In some embodiments, agents that increase immunogenicity of the subject polypeptide are used for the modification. Agents that enhance immunologic reactivity include, but are not limited to, bacterial superantigens. Agents that facilitate coupling to a solid support include, but are not limited to, biotin or avidin. Immunogen carriers include, but are not limited to, any physiologically acceptable buffers. Bioresponse modifiers include cytokines, particularly tumor necrosis factor (TNF), interleukin-2, interleukin-4, granulocyte macrophage colony stimulating factor and gamma.-interferons.

Other functional moieties include signal peptides, agents that enhance or reduce immunologic reactivity, agents that facilitate coupling to a solid support, vaccine carriers, bioresponse modifiers, paramagnetic labels and drugs. A signal peptide is a short amino acid sequence that directs a newly synthesized protein through a cellular membrane, usually the endoplasmic reticulum in eukaryotic cells, and either the inner membrane or both inner and outer membranes of bacteria. Signal peptides are typically at the N-terminal portion of a polypeptide and are typically removed enzymatically between biosynthesis and secretion of the polypeptide from the cell. Such a peptide can be incorporated into the subject antibody or fragment thereof to allow secretion of the synthesized molecules.

In some embodiments, a subject polypeptide is conjugated to a chemically functional moiety. Typically, the moiety is a label capable of producing a detectable signal. These conjugated polypeptides thereof are useful, for example, in detection systems such as quantitation of tumor burden, and imaging of metastatic foci and tumor imaging. Such labels are known in the art and include, but are not limited to, radioisotopes, enzymes, fluorescent compounds, chemiluminescent compounds, bioluminescent compounds substrate cofactors and inhibitors. See, for examples of patents describing the use of such labels, U.S. Pat. Nos. 3,817,837; 3,850,752; 3,939,350; 3,996,345; 4,277,437; 4,275,149; and 4,366,241. The moieties can be covalently linked to the subject polypeptide as described herein, recombinantly linked, or conjugated to a subject polypeptide through a secondary reagent, such as an antibody, protein A, or a biotin-avidin complex.

In some embodiments, a subject polypeptide is conjugated to one or more drug moieties. Suitable drug moieties include immunosuppressive agents. Non-limiting examples of immunosuppressive agents that can be conjugated to a subject polypeptide include glucocorticoids, cytostatic agents, antibodies, drugs that act on immunophilins, statins and other agents such as interferons (e.g., INF-β and INF-γ), opioids, TNF binding agents (e.g., infliximab, etanercept, adalimumab, curcumin and catechins), mycophenolate, IL-1 receptor antagonists, and other small molecule agents (e.g., fingolimod, myriocin). Exemplary glucocorticoids include, but are not limited to, hydrocortisone, prednisone, prednisolone, methylprednisone, dexamethasone, betamethasone, triamcinolone, beclometasone, fludrocortisone acetate, deoxycorticosterone acetate, and aldosterone. Exemplary cytostatic agents include but are not limited to cyclophosphamide, nitrosoureas, platinum compounds, methotrexate, azathioprine, mercaptopurine, pyrimidine analogs, protein synthesis inhibitors, and antibiotics such as dactinomycin, anthracyclines, mitomycin C, bleomycin and mithramycin. Exemplary immunosuppressant antibodies include, but are not limited to, anti-CD20 antibodies, anti-IL2 receptor antibodies (daclizumab, basiliximab), Campath-1H, anti-$\alpha_4\beta_1$ integrin antibodies, anti-IL-15 antibodies, anti-IL-6 receptor antibodies, and anti-CD3 antibodies (muromonab). Exemplary agents that act on immunophilins include but are not limited to cyclosporin, tacrolimus, and sirolimus.

In some embodiments, a subject polypeptide is conjugated to an anti-inflammatory agent. Non-limiting examples of anti-inflammatory agents include non-steroidal anti-inflammatoires such as ibuprofen, aspirin, naproxen, diflunisal, ketoprofen, nabumetone, piroxicam, diclofenac, indomethacin, sulindac, tolmetin, etodolac, ketorolac, oxaprozin, and celecoxib, and glucocorticoids, which also have immunosuppressive activity.

In some embodiments, a subject polypeptide is conjugated to an antineoplastic agent. Non-limiting examples are radioisotopes, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

In some embodiments, a subject polypeptide is conjugated to a toxin, e.g., an immunotoxin. A variety of immunotoxins can be used in the subject compositions. Suitable immunotoxins can be found, for example, in Monoclonal Antibody-toxin Conjugates: Aiming the Magic Bullet, Thorpe et al. (1982) Monoclonal Antibodies in Clinical Medicine, Academic Press, pp. 168-190; Vitatta (1987) Science 238:1098-1104; and Winter and Milstein (1991) Nature 349:293-299. Suitable toxins include, but are not limited to, ricin, radionuclides, pokeweed antiviral protein, Pseudomonas exotoxin A, diphtheria toxin, ricin A chain, fungal toxins such as restrictocin and phospholipase enzymes. See, generally, "Chimeric Toxins," Olsnes and Pihl, Pharmac. Ther. 15:355-381 (1981); and "Monoclonal Antibodies for Cancer Detection and Therapy," eds. Baldwin and Byers, pp. 159-179, 224-266, Academic Press (1985).

The chemically functional moieties can be made recombinantly for instance by creating a fusion gene encoding the subject polypeptide and the functional moiety. Alternatively, the subject polypeptide can be chemically bonded to the moiety by any of a variety of well-established chemical procedures. For example, when the moiety is a protein, a variety of coupling agents may be used such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). The linker may be a "cleavable linker" facilitating release of the cytotoxic drug in the cell. For example, an acid-labile linker, peptidase-sensitive linker, dimethyl linker, or disulfide-containing linker (Chari et al. Cancer Research, 52:127-131 (1992)) may be used. The moieties may be covalently linked, or conjugated, through a secondary reagent, such as an antibody, protein A, or a biotin-avidin complex.

In some embodiments, a subject polypeptide as provided herein is bispecific as it can have two different binding domain, with one being the domain capable of binding to CD80 or CD86 specifically and the other being capable of binding to a different molecule. In other embodiments, a subject polypeptide is specific for more than two different molecules besides CD80 and CD86.

Production of Polypeptide

In one aspect, provided herein is a polynucleotide encoding a polypeptide of the present disclosure. Other aspects of the present disclosure also provide a vector comprising a polynucleotide sequence encoding a polypeptide as described herein. In some aspects, host cells expressing a polypeptide as described herein are also provided.

A subject polypeptide can be produced as a recombinant polypeptide by cloning DNA encoding the subject polypeptide, integrating the clone into a suitable vector, and transducing the vector into host cells. Alternatively, the polynucleotide encoding a polypeptide of the disclosure can be synthesized in part or completely. In some cases, a subject polypeptide is a fusion protein, the nucleic acid encoding the fusion partner sequence, e.g., an immunoglobulin constant region, can be obtained by amplification and modification of germline DNA or cDNA encoding the desired fusion protein, for example using the polymerase chain reaction (PCR). In some embodiments, a nucleic acid encoding wild-type abatacept can be synthesized and used as a template for mutagenesis to generate a subject polypeptide as described herein using routine mutagenesis techniques; alternatively, a nucleic acid encoding the variant can be directly synthesized.

In some embodiments, a polynucleotide as provided herein comprises a nucleic acid sequence coding for CTLA4 variant that is operatively linked to another nucleic acid sequence encoding another protein, e.g., a fusion partner, such as an antibody constant region and/or a flexible linker sequence. The term "operatively linked," as used in this context, is intended to mean that the two nucleic acids are joined such that the amino acid sequences encoded by the two nucleic acids remain in-frame.

The nucleotide sequences encoding a polypeptide of the present disclosure may also be modified, for example, polynucleotides encoding the subject polypeptide can be subjected to codon optimization to achieve optimized expression of a subject polypeptide in a desired host cell. For example, in one method of codon optimization, a native codon is substituted by the most frequent codon from a reference set of genes, wherein the rate of codon translation for each amino acid is designed to be high. Additional exemplary methods for generating codon optimized polynucleotides for expression of a desired protein, which can be applied to the CTLA4 variant sequence and/or the fusion partner sequence of the polypeptide of the present disclosure, are described in Kanaya et al., Gene, 238:143-155 (1999), Wang et al., Mol. Biol. Evol., 18 (5): 792-800 (2001), U.S. Pat. No. 5,795,737, U.S. Publication 2008/0076161 and WO 2008/000632.

Polynucleotides of the present disclosure include those coding for functional equivalents and fragments thereof of the exemplified polypeptides. Functional equivalents may be polypeptides having conservative amino acid substitutions, analogs including fusions, and mutants.

Where desired, the recombinant polynucleotides may comprise heterologous sequences that facilitate detection of the expression and purification of the gene product. Examples of such sequences include those encoding reporter proteins such as β-galactosidase, β-lactamase, chloramphenicol acetyltransferase (CAT), luciferase, green fluorescent protein (GFP) and their derivatives. Other heterologous sequences that facilitate purification may code for epitopes such as Myc, HA (derived from influenza virus hemagglutinin), His-6 (SEQ ID NO: 90), FLAG, or the Fc portion of immunoglobulin, glutathione S-transferase (GST), and maltose-binding protein (MBP).

The polynucleotides can be conjugated to a variety of chemically functional moieties as described above. Commonly employed moieties include labels capable of producing a detectable signal, signal peptides, agents that enhance or reduce immunologic reactivity, agents that facilitate coupling to a solid support, vaccine carriers, bioresponse modifiers, paramagnetic labels and drugs. The moieties can be covalently linked to a polynucleotide recombinantly or by other means known in the art.

The polynucleotides can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable in accordance with any of the various embodiments described herein.

The polynucleotides can be obtained using chemical synthesis, recombinant cloning methods, PCR, or any combination thereof. One of skill in the art can use the sequence data provided herein to obtain a desired polynucleotide by employing a DNA synthesizer or ordering from a commercial service.

Polynucleotides comprising a desired sequence can be inserted into a suitable vector which in turn can be introduced into a suitable host cell for replication, amplification and expression. Accordingly, in one aspect, provided herein are a variety of vectors comprising one or more of the polynucleotides of the present disclosure. Also provided is a selectable library of expression vectors comprising at least one vector encoding the subject polypeptide.

Vectors of the present disclosure are generally categorized into cloning and expression vectors. Cloning vectors are useful for obtaining replicate copies of the polynucleotides they contain, or as a means of storing the polynucleotides in a depository for future recovery. Expression vectors (and host cells containing these expression vectors) can be used to obtain polypeptides produced from the polynucleotides they contain. In some embodiments, a subject polypeptide is a fusion protein, the expression vector can already carry fusion partner sequences, e.g., antibody constant region sequences. For example, one approach to converting a protein of the disclosure comprising only a CTLA4 variant sequence into a subject fusion protein is to insert the nucleic acid encoding the CTLA4 variant sequence into expression vectors already encoding immunoglobulin Fc such that the CTLA4 variant-encoding sequence is operatively linked to the Fc-encoding sequence within the vector. Additionally or alternatively, the recombinant expression vector can encode a signal peptide that facilitates secretion of the CTLA4 protein from a host cell. The nucleic acid encoding a CTLA4 protein can be cloned into the vector such that the signal peptide is linked in-frame to the amino terminus of the CTLA4 protein-encoding nucleic acid. The signal peptide can be a CTLA4 signal peptide or a heterologous signal peptide, e.g., an immunoglobulin signal peptide. Suitable cloning and expression vectors include any known in the art, e.g., those for use in bacterial, mammalian, yeast, insect and phage display expression systems.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pBR322, pMB9, ColEl, pCR1, RP4, pUC18, mp18, mp19, phage DNAs (including filamentous and non-filamentous phage DNAs), and shuttle vectors such as pSA3 and pAT28. These and other cloning vectors are available from commercial vendors such as Clontech, Bio-Rad, Stratagene, and Invitrogen.

Expression vectors containing subject polynucleotides are useful to obtain host vector systems to produce proteins and polypeptides. Typically, these expression vectors are replicable in the host organisms either as episomes or as an integral part of the chromosomal DNA. Suitable expression vectors for the subject polypeptide include plasmids, viral vectors, including phagemids, adenoviruses, adeno-associated viruses, retroviruses, cosmids, etc. A number of expression vectors suitable for expression in eukaryotic cells including yeast, avian, and mammalian cells are available. One example of an expression vector is pcDNA3 (Invitrogen, San Diego, Calif.), in which transcription is driven by the cytomegalovirus (CMV) early promoter/enhancer. Two types of particularly useful expression vectors for expressing the subject polypeptide as described herein are the phage display vector and bacterial display vector.

It is possible to express a subject polypeptide of the disclosure in either prokaryotic or eukaryotic host cells. A host cell strain can be chosen which modulates the expression of the inserted sequences, or modifies and processes the gene product in the specific fashion desired. Such modifications (e.g., glycosylation) and processing (e.g., cleavage) of protein products can be important for the function of the subject polypeptide. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERY, BHK, Hela, COS, MDCK, 293, 3T3, W138, BT483, Hs578T, HTB2, BT20 and T47D, NSO (a murine myeloma cell line that does not endogenously produce any immunoglobulin chains), CRL7030 and HsS78Bst cells.

For long-term, high-yield production of recombinant proteins, stable expression is preferred. For example, cell lines which stably express a subject polypeptide can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the subject polypeptide.

Once a subject polypeptide molecule has been produced by recombinant expression, it can be purified by any suitable method for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the subject polypeptides can be fused to heterologous polypeptide sequences provided herein or otherwise known in the art to facilitate purification. For example, a subject polypeptide can be purified through recombinantly adding a poly-histidine tag (His-tag), FLAG-tag, hemagglutinin tag (HA-tag) or myc-tag among others that are commercially available and utilizing suitable purification methods.

Method of Treatment

In another aspect, provided herein are methods of using the subject polypeptide to treat conditions, diseases or disorders, e.g., inflammatory disorders, autoimmune diseases, cancer, or transplant rejection.

In some embodiments, the present disclosure provides a method of treating an inflammatory disorder in a mammal in need thereof, comprising administering to the mammal a therapeutically effective amount of a subject polypeptide of the present disclosure. In some cases, the inflammatory disorder is multiple sclerosis. In other cases, the inflammatory disorder is an autoimmune disease. Examples of autoimmune diseases include but are not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, inflammatory bowel disease (IBD), juvenile idiopathic arthritis (JIA), psoriatic arthritis, systemic lupus erythematosus (SLE), asthma, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In further embodiments, a subject polypeptide of the present disclosure is used for the treatment of bursitis, lupus, acute disseminated encephalomyelitis (ADEM), Addison's disease, antiphospholipid antibody syndrome (APS), aplastic anemia, autoimmune hepatitis, coeliac disease, Crohn's disease, diabetes mellitus (type 1), Goodpasture's syndrome, graves' disease, Guillain-Barré syndrome (GBS), Hashimoto's disease, inflammatory bowel disease, lupus erythematosus, myasthenia gravis, opsoclonus myoclonus syndrome (OMS), optic neuritis, Ord's thyroiditis, osteoarthritisostheoarthritis, uveoretinitis, pemphigus, polyarthritis, primary biliary cirrhosis, Reiter's syndrome, Takayasu's arteritis, temporal arteritis, warm autoimmune hemolytic anemia, Wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

In still further embodiments, the present disclosure provides a method of treating cancer in a mammal in need thereof, comprising administering to the mammal a therapeutically effective amount of a subject polypeptide of the present disclosure. In some cases, the cancer is hepatocellular carcinoma. In other cases, the cancer is acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related (e.g. Lymphoma and Kaposi's Sarcoma) or Viral-Induced cancer.

In some embodiments, a subject polypeptide of the present disclosure is used for the treatment of infection, endotoxic shock associated with infection, arthritis, rheumatoid arthritis, psoriatic arthritis, systemic onset juvenile idiopathic arthritis (JIA), systemic lupus erythematosus (SLE), asthma, pelvic inflammatory disease, Alzheimer's Disease, Crohn's disease, ulcerative colitis, irritable bowel syndrome, Castleman's disease, ankylosing spondylitis, dermatomyositis, uveitis, Peyronie's Disease, coeliac disease, gallbladder disease, Pilonidal disease, peritonitis, psoriasis, vasculitis, surgical adhesions, stroke, Type I Diabetes, Lyme arthritis, meningoencephalitis, immune mediated inflammatory disorders of the central and peripheral nervous system, autoimmune disorders, pancreatitis, trauma from surgery, graft-versus-host disease, transplant rejection, heart disease, bone resorption, burns patients, myocardial infarction, Paget's disease, osteoporosis, sepsis, liver/lung fibrosis, periodontitis, hypochlorhydria, solid tumors (renal cell carcinoma), prostatic and bladder cancers, pancreatic cancer, neurological cancers, and B-cell malignancies (e.g., Castleman's disease, certain lymphomas, chronic lymphocytic leukemia, and multiple myeloma).

In some embodiments, the subject to be treated is a mammal, such as a human. In other cases, the mammal is a mouse, a rat, a cat, a dog, a rabbit, a pig, a sheep, a horse, a bovine, a goat, a gerbil, a hamster, a guinea pig, a monkey or any other mammal. Many such mammals may be subjects that are known to the art as preclinical models for certain diseases or disorders, including inflammatory diseases, solid tumors and/or other cancers (e.g., Talmadge et al., 2007 Am. J. Pathol. 170:793; Kerbel, 2003 Canc. Biol. Therap. 2 (4 Suppl 1): S134; Man et al., 2007 Canc. Met. Rev. 26:737; Cespedes et al., 2006 Clin. TransL Oncol. 8:318).

In another aspect, the disclosure provides methods of using a subject polypeptide of the present disclosure to treat diseases, conditions or disorders in a mammal in conjunction with a second agent. The second agent could be administered together with, before, or after the subject polypeptide.

In some embodiments, the second agent is an immunosuppressant. The immunosuppressants that can be used in combination with the subject polypeptide include but are not limited to hydrocortisone, prednisone, prednisolone, methylprednisone, dexamethasone, betamethasone, triamcinolone, beclometasone, fludrocortisone acetate, deoxycorticosterone acetate, aldosterone, cyclophosphamide, nitrosoureas, platinum compounds, methotrexate, azathioprine, mercaptopurine, pyrimidine analogs, protein synthesis inhibitors, dactinomycin, anthracyclines, mitomycin C, bleomycin, mithramycin, rapamycin, cyclosporin, tacrolimus, sirolimus, mycophenolic acid, mizoribine, 15-deoxyspergualin, mycophenolate mofetil (MMF), anti-thymocyte globulin, an anti-CD20 antibody or derivative, analog or antigen binding fragment thereof, an anti-IL2 receptor antibody (daclizumab, basiliximab) or a derivative, analog or antigen binding fragment thereof, Campath-1H, an anti-$\alpha_4\beta_1$ integrin antibody or a derivative, analog or antigen binding fragment thereof, an anti-IL-15 antibody or a derivative, analog or antigen binding fragment thereof, an anti-IL-6 receptor antibody or a derivative, analog or antigen binding fragment thereof, an anti-CD3 antibody (muromonab) or a derivative, analog or antigen binding fragment thereof, an anti-MHC antibody, or a derivative, analog or antigen binding fragment thereof, an anti-CD2 antibody, or a derivative, analog or antigen binding fragment thereof, an anti-CD4 antibody, or a derivative, analog or antigen binding fragment thereof, an anti-CD11a/CD 18 antibody, or a derivative, analog or antigen binding fragment thereof, an anti-CD7 antibody, or a derivative, analog or antigen binding fragment thereof, an anti-CD27 antibody, or a derivative, analog or antigen binding fragment thereof, an anti-CD80 and/or anti-CD86 antibody (e.g., ATCC HB-253, ATCC CRL-2223, ATCC CRL-2226, ATCC HB-301, ATCC HB-11341, etc), or a derivative, analog or antigen binding fragment thereof, an anti-CD40 antibody (e.g., ATCC HB-9110), or a derivative, analog or antigen binding fragment thereof, or a derivative, analog or antigen binding fragment thereof, an anti-CD45 antibody, or a derivative, analog or antigen binding fragment thereof, an anti-CD58 antibody, or a derivative, analog or antigen binding fragment thereof, an anti-CD137 antibody, or a derivative, analog or antigen binding fragment thereof, an anti-ICOS antibody, or a derivative, analog or antigen binding fragment thereof, an anti-CD150 antibody, or a derivative, analog or antigen binding fragment thereof, an anti-OX40 antibody, or a derivative, analog or antigen binding fragment thereof, an anti-4-1BB antibody, or a derivative, analog or antigen binding fragment thereof, and low molecular weight adhesion antagonists such as LFA-1 antagonists, selectin antagonists and VLA-4 antagonists.

In some embodiments, the subject polypeptide can be used in combination with other immunomodulatory compounds such as, but are not limited to, soluble gp39 (also known as CD40 ligand (CD40L), CD154, T-BAM, TRAP), soluble CD29, soluble CD40, soluble CD80 (e.g., ATCC 68627), soluble CD86, soluble CD28 (e.g., 68628), soluble CD56, soluble Thy-1, soluble CD3, soluble TCR, soluble VLA-4, soluble $VCAM^{-1}$, soluble $LECAM^{-1}$, soluble $ELAM^{-1}$, soluble CD44, antibodies reactive with gp39 (e.g., ATCC HB-10916, ATCC HB-12055 and ATCC HB-12056), antibodies reactive with CD28 (e.g., ATCC HB-11944 or mAb 9.3 as described by Martin et al. (J. Clin. Immun. 4 (1): 18-22, 1980), antibodies reactive with LFA-1 (e.g., ATCC HB-9579 and ATCC TIB-213), antibodies reactive with LFA-2, antibodies reactive with IL-12, antibodies reactive with IFN-γ, antibodies reactive with CD48, antibodies reactive with any ICAM (e.g., ICAM-1 (ATCC CRL-2252), ICAM-2 and ICAM-3), antibodies reactive with CTLA4 (e.g., ATCC HB-304), antibodies reactive with Thy-1, antibodies reactive with CD56, antibodies reactive with CD29, antibodies reactive with TCR, antibodies reactive with VLA-4, antibodies reactive with $VCAM^{-1}$, antibodies reactive with $LECAM^{-1}$, antibodies reactive with $ELAM^{-1}$, antibodies reactive with CD44.

In some embodiments, the second agent is an antiviral agent. Antiviral agents include but are not limited to telaprevir, boceprevir, semiprevir, sofosbuvir, daclastavir, asunaprevir, lamivudine, adefovir, entecavir, tenofovir, telbivudine, interferon alpha and PEGylated interferon alpha. In other embodiments, the second agent is an agent that acts to relieve the symptoms of inflammatory conditions described herein. Anti-inflammatory agents include non-steroidal anti-inflammatory drugs (NSAIDs) and corticosteroids. NSAIDs include but are not limited to, salicylates, such as acetylsalicylic acid; diflunisal, salicylic acid, and salsalate; propionic acid derivatives, such as ibuprofen; naproxen; dexibuprofen, dexketoprofen, flurbiprofen, oxaprozin, fenoprofen, loxoprofen, and ketoprofen; acetic acid derivatives, such as indomethacin, diclofenac, tolmetin, aceclofenac, sulindac, nabumetone, etodolac, and ketorolac; enolic acid derivatives, such as piroxicam, lornoxicam, meloxicam, isoxicam, tenoxicam, phenylbutazone, and droxicam; anthranilic acid derivatives, such as mefenamic acid, flufenamic acid, meclofenamic acid, and tolfenamic acid; selective COX-2 inhibitors, such as celecoxib, lumiracoxib, rofecoxib, etoricoxib, valdecoxib, firocoxib, and parecoxib; sulfonanilides, such as nimesulide; and others such as clonixin, and licofelone. Corticosteroids include but are not limited to, cortisone, dexamethasone, hydrocortisone, methylprednisolone, prednisone, and prednisolone.

In further embodiments, the second agent is an anti-cancer agent (e.g. a chemotherapeutic agent). The chemotherapeutic can be selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples of chemotherapeutic agents, cytotoxic agents, and non-peptide small molecules include Gleevec® (Imatinib Mesylate), Velcade® (bortezomib), Casodex® (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex®), raloxifene, aromatase inhibiting 4 (5)-imidazoles, 4-hydroxytamoxifen, trioxifene, keoxifene, LY 117018, onapristone, and toremifene (Fareston®); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; (CPT-11); camptothecin-11 topoisomerase inhibitor RFS 2000; difluoromethylornithine (DMFO). Where desired, the subject polypeptide can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

The specific dose will vary depending on the particular polypeptide chosen, the dosing regimen to be followed, whether it is administered in combination with other agents, timing of administration, the tissue to which it is administered, and the physical delivery system in which it is carried. In some embodiments, a subject polypeptide is administered to a subject within a range of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 mg per week on average over the course of a treatment cycle. For example, the subject polypeptide is administered to a subject within a range of about 35, 36, 37, 38, 39, 40, 41, 42, 43, 44, 45, 46, 47, 48, 49, 50, 51, 52, 53, 54, or 55 mg per week. In some embodiments, the subject polypeptide is administered to a subject within a range of about 40, 41, 42, 43, 44, 45, 46, 47, 48, 49, 50, 51, 52, 53, 54, or 55 mg per week.

In some embodiments, a subject polypeptide is administered to a subject in an amount greater than 1, 1.5, 2, 2.5, 3, 3.5, 4, 4.5, 5, 5.5, 6, 6.5, 7, 7.5, 8, 8.5, 9, 9.5, or 10 mg per day on average over the course of a treatment cycle. For example, the subject polypeptide is administered to a subject in an amount between about 6 and 10 mg, between about 6.5 and 9.5 mg, between about 6.5 and 8.5 mg, between about 6.5 and 8 mg, or between about 7 and 9 mg per day on average over the course of a treatment cycle.

In some embodiments, a subject polypeptide is administered to a subject within a range of about 0.01 mg/kg-50 mg/kg per day, such as about, less than about, or more than about, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, or 50 mg/kg per day. In some embodiments, a subject polypeptide is administered to a subject within a range of about 0.1 mg/kg-400 mg/kg per week, such as about, less than about, or more than about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 100 mg/kg, 150 mg/kg, 200 mg/kg, 250 mg/kg, 300 mg/kg, 350 mg/kg, or 400 mg/kg per week. In some embodiments, a subject polypeptide is administered to a subject within a range of about 0.4 mg/kg-1500 mg/kg per month, such as about, less than about, or more than about 0.4 mg/kg, 0.5 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 100 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, or 1000 mg/kg per month. In some embodiments, a subject polypeptide is administered to a subject within a range of about 0.1 $mg/m^2$-200 $mg/m^2$ per week, such as about, less than about, or more than about 1 $mg/m^2$, 5 $mg/m_2$, 10 $mg/m_2$, 15 $mg/m_2$, 20 $mg/m_2$, 25 $mg/m_2$, 30 $mg/m_2$, 35 $mg/m_2$, 40 $mg/m_2$, 45 $mg/m^2$, 50 $mg/m^2$, 55 $mg/m^2$, 60 $mg/m^2$, 65 $mg/m^2$, 70 $mg/m^2$, 75 $mg/m^2$, 100 $mg/m^2$, 125 $mg/m^2$, 150 $mg/m^2$, 175 $mg/m^2$, or 200 $mg/m^2$ per week. The target dose may be administered in a single dose. Alternatively, the target dose may be administered in about or more than about 1, 2, 3, 4, 5, 6, 7, 8, 9, 10, 11, 12, 13, 14, 15, 16, 17, 18, 19, 20, 25, 30, or more doses. For example, a dose of about 1 mg/kg per week may be delivered weekly at a dose of about 1 mg/kg every week, about 2 mg/kg administered every two weeks, or about 4 mg/kg administered every four weeks over the course of the week. The administration schedule may be repeated according to any regimen as described herein, including any administration schedule described herein. In some embodiments, a subject polypeptide is administered to a subject in the range of about 0.1 $mg/m^2$-500 $mg/m^2$, such as about, less than about, or more than about 1 $mg/m^2$, 5 $mg/m^2$, 10 $mg/m^2$, 15 $mg/m^2$, 20 $mg/m^2$, 25 $mg/m^2$, 30 $mg/m^2$, 35 $mg/m^2$, 40 $mg/m^2$, 45 $mg/m^2$, 50 $mg/m^2$, 55 $mg/m^2$, 60 $mg/m^2$, 65 $mg/m^2$, 70 $mg/m^2$, 75 $mg/m^2$, 100 $mg/m^2$, 130 $mg/m^2$, 135 $mg/m^2$, 155 $mg/m^2$, 175 $mg/m^2$, 200 $mg/m^2$, 225 $mg/m^2$, 250 $mg/m^2$, 300 $mg/m^2$, 350 $mg/m^2$, 400 $mg/m^2$, 420 $mg/m^2$, 450 $mg/m^2$, or 500 $mg/m^2$.

A dose of the subject polypeptide may be about, at least about, or at most about 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 mg or mg/kg, or any range derivable therein. It is contemplated that a dosage of mg/kg refers to the mg amount of the subject polypeptide per kg of total body weight of the subject. It is contemplated that when multiple doses are given to a patient, the doses may vary in amount or they may be the same.

Pharmaceutical Composition

In another aspect, provided herein are pharmaceutical compositions comprising the subject polypeptide and a pharmaceutically acceptable carrier, excipient, or stabilizer including but not limited to inert solid diluents and fillers, diluents, sterile aqueous solution and various organic solvents, permeation enhancers, solubilizers and adjuvants. (Remington's Pharmaceutical Sciences 16$^{th}$ edition, Osol, A. Ed. (1980)).

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. Suitable examples of sustained release preparations include semipermeable matrices of solid hydrophobic polymers containing the subject polypeptide, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. Some sustained release formulations enable release of molecules over a few weeks to a few months, or even up to a few years. In some embodiments, the subject pharmaceutical composition release the subject polypeptide as described herein for at least a few weeks, such as for at least 1 week, 2 weeks, 3 weeks or 4 weeks. In further embodiments, the subject pharmaceutical composition release the subject polypeptide as described herein over a few months, such as for at least 1 month, 2 months, 3 months, 4 months, 5 months, or 6 months.

The pharmaceutical composition may be in unit dosage forms suitable for single administration of precise dosages. The pharmaceutical composition can further comprise a subject polypeptide as an active ingredient and may include a conventional pharmaceutical carrier or excipient. Further, it may include other medicinal or pharmaceutical agents, carriers, adjuvants, etc.

Exemplary parenteral administration forms include solutions or suspensions of active polypeptide and/or PEG-modified polypeptide in sterile aqueous solutions, for example, aqueous propylene glycol or dextrose solutions. Such dosage forms can be suitably buffered with salts such as histidine and/or phosphate, if desired.

In some embodiments, the disclosure provides a pharmaceutical composition for injection containing a subject polypeptide and a pharmaceutical excipient suitable for injection. Example components and amounts of agents in such compositions are as described herein.

The forms in which the compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline can be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions can be prepared by incorporating a subject polypeptide of the present disclosure or functional fragment thereof in the desired amount in the appropriate solvent with various other ingredients as enumerated above, followed by filtered sterilization. Generally, dispersions are prepared by incorporating the various sterilized active ingredients into a sterile vehicle which contains the basic dispersion medium and other ingredients. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some embodiments, the disclosure provides a pharmaceutical composition for oral administration containing a subject polypeptide of the present disclosure or a functional fragment thereof, and a pharmaceutical excipient suitable for oral administration.

In some embodiments, a solid pharmaceutical composition for oral administration is provided herein containing: (i) an effective amount of a subject polypeptide of the present disclosure or a functional fragment thereof; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition is a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, and typically include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

This disclosure further encompasses anhydrous pharmaceutical compositions and dosage forms comprising an active ingredient, since water can facilitate the degradation of some polypeptides. For example, water may be added (e.g., 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. Pharmaceutical compositions and dosage forms which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A subject polypeptide of the present disclosure can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides;

succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG $10^{-100}$ nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition includes a solubilizer to ensure good solubilization and/or dissolution of the compound and to minimize precipitation of the compound. This can be especially advantageous for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ¿-caprolactone and isomers thereof, 8-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In another aspect of the disclosure, provided are kits comprising the unit doses containing the subject polypeptide compositions of the disclosure and instructions for use. The kit can further comprise one or more unit doses containing one or more additional reagents, such as an immunosuppressive reagent, a cytotoxic agent or a radiotoxic agent as described above, or one or more additional therapeutic proteins as described herein (e.g., an antibody). Kits typically include a label indicating the intended use of the contents of the kit. The term label includes any writing, or recorded material supplied on or with the kit, or which otherwise accompanies the kit.

A kit of the present disclosure may also include diagnostic agents and/or other therapeutic agents. In one embodiment, a kit includes a subject polypeptide of the present disclosure and a diagnostic agent that may be used in a diagnostic method for diagnosing the state or existence of a disease, condition or disorder in a subject as described herein.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Binding Affinity Assay

All SPR measurements were performed on a Biacore™ _3000 instrument (GE Biosciences, Piscataway, N.J.). Biacore™ Software-Biacore™ 3000 Control Software V3.2 was used for the operation and control of the Biacore™ 3000 instrument. BiaEvaluation Software V4.1 was used for the analysis of SPR data from the Biacore™ 3000 instrument and data was plotted using GraphPad Prism® Software Version 5. The binding affinity of CTLA4 variants to CD80 or CD86 was measured in HBS-EP buffer (10 mM HEPES, 150 mM NaCl, 3.4 mM EDTA, 0.005% P20) at 25° C. The flow rate for the affinity study was 30 μL/minute. The indicated CTLA4 variants were used as the ligand for the construction of the reference channel of the chip. Analyte (CD80/CD86) binding to the immobilized ligand was measured and the concentration of the sIL-6R is from 1.2 to 100 nM (3× dilution). Each sample was injected for 3 min at a flow rate of 30 μL/min to allow for binding to chip-bound peptide. Next, binding buffer without analyte was sent over the chip at the same flow rate to allow for dissociation of bound analyte. After 500s, remaining bound analyte was removed by injecting regeneration solution (1M Formic acid). Data was analyzed by using the Kinetics Wizard and the manual fitting programs that are both included with the BiaEvaluation Software V4.1. $k_a$ is on-rate; $k_d$ is off-rate; $K_D$ is equilibrium dissociation constant; and Relative affinity is calculated as $K_D$ (abatacept)/$K_D$ (variant). The $k_a$, $k_d$, $K_D$ and the affinity relative to Abatacept (sample 70 # or $10^3$ #) are shown in Tables 1-1, 1-2, 1-3, 1-4, 1-5, 1-6, 1-7, and 1-8.

All SPR measurements were performed on a Biacore™ 3000 instrument (GE Biosciences, Piscataway, N.J.).

TABLE 1-1

CD80 Binding Affinity of Exemplary CTLA4-Ig Variants

| Variant | $k_a$ (1/Ms) | $k_d$ (1/s) | $K_D$ (M) | Relative affinity |
|---|---|---|---|---|
| Abatacept (WT) | 2.85E+05 | 6.01E−03 | 2.11E−08 | 1.00 |
| Belatacept | 2.48E+05 | 3.19E−04 | 1.28E−09 | 16.48 |
| 71# | 1.44E+05 | 1.08E−03 | 7.49E−09 | 2.82 |
| 73# | 1.51E+05 | 8.55E−04 | 5.67E−09 | 3.72 |
| 75# | 2.55E+05 | 2.01E−04 | 7.87E−10 | 26.81 |
| 77# | 1.26E+05 | 2.72E−03 | 2.15E−08 | 0.98 |
| 80# | 1.85E+05 | 6.98E−03 | 3.78E−08 | 0.56 |
| 81# | 7.14E+04 | 1.58E−03 | 2.21E−08 | 0.95 |
| 82# | 6.32E+05 | 1.53E−02 | 2.42E−08 | 0.87 |
| 84# | 3.89E+05 | 2.35E−03 | 6.04E−09 | 3.49 |
| 86# | 4.71E+05 | 1.49E−02 | 3.15E−08 | 0.67 |
| 87# | 2.18E+05 | 9.99E−03 | 4.58E−08 | 0.46 |
| 88# | 6.38E+05 | 1.36E−02 | 2.13E−08 | 0.99 |
| 89# | 2.96E+05 | 1.16E−03 | 3.91E−09 | 5.40 |
| 93# | 4.60E+05 | 1.73E−02 | 3.76E−08 | 0.56 |

TABLE 1-2

CD86 Binding Affinity of Exemplary CTLA4-Ig Variants

| Variant | $k_a$ (1/Ms) | $k_d$ (1/s) | $K_D$ (M) | Relative affinity |
|---|---|---|---|---|
| Abatacept (WT) | 2.41E+05 | 6.33E−02 | 2.63E−07 | 1.00 |
| Belatacept | 4.73E+05 | 4.86E−03 | 1.03E−08 | 25.53 |
| 71# | 3.43E+05 | 4.87E−03 | 1.42E−08 | 18.52 |
| 73# | 3.11E+06 | 1.33E−01 | 4.27E−08 | 6.16 |
| 75# | 5.08E+05 | 2.58E−03 | 5.07E−09 | 51.87 |
| 77# | 2.59E+06 | 8.47E−02 | 3.27E−08 | 8.04 |
| 80# | 2.27E+05 | 1.77E−02 | 7.81E−08 | 3.37 |
| 81# | 6.77E+05 | 1.77E−02 | 2.62E−08 | 10.04 |
| 82# | 2.82E+05 | 2.76E−02 | 9.78E−08 | 2.69 |
| 84# | 2.38E+06 | 1.38E−01 | 5.78E−08 | 4.55 |
| 86# | 6.31E+05 | 2.17E−01 | 3.44E−07 | 0.76 |
| 87# | 6.39E+05 | 2.17E−01 | 3.39E−07 | 0.78 |
| 88# | 2.41E+05 | 2.42E−01 | 1.00E−06 | 0.26 |
| 89# | 6.05E+05 | 4.62E−02 | 7.64E−08 | 3.44 |
| 93# | 2.20E+05 | 1.15E−01 | 5.23E−07 | 0.50 |

TABLE 1-3

CD80 Binding Affinity of Exemplary CTLA4-Ig Variants

| Variant | $k_a$ (1/Ms) | $k_d$ (1/s) | $K_D$ (M) | Relative affinity |
|---|---|---|---|---|
| Abatacept (WT) | 6.89E+05 | 7.33E−03 | 1.07E−08 | 1.00 |
| Belatacept | 2.96E+05 | 4.16E−04 | 1.41E−09 | 7.59 |
| 71# | 3.19E+05 | 6.70E−04 | 2.10E−09 | 5.10 |
| 75# | 2.13E+05 | 1.67E−04 | 7.86E−10 | 13.61 |
| 82# | 2.98E+05 | 1.57E−03 | 5.26E−09 | 2.03 |
| 95# | 2.02E+05 | 7.41E−05 | 3.67E−10 | 29.15 |
| 96# | 2.53E+05 | 4.27E−04 | 1.69E−09 | 6.33 |
| 98# | 1.34E+05 | 2.31E−03 | 1.73E−08 | 0.62 |
| 99# | 3.59E+05 | 6.43E−04 | 1.79E−09 | 5.98 |
| 100# | 3.99E+05 | 1.02E−03 | 2.55E−09 | 4.20 |

TABLE 1-4

CD86 Binding Affinity of Exemplary CTLA4-Ig Variants

| Variant | $k_a$ (1/Ms) | $k_d$ (1/s) | $K_D$ (M) | Relative affinity |
|---|---|---|---|---|
| Abatacept (WT) | 9.98E+05 | 8.27E−02 | 8.28E−08 | 1.00 |
| Belatacept | 7.81E+05 | 8.60E−03 | 1.10E−08 | 7.53 |
| 71# | 5.99E+05 | 5.33E−03 | 8.90E−09 | 9.30 |
| 75# | 5.17E+05 | 3.99E−03 | 7.72E−09 | 10.73 |

TABLE 1-4-continued

CD86 Binding Affinity of Exemplary CTLA4-Ig Variants

| Variant | $k_a$ (1/Ms) | $k_d$ (1/s) | $K_D$ (M) | Relative affinity |
|---|---|---|---|---|
| 82# | 7.52E+05 | 6.69E−03 | 8.90E−09 | 9.30 |
| 95# | 9.35E+05 | 1.15E−02 | 1.23E−08 | 6.73 |
| 96# | 3.55E+06 | 5.39E−02 | 1.52E−08 | 5.45 |
| 98# | 2.22E+06 | 1.10E−01 | 4.94E−08 | 1.68 |
| 99# | 4.93E+10 | 5.52E+02 | 1.12E−08 | 7.39 |
| 100# | 6.94E+05 | 8.48E−03 | 1.22E−08 | 6.79 |

TABLE 1-5

CD80 Binding Affinity of Exemplary CTLA4-Ig Variants

| Variant | $k_a$ (1/Ms) | $k_d$ (1/s) | $K_D$ (M) | Relative affinity |
|---|---|---|---|---|
| Abatacept (WT) | 5.19E+05 | 1.55E−03 | 2.99E−09 | 1.00 |
| Belatacept | 4.52E+05 | 1.10E−04 | 2.44E−10 | 12.25 |
| 75# | 3.80E+05 | 2.26E−05 | 5.95E−11 | 50.25 |
| 95# | 3.80E+05 | 1.95E−05 | 5.15E−11 | 58.06 |
| 96# | 4.03E+05 | 9.02E−05 | 2.24E−10 | 13.35 |
| 112# | 3.48E+05 | 4.24E−05 | 1.22E−10 | 24.51 |
| 117# | 2.87E+05 | 1.81E−04 | 6.31E−10 | 4.74 |
| 118# | 3.24E+05 | 4.24E−05 | 1.31E−10 | 22.82 |
| 120# | 3.89E+05 | 5.04E−05 | 1.30E−10 | 23 |
| 121# | 3.39E+05 | 2.66E−05 | 7.85E−11 | 38.09 |
| 122# | 3.31E+05 | 1.41E−05 | 4.25E−11 | 70.35 |
| 124# | 3.54E+05 | 7.43E−05 | 2.10E−10 | 14.24 |
| 127# | 4.11E+05 | 6.78E−05 | 1.65E−10 | 18.12 |
| 131# | 3.47E+05 | 1.95E−05 | 5.62E−11 | 53.20 |
| 132# | 2.85E+05 | 1.21E−04 | 4.25E−10 | 7.03 |
| 133# | 3.38E+05 | 2.28E−05 | 6.74E−11 | 44.36 |
| 134# | 3.22E+05 | 2.99E−05 | 9.30E−11 | 32.15 |
| 135# | 3.15E+05 | 6.94E−04 | 2.20E−09 | 1.36 |
| 136# | 3.34E+05 | 3.82E−04 | 1.14E−09 | 2.62 |
| 137# | 3.49E+05 | 7.20E−04 | 2.07E−09 | 1.44 |
| 141# | 8.83E+05 | 1.78E−02 | 2.02E−08 | 0.15 |

TABLE 1-6

CD86 Binding Affinity of Exemplary CTLA4-Ig Variants

| Variant | $k_a$ (1/Ms) | $k_d$ (1/s) | $K_D$ (M) | Relative affinity |
|---|---|---|---|---|
| Abatacept (WT) | 8.38E+06 | 5.86E−02 | 6.99E−09 | 1.00 |
| Belatacept | 6.70E+05 | 1.80E−03 | 2.70E−09 | 2.59 |
| 75# | 4.57E+05 | 3.19E−04 | 6.99E−10 | 10.00 |
| 95# | 5.80E+05 | 3.49E−03 | 6.02E−09 | 1.16 |
| 96# | 6.63E+05 | 3.02E−03 | 4.55E−09 | 1.54 |
| 112# | 4.14E+05 | 3.47E−04 | 8.39E−10 | 8.33 |
| 117# | 5.04E+05 | 2.36E−03 | 4.68E−09 | 1.49 |
| 118# | 3.85E+05 | 2.92E−04 | 7.58E−10 | 9.22 |
| 120# | 6.70E+05 | 2.74E−03 | 4.09E−09 | 1.71 |
| 121# | 5.66E+05 | 2.59E−03 | 4.58E−09 | 1.53 |
| 122# | 5.54E+05 | 2.29E−03 | 4.13E−09 | 1.69 |
| 124# | 6.54E+05 | 3.24E−03 | 4.95E−09 | 1.41 |
| 127# | 6.95E+05 | 2.96E−03 | 4.25E−09 | 1.64 |
| 131# | 4.11E+05 | 2.90E−04 | 7.05E−10 | 9.91 |
| 132# | 4.34E+05 | 1.17E−04 | 2.70E−10 | 25.89 |
| 133# | 3.60E+05 | 1.79E−04 | 4.97E−10 | 14.06 |
| 134# | 6.42E+05 | 2.79E−03 | 4.35E−09 | 1.61 |
| 135# | 1.47E+07 | 2.37E−01 | 1.62E−08 | 0.43 |
| 136# | 1.56E+06 | 1.81E−02 | 1.16E−08 | 0.60 |
| 137# | 1.83E+06 | 1.13E−02 | 6.19E−09 | 1.13 |
| 141# | 5.96E+05 | 8.16E−03 | 1.37E−08 | 0.51 |

TABLE 1-7

| CD80 Binding Affinity of Exemplary CTLA4-Ig Variants | | | | |
|---|---|---|---|---|
| Variant | $k_a$ (1/Ms) | $k_d$ (1/s) | $K_D$ (M) | Relative affinity |
| Abatacept (WT) | 5.86E+05 | 1.17E−03 | 2.00E−09 | 1.00 |
| Belatacept | 4.56E+05 | 1.35E−04 | 2.95E−10 | 6.78 |
| 133# | 3.56E+05 | 3.02E−05 | 8.49E−11 | 23.56 |
| 142# | 3.48E+05 | 2.31E−05 | 6.64E−11 | 30.12 |

TABLE 1-8

| CD86 Binding Affinity of Exemplary CTLA4-Ig Variants | | | | |
|---|---|---|---|---|
| Variant | $k_a$ (1/Ms) | $k_d$ (1/s) | $K_D$ (M) | Relative affinity |
| Abatacept (WT) | 1.69E+06 | 1.56E−02 | 9.25E−09 | 1.00 |
| Belatacept | 1.13E+06 | 1.07E−03 | 9.42E−10 | 9.82 |
| 133# | 4.04E+05 | 1.61E−04 | 4.00E−10 | 23.12 |
| 142# | 3.47E+05 | 1.22E−05 | 3.53E−11 | 262.04 |

Example 2: Determination of pH Dependence of the Binding Affinity for CD80 and CD86

SPR measurements at pH 7.4 and pH 6.0 were performed in parallel and $K_D$ values calculated according to the protocol as detailed in Example 1. The pH dependence was calculated as the ratio between the $K_D$ value at pH 6.0 and the $K_D$ value at pH 7.4, which indicates the fold of affinity decrease from the pH7.4 to pH6.0. If the pH dependence of a subject variant described herein is over 1, it means that the variant binds to CD80 or CD86 in such a pH-dependent manner that its binding to CD80 or CD86 at pH7.4 is higher than at pH6.0. If the pH dependence of a subject variant described herein is lower than 1, it means that the variant binds to CD80 or CD86 in such a pH-dependent manner that its binding to CD80 or CD86 at pH6.0 is higher than at pH7.4. SPR measurements were performed on exemplary variants 133 # and 142 #, and Abatacept and Belatacept were used as references. The $K_D$ values obtained are provided below in Tables 2-1 and 3-1, respectively. pH dependence thus determined by comparing the binding affinity at pH 7.4 and that at pH 6.0 is provided in Tables 2-2 and 3-2, respectively. As shown in Tables 2-2 and 3-2, exemplary variants 133 # and 142 #both showed higher pH dependence for CD80 and CD86 affinity binding than Abatacept, indicating a more significant decrease in binding affinity from pH7.4 to pH6.0; exemplary variant 133 #showed higher pH dependence for CD80 and Cd86 affinity binding than Belatacept; and exemplary variant 142 #showed a much higher pH dependence for CD86 affinity binding than both Abatacept and Belatacept. These date indicate superior properties of these exemplary CTLA4-Ig variants in terms of antigen neutralization and clearance.

TABLE 2-1

| CD80 Binding Affinity of Exemplary CTLA4-Ig Variants | | | | | | |
|---|---|---|---|---|---|---|
| Variant | pH 7.4 | | | pH 6.0 | | |
| Experiment 6 | $k_a$ (1/Ms) | $k_d$ (1/s) | $K_D$ (M) | $k_a$ (1/Ms) | $k_d$ (1/s) | $K_D$ (M) |
| Abatacept (WT) | 5.86E+05 | 1.17E−03 | 2.00E−09 | 9.99E+05 | 5.26E−03 | 5.26E−09 |
| Belatacept | 4.56E+05 | 1.35E−04 | 2.95E−10 | 5.45E+05 | 5.06E−04 | 9.29E−10 |
| 133# | 3.56E+05 | 3.02E−05 | 8.49E−11 | 3.19E+05 | 1.07E−04 | 3.35E−10 |
| 142# | 3.48E+05 | 2.31E−05 | 6.64E−11 | 3.02E+05 | 6.04E−05 | 2.00E−10 |

TABLE 2-2

| pH Dependence for CD80 Binding Affinity of Exemplary CTLA4 Variants | |
|---|---|
| Variant | pH dependence (Fold of affinity decrease) |
| Abatacept (WT) | 2.63 |
| Belatacept | 3.15 |
| 133# | 3.94 |
| 142# | 3.01 |

TABLE 3-1

| CD86 Binding Affinity of Exemplary CTLA4-Ig Variants | | | | | | |
|---|---|---|---|---|---|---|
| Variant | pH 7.4 | | | pH 6.0 | | |
| Experiment 6 | $k_a$ (1/Ms) | $k_d$ (1/s) | $K_D$ (M) | $k_a$ (1/Ms) | $k_d$ (1/s) | $K_D$ (M) |
| Abatacept (WT) | 1.69E+06 | 1.56E−02 | 9.25E−09 | 1.34E+08 | 1.00E+00 | 7.50E−09 |
| Belatacept | 1.13E+06 | 1.07E−03 | 9.42E−10 | 1.55E+06 | 4.07E−03 | 2.62E−09 |
| 133# | 4.04E+05 | 1.61E−04 | 4.00E−10 | 4.45E+05 | 1.33E−03 | 2.99E−09 |
| 142# | 3.47E+05 | 1.22E−05 | 3.53E−11 | 3.71E+05 | 6.36E−04 | 1.72E−09 |

TABLE 3-2 pH Dependence for CD86 Binding Affinity of Exemplary CTLA4 Variants

| Variant | pH dependence (Fold of affinity decrease) |
|---|---|
| Abatacept (WT) | 0.81 |
| Belatacept | 2.78 |
| 133# | 7.48 |
| 142# | 48.72 |

Example 3: Evaluation of Relative Binding Affinity

Figure 2A:
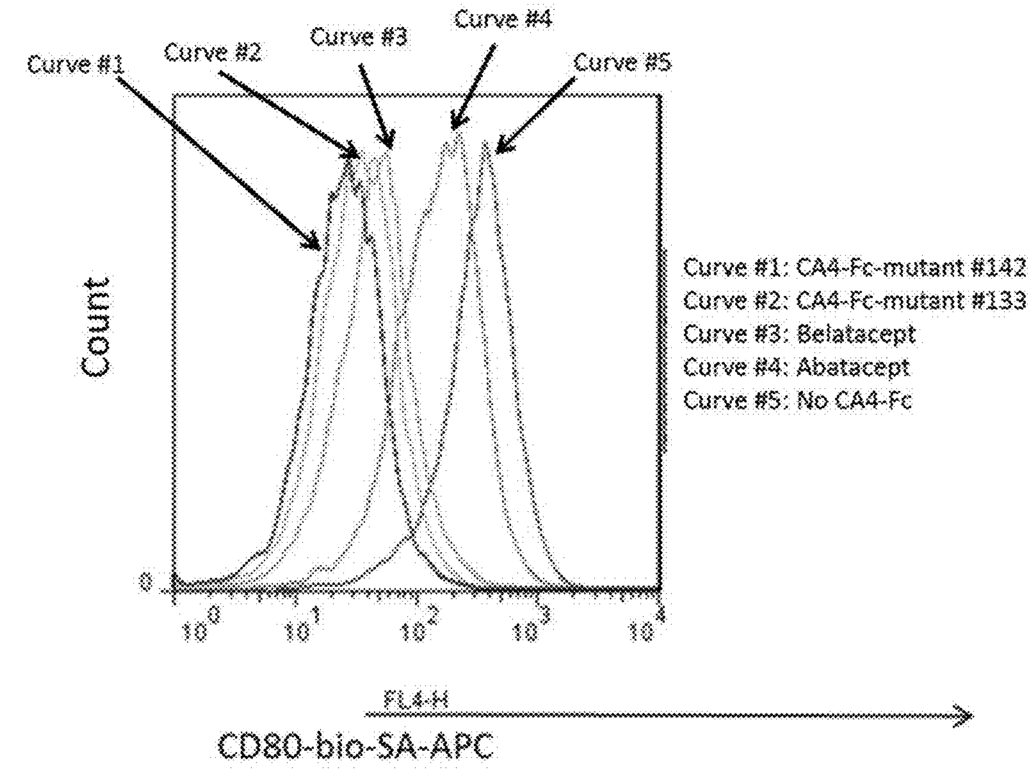
FIGS. 2A and 2B show representative results of a competitive binding assay for an exemplary polypeptide, demonstrating its relative binding affinity for CD80 and CD86, respectively.
Figure 2B:
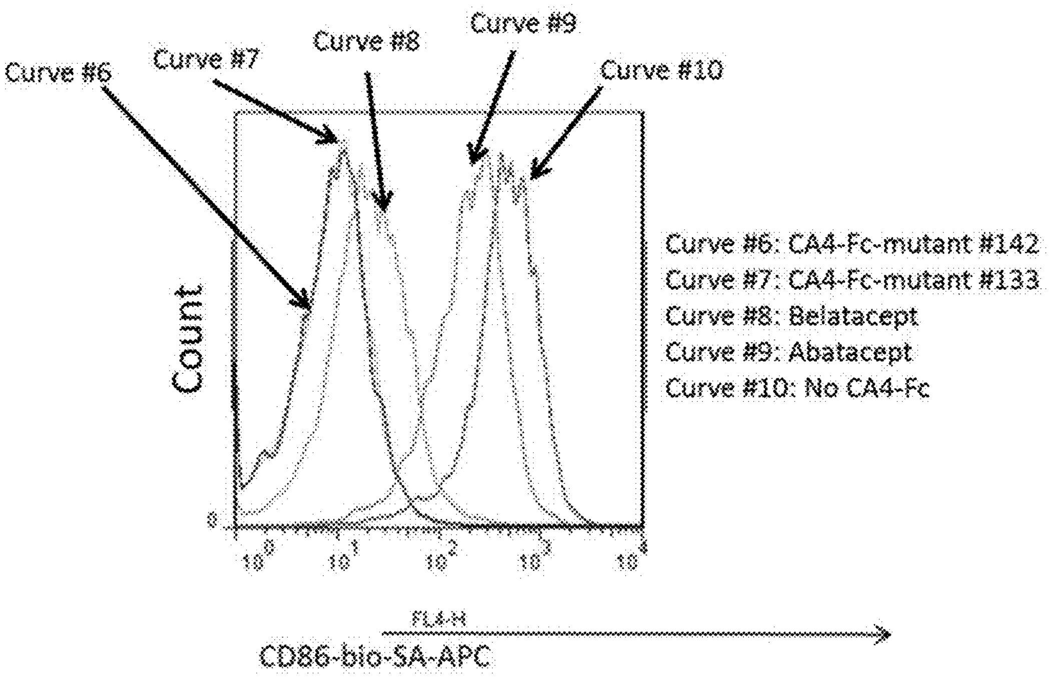

Exemplary CTLA4-Ig variants were examined by a competitive inhibition assay for their binding affinity for CD80 and CD86. In this competitive inhibition assay, Abatacept (WT CTLA4-Ig) construct was transfected into Ramos cells (human Burkitt's lymphoma cells) and Abatacept was expressed and presented on the cell surface of Ramos cells. As shown in FIG. 1, the Ramos cells expressing Abatacept were then incubated with biotin-conjugated CD80 or CD86, which could be bound by Abatacept expressed on the cell surface. Exemplary CTLA4-Ig variants or reference variants (e.g., Abatacept or Belatacept) were then added to the incubated cells. The competition between the later-added exemplary CTLA4-Ig variant and the surface-presented Abatacept for binding to CD80-biotin or CD86-biotin will lead to a portion of the surface-bound CD80-biotin or CD86-biotin to fall off the cell surface. The amount of the CD80-biotin or CD86-biotion that falls off the cell surface can be proportional to the binding affinity of the exemplary variant for CD80 or CD86 relative to Abatacept. As a result, the amount of CD80-biotin or CD86-biotin that remains on the cell surface is inversely proportional to the relative binding affinity of the exemplary variant. The amount of cell surface-bound CD80 or CD86 was examined by flow cytometry after incubating the cells with streptavidin-APC and indicated by the fluorescent signal level brought by the cell surface-bound APC dye. As shown in FIGS. 2A and 2B, the lower the fluorescent signal, the higher the binding affinity of the exemplary variant for CD80 or CD86 as examined. For instance, exemplary variants, mutants 142 #(as demonstrated by curves #1 and #6 in FIGS. 2A and 2B, respectively) and 133 #(curves #2 and #7), showed higher affinity for CD80 and CD86 as compared to Abatacept (curves #4 and #9) and Belatacept (curves #3 and #8).

Example 4: Evaluation of Relative Binding Affinity

Figure 3A:
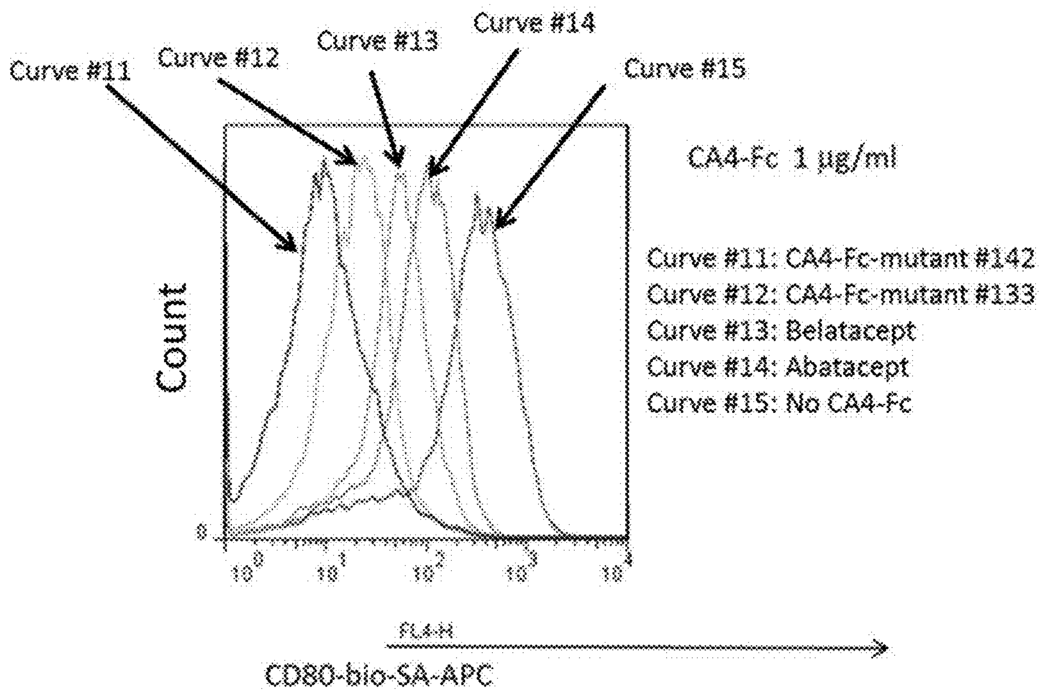
FIGS. 3A and 3B show representative results of another competitive binding assay for an exemplary polypeptide, demonstrating its relative binding affinity for CD80 and CD86, respectively.
Figure 3B:
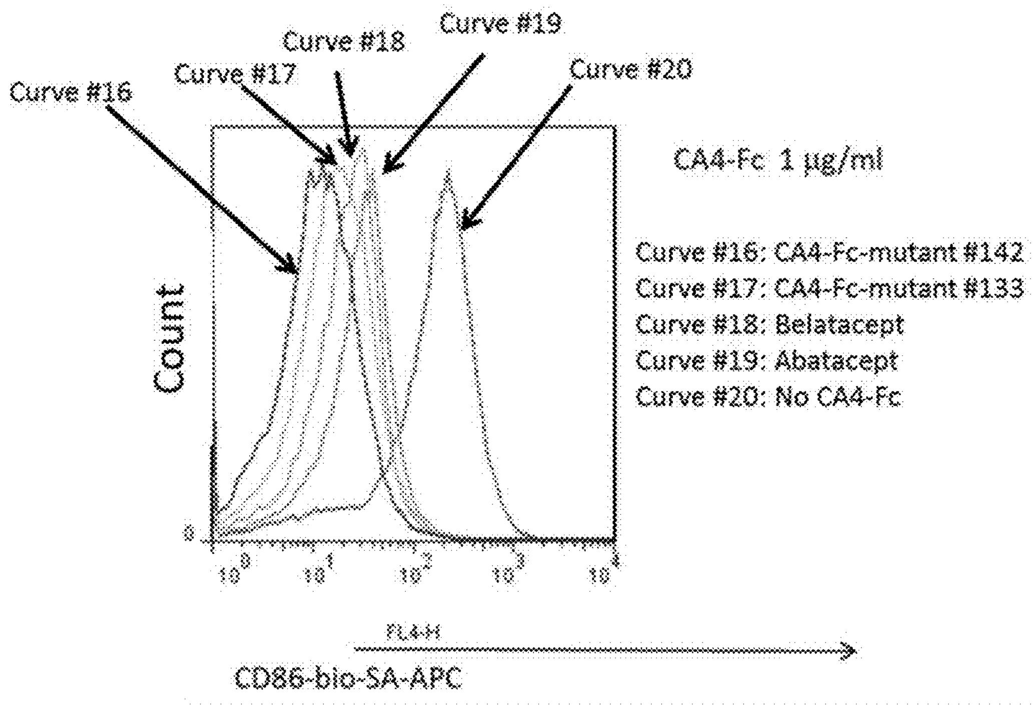

Exemplary CTLA4-Ig variants were examined by a different competitive inhibition assay for their binding affinity for CD80 and CD86. In this competitive inhibition assay, CD28-Ig construct was transfected into Ramos cells (human Burkitt's lymphoma cells) and CD28-Ig was expressed and presented on the cell surface of Ramos cells. Since CD28 can be a key co-stimulatory receptor in T cell activation, it can have natural binding affinity for CD80 and CD86. The Ramos cells expressing CD28-Ig were then incubated with biotin-conjugated CD80 or CD86, which could be bound by CD28-Ig expressed on the cell surface. Exemplary CTLA4-Ig variants or reference variants (e.g., Abatacept or Belatacept) were then added to the incubated cells. The competition between the later-added exemplary CTLA4-Ig variant and the surface-presented CD28 for binding to CD80-biotin or CD86-biotin will lead to a portion of the surface-bound CD80-biotin or CD86-biotin to fall off the cell surface. The amount of the CD80-biotin or CD86-biotion that falls off the cell surface can be proportional to the binding affinity of the exemplary variant for CD80 or CD86 relative to CD28. As a result, the amount of CD80-biotin or CD86-biotin that remains on the cell surface is inversely proportional to the relative binding affinity of the exemplary variant. The amount of cell surface-bound CD80 or CD86 was examined by flow cytometry after incubating the cells with streptavidin-APC and indicated by the fluorescent signal level brought by the cell surface-bound APC dye. As shown in FIGS. 3A and 3B, the lower the fluorescent signal, the higher the binding affinity of the exemplary variant for CD80 or CD86 as examined. For instance, exemplary variants, mutants 142 #(as demonstrated by curves #11 and #16 in FIGS. 3A and 3B, respectively) and 133 #(curves #12 and #17), showed higher affinity for CD80 and CD86 as compared to Abatacept (curves #14 and #19) and Belatacept (curves #13 and #8).

Example 5: Evaluation of Immunosuppressive Effect on T Cell Proliferation

Figure 4:
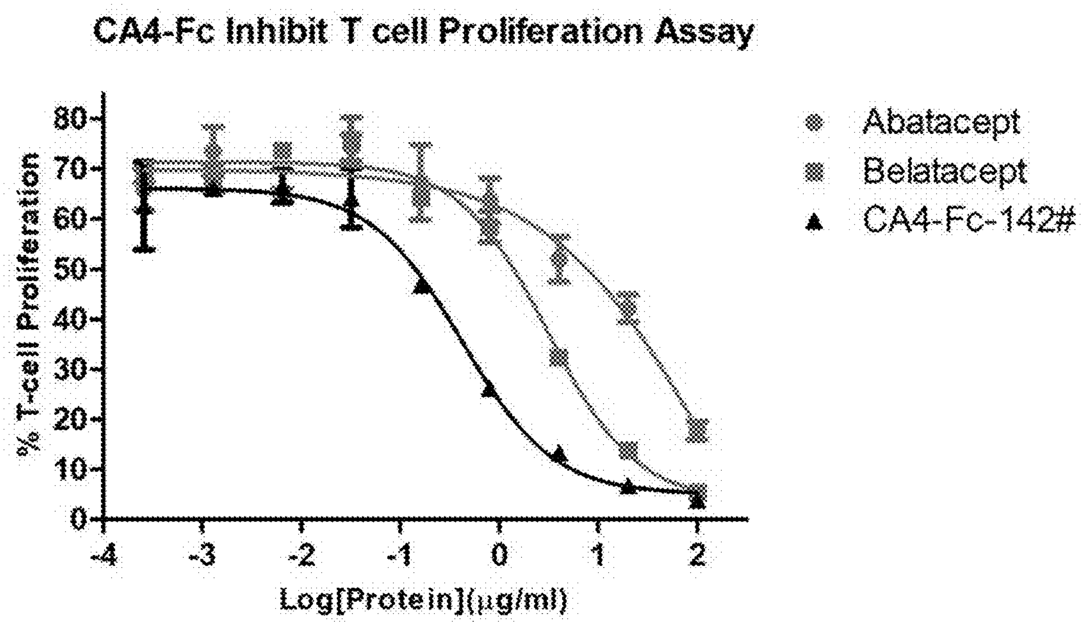
FIG. 4 shows representative results of a T cell proliferation assay for an exemplary polypeptide, demonstrating its inhibitory effect on T cell proliferation.

The immunosuppressive effect of exemplary CTLA4-Ig variants was examined in an assay in which the inhibitory effect of exemplary CTLA4-Ig on primary T cell proliferation was tested. In the experiments, T cells were isolated from healthy human peripheral blood mononuclear cells (PBMC) and were labeled by a fluorescent staining dye carboxyfluorescein succinimidyl ester (CFSE), which was used to trace cell proliferation. The isolated primary T cells were stimulated by anti-CD3 antibody OKT3 and CD86-Fc that were coated on the surface of the cell culture dish. Different concentrations of Abatacept or exemplary CTLA4-Ig variants were added to the T cell culture, which could inhibit the proliferation of the T cells. After 4 days of culture at 37° C., the T cells were subject to flow cytometry analysis of their proliferation. The half maximum inhibitory concentration ($IC_{50}$) was calculated for each tested exemplary variant and Abatacept, as shown in FIG. 4.

Example 6: Evaluation of Immunosuppressive Effect on IL2 Secretion

Figure 5:
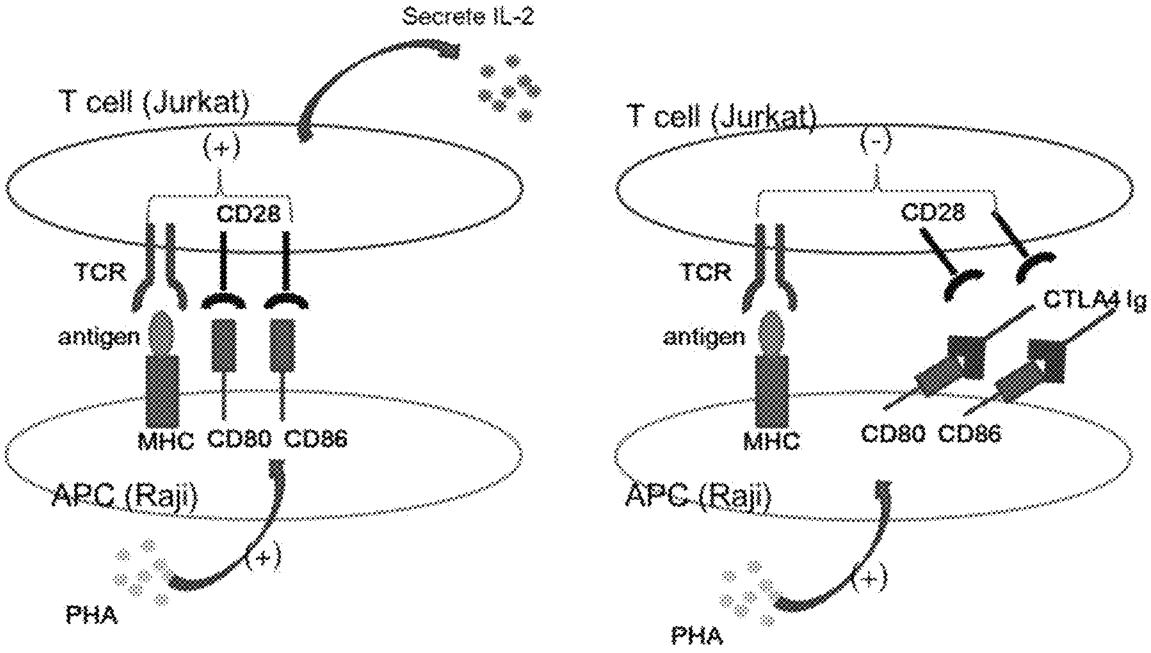
FIG. 5 illustrates the principle of an assay for examining inhibitory effect of exemplary polypeptides on IL-2 secretion from T cells upon immune stimulation.
Figure 6A:
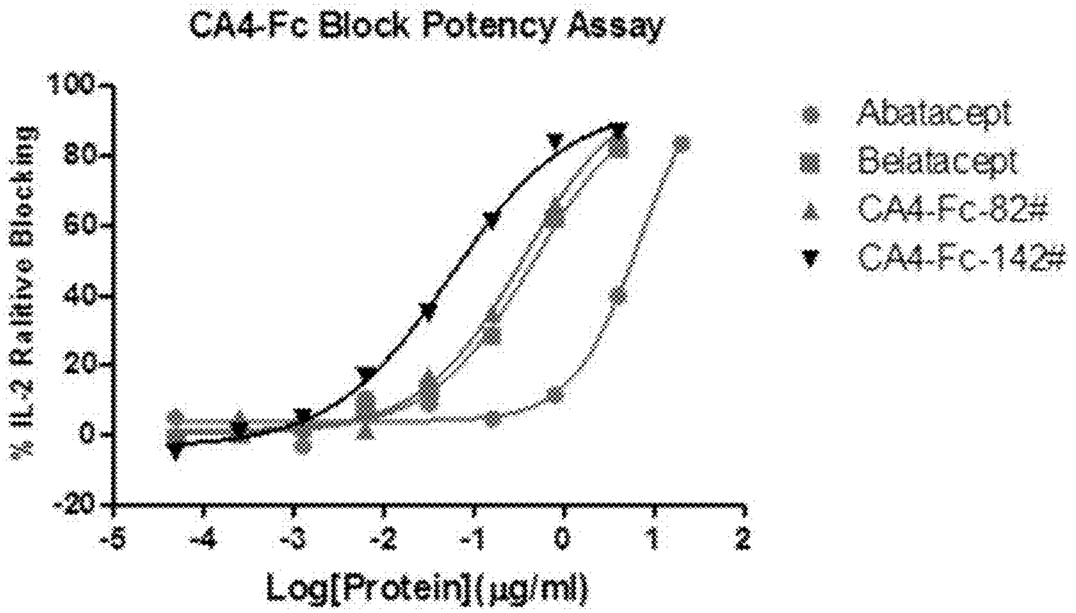
FIGS. 6A-6C show representative results of an IL-2 secretion assay for an exemplary polypeptide, demonstrating its inhibitory effect on IL-2 secretion from T cells upon immune stimulation.
Figure 6B:
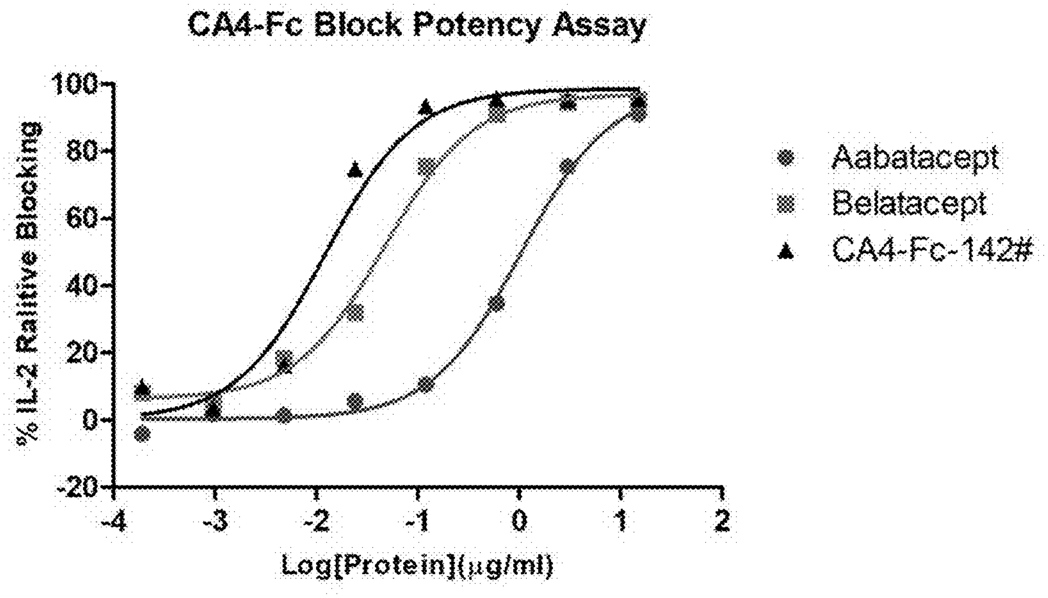
Figure 6C:
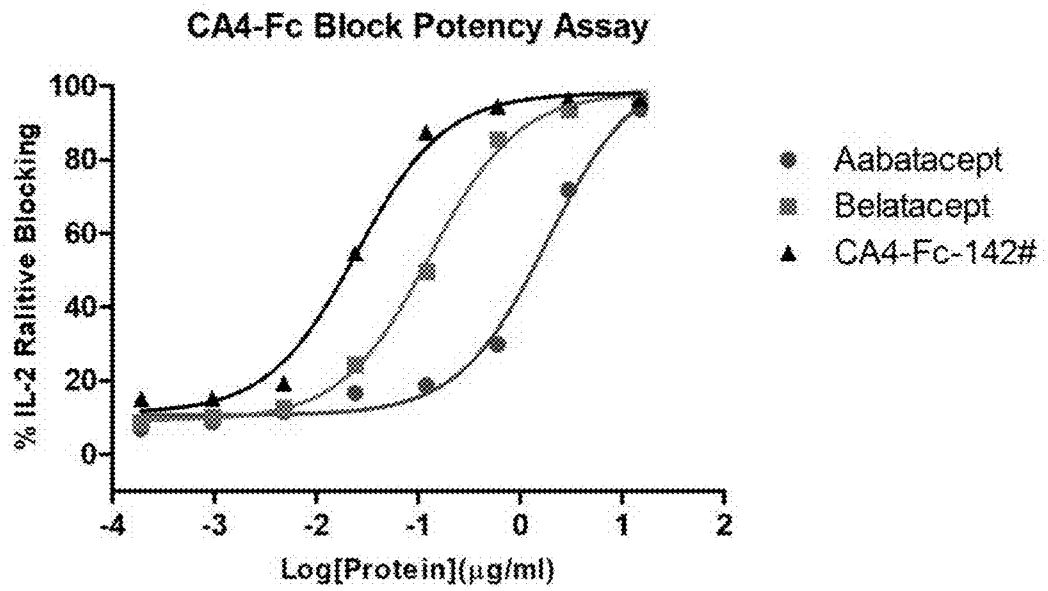

The immunosuppressive effect of exemplary CTLA4-Ig variants was examined in an assay in which the inhibitory effect of exemplary CTLA4-Ig on IL12 secretion of T cells was tested. Raji cells (human B-lymphocytes) can express CD80 and CD86 on the surface. Jurkat cells (human T-lymphocytes) can activate its surface receptor CD28 when stimulated by PHA (Phytohaemagglutinin P). Therefore, as depicted in FIG. 5, in the presence of PHA, co-cultured Raji cells and Jurkat cells can have their surface CD28 and CD80/CD86 bound together, which can lead to activation of Jurkat cells and secretion of IL2 from the activated Jurkat cells. In the experiments, Jurkat cells and Raji cells were co-cultured in the presence of PHA, and different concentrations of Abatacept or exemplary CTLA4-Ig variants were added to the co-culture, which could inhibit the activation of Jurkat cells and thus IL2 secretion, as illustrated in FIG. 5. The higher the immunosuppressive activity of the exemplary variant, the lower level IL2 is detected at. IL2 secretion was examined by ELISA after 24 hour stimulation of 5 μg/mL PHA. $IC_{50}$ was calculated for each tested exemplary variant and Abatacept, as shown in FIGS. 6A-6C. More test results of exemplary polypeptides are shown in Table 4.

TABLE 4

| IC$_{50}$ of Exemplary Polypeptides on IL2 secretion | | | |
|---|---|---|---|
| Variant # | IC50 (μg/mL) | IC50 normalized to Abatacept | IC50 normalized to Belatacept |
| Test I | | | |
| Abatacept | 2.695 | 1 | — |
| Belatacept | 0.1473 | — | 1 |
| 71 | 0.6652 | 0.246827458 | 4.515953836 |
| 73 | 0.4865 | 0.180519481 | 3.302783435 |
| 82 | 0.2115 | 0.078478664 | 1.435845214 |
| 99 | 1.6671 | 0.618589981 | 11.31771894 |
| 104 | 0.0728 | 0.027012987 | 0.494229464 |
| 106 | 0.1037 | 0.038478664 | 0.704005431 |
| Test II | | | |
| Abatacept | 3.754 | 1 | — |
| Belatacept | 0.2433 | — | 1 |
| 104 | 0.1169 | 0.031140117 | 0.480476778 |
| 107 | 0.1406 | 0.037453383 | 0.577887382 |
| 112 | 0.6951 | 0.185162493 | 2.856966708 |
| 118 | 0.4145 | 0.110415557 | 1.703658035 |
| 122 | 0.3995 | 0.106419819 | 1.642005754 |
| 131 | 0.0825 | 0.021976558 | 0.339087546 |
| Test III | | | |
| Abatacept | 1.835 | 1 | — |
| Belatacept | 0.1298 | — | 1 |
| 82 | 0.1923 | 0.10479564 | 1.481510015 |
| 104 | 0.08385 | 0.045694823 | 0.645993837 |
| 131 | 0.05936 | 0.032348774 | 0.457318952 |
| 132 | 0.09888 | 0.053885559 | 0.761787365 |
| 133 | 0.0264 | 0.014386921 | 0.203389831 |
| 134 | 0.04938 | 0.026910082 | 0.380431433 |
| 142 | 0.01885 | 0.01027248 | 0.145223421 |
| Test IV | | | |
| Abatacept | 1.03 | 1 | — |
| Belatacept | 0.04691 | — | 1 |
| 142 | 0.009715 | 0.009432039 | 0.2070987 |

Exemplary polypeptides that were tested in the Examples 1-6 are polypeptides that comprise the mutations listed in Table 5 with respective to SEQ ID NO: 2.

TABLE 5

| Mutations of Exemplary Polypeptides | |
|---|---|
| Variant # | Mutations |
| 71 | G27DKA |
| 72 | R33W |
| 73 | G68F |
| 74 | G27DKA R33W |
| 75 | G27DKA G68F |
| 76 | R33W G68F |
| 77 | T51N, L61E, K93Q |
| 78 | T51N, M53Y |
| 80 | A29H, T51N |
| 81 | A29Y R33W |
| 82 | A29H, T51N, L61E, K93Q |
| 83 | T51N, M53Y, L61E |
| 84 | G27DK |
| 85 | G27K |
| 86 | G27R |
| 87 | G27W |
| 88 | G27Y |
| 89 | G27H |
| 90 | G27R G68Y |
| 91 | G68K |
| 92 | G68W |
| 93 | G68Y |
| 94 | G68H |
| 95 | G27H G68F |
| 96 | G27DK G68F |
| 97 | G27DK G68D |
| 98 | G27DK G68E |
| 99 | G27D G68F |
| 100 | G27E G68F |
| 101 | G27H G68D |
| 102 | G27H G68E |
| 104 (75#) | G27DKA G68F |
| 105 (79#) | A29Y L104E |
| 106 (95#) | G27H G68F |
| 107 (96#) | G27DK G68F |
| 108 | A29T |
| 109 | A29S |
| 110 | G27DKA G68F D122H |
| 111 | G27DKA G68F A40T D122H |
| 112 | G27DKA G68F A40T P117S |
| 113 | G27DKA G68F L77V |
| 114 | G27DKA G68F C92S K93M |
| 115 | G27DK G68F A49P A50T |
| 116 | G27DK G68F A40T D86N G105S |
| 117 | G27KK G68F |
| 118 | G27DKA G68F P117S |
| 119 | G27DKA G68F A49P A50T |
| 120 | G27DK G68F A40T |
| 121 | G27DK G68F L77V G105S P117S |
| 122 | G27DK G68F L77V |
| 123 | G27DK G68F C92S K93M |
| 124 | G27DK G68F P117S |
| 125 | G27DKA G68F G105S |
| 126 | G27DKA G68F D86N |
| 127 | G27DK G68F D122H |
| 128 | G27DK G68F A40T G105S |
| 129 | G27DKG68F G105S |
| 130 | G27DK G68F D86N |
| 131 | G27DKA G68F A40T |
| 132 | A24E, G27H, T30N, V32I, D41N, A50M, M54K, N56D, S64P, I65S, S70F, M85A, I106F |
| 133 | G27DKA G68F K93M |
| 134 | G27DK G68F K93M |
| 135 | K93V |
| 136 | K93M |
| 137 | K93W |
| 138 | K93P |
| 139 | K93C |
| 140 | K93F |
| 141 | K93R |
| 142 | G27DKA A40T G68F K93M |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

TABLE 6

Fc Sequences

| Seq ID No: | SEQUENCE |
|---|---|
| 7 | DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 8 | DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 9 | DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSP |
| 10 | DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 11 | DKTHTCPPCP APEAEGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPS SIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 12 | EPKSSDKTHT CPPCPAPEAE GAPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPSSIEKT ISKAKGQPRE PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 13 | DKTHTCPPCP APELLGGPSV FLFPPKPKDT LMISRTPEVT CVVVDVSHED PEVKFNWYVD GVEVHNAKTK PREEQYGSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 14 | DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 15 | DKTHTCPPCP APELLGGPSV FLFPPKPKDT LMISRTPEVT CVVVDVSHED PEVKFNWYVD GVEVHNAKTK PREEQYQSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 16 | DKTHTCPPCP APELLGGPSV FLFPPKPKDT LMISRTPEVT CVVVDVSHED PEVKFNWYVD GVEVHNAKTK PREEQYSSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 17 | DKTHTCPPCP APELLGGPSV FLFPPKPKDT LMISRTPEVT CVVVDVSHED PEVKFNWYVD GVEVHNAKTK PREEQYASTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 18 | DKTHTCPPCP APELLGGPSV FLFPPKPKDT LMISRTPEVT CVVVDVSHED PEVKFNWYVD GVEVHNAKTK PREEQYHSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 19 | DKRVESKYGP PCPSCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPS QEEMTKNQVS |

TABLE 6-continued

| Seq ID No: | SEQUENCE |
|---|---|
| | LTCLVKGFYP SDIAVEWESN GQPENNYKTT PPVLDSDGSF FLYSRLTVDK SRWQEGNVFS CSVMHEALHN HYTQKSLSLS LGK |
| 20 | DKRVESKYGP PCPPCPAPEF LGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPS QEEMTKNQVS LTCLVKGFYP SDIAVEWESN GQPENNYKTT PPVLDSDGSF FLYSRLTVDK SRWQEGNVFS CSVMHEALHN HYTQKSLSLS LGK |

Fc Sequences

TABLE 7

Linker Sequences

| Seq ID No: | SEQUENCE |
|---|---|
| 21 | GAGGGGSG |
| 22 | EPKSSD |
| 23 | ESPKAQASSV PTAQPQAEGL A |
| 24 | ELQLEESAAE AQDGELD |
| 25 | GQPDEPGGS |
| 26 | GGSGSGSGSG SGS |
| 27 | ELQLEESAAE AQEGELE |
| 28 | GSGSG |
| 29 | GSGC |
| 30 | AGGGGSG |
| 31 | GSGS |
| 32 | QPDEPGGS |
| 33 | GSGSGS |
| 34 | TVAAPS |
| 35 | KAGGGGSG |
| 36 | KGSGSGSGSG SGS |
| 37 | KQPDEPGGS |
| 38 | KELQLEESAA EAQDGELD |
| 39 | KTVAAPS |
| 40 | KAGGGGSGG |
| 41 | KGSGSGSGSG SGSG |
| 42 | KQPDEPGGSG |
| 43 | KELQLEESAA EAQDGELDG |
| 44 | KTVAAPSG A GGGGSGG |
| 45 | AGGGGSG |
| 46 | GSGSGSGSGS GSG |
| 47 | QPDEPGGSG |
| 48 | TVAAPSG |

TABLE 7-continued

Linker Sequences

| Seq ID No: | SEQUENCE |
|---|---|
| 49 | GGGGSGGGSG GGGGSGGGSG GGGSGGGS |
| 50 | PSPEPPTPEP PSPEP |
| 51 | ELQLEESAAE AQEGELE |
| 52 | SSGGGGSGGG SGGGGGS |
| 53 | GS |
| 54 | GGGGS |
| 55 | EEEEDEEEED |
| 56 | PSPEPPTPEP |
| 57 | GSHHHHHHHH GS |
| 58 | GGGGSGGGGS GGGGS |
| 59 | GGGGGSGGGS GGGGS |
| 60 | GSGSGSGSGS GSGSGS |
| 61 | PSTPPTPSPS TPPTPSPS |
| 62 | RGGEEKKKEK EKEEQEERET KTP |
| 63 | GGGGSGGGGS GGGGSGGGGS GGGGS |
| 64 | PSPEPPTPEP PSPEPPTPEP PSPEPPTPEP |
| 65 | PSTPPTPSPS TPPTPSPSPS TPPTPSPSTP PTPSPS |
| 66 | PSPEP |
| 67 | PSPEPPTPEP PSPEPPTPEP |
| 68 | PSPEPPTPEP PSPEPPTPEP PSPEPPTPEP PSPEPPTPEP |
| 69 | PTPEPPSPEP PTPEPPSPEP |
| 70 | PSPEPGGGSP TPEP |
| 71 | PSPEPEEEDP TPEP |
| 72 | PSPEPPTPEP EEEDPSPEPP TPEP |
| 73 | PTPEPPSPEP PTPEPEEEDP SPEPPTPEPP SPEP |
| 74 | PTPEPPSPEP PTPEPGGGGS PSPEPPTPEP PSPEP |
| 75 | PSPEPTPEPS PEPPTPEPSP EPTPEP |

TABLE 7-continued

| Linker Sequences | |
|---|---|
| Seq ID No: | SEQUENCE |
| 76 | GETGS |
| 77 | GGGGSGGGGS |
| 78 | GETGSSGEGT |
| 79 | GETGSSGEGT GSTGS |
| 80 | GGGGSGGGGS GGGGSGGGGS |
| 81 | GETGSSGEGT GSTGSGAGES GTGESGEGGS |
| 82 | Q |

TABLE 8

| Sequence Listing | |
|---|---|
| Seq ID No: | SEQUENCE |
| 1 | MACLGFQRHK AQLNLATRTW PCTLLFFLLF IPVFCKAMHV AQPAVVLASS RGIASFVCEY ASPGKATEVR VTVLRQADSQ VTEVCAATYM MGNELTFLDD SICTGTSSGN QVNLTIQGLR AMDTGLYICK VELMYPPPYY LGIGNGTQIY VIDPEPCPDS DFLLWILAAV SSGLFFYSFL LTAVSLSKML KKRSPLTTGV YVKMPPTEPE CEKQFQPYFI PIN |
| 2 | MHVAQPAVVL ASSRGIASFV CEYASPGKAT EVRVTVLRQA DSQVTEVCAA TYMMGNELTF LDDSICTGTS SGNQVNLTIQ GLRAMDTGLY ICKVELMYPP PYYLGIGNGT QIYVIDPEPC PDSDQEPKSS DKTHTSPPSP APELLGGSSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 3 | MHVAQPAVVL ASSRGIASFV CEYASPGKYT EVRVTVLRQA DSQVTEVCAA TYMMGNELTF LDDSICTGTS SGNQVNLTIQ GLRAMDTGLY ICKVELMYPP PYYEGIGNGT QIYVIDPEPC PDSDQEPKSS DKTHTSPPSP APELLGGSSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 4 | MHVAQPAVVL ASSRGIASFV CEYASPGKYT EVWVTVLRQA DSQVTEVCAA TYMMGNELTF LDDSICTGTS SGNQVNLTIQ GLRAMDTGLY ICKVELMYPP PYYLGIGNGT QIYVIDPEPC PDSDQEPKSS DKTHTSPPSP APELLGGSSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 5 | MHVAQPAVVL ASSRGIASFV CEYESPHKAN EIRVTVLRQA NSQVTEVCAM TYMKGDELTF LDDPSCTGTF SGNQVNLTIQ GLRAADTGLY ICKVELMYPP PYYLGFGNGT QIYVIDPEPC PDSDQEPKSS DKTHTSPPSP APELLGGSSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 6 | MHVAQPAVVL ASSRGIASFV CEYASPDKAK ATEVRVTVLR QTDSQVTEVC AATYMMGNEL TFLDDSICTF TSSGNQVNLT IQGLRAMDTG LYICMVELMY PPPYYLGIGN GTQIYVIDPE PCPDSDQEPK SSDKTHTSPP SPAPELLGGS SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |

What is claimed is:

1. A polypeptide comprising a first amino acid sequence with about or greater than 70%, 75%, 80%, 85%, 90%, 95%, 96%, 97%, 98%, 99%, or 99.5% sequence identity to amino acids 1-124 of SEQ ID NO: 2, wherein the polypeptide comprises a mutation at position 68 with respect to SEQ ID NO: 2, wherein the polypeptide further comprises a second amino acid sequence fused to the first amino acid sequence, wherein the polypeptide exhibits enhanced binding affinity for CD80 and/or CD86 as compared to abatacept (SEQ ID NO: 2), as determined by surface plasmon resonance at 37° C.

2. The polypeptide of claim 1, comprising an amino acid substitution selected from the group consisting of: G68D, G68E, G68F, and G68Y with respect to SEQ ID NO: 2.

3. The polypeptide of claim 1, comprising a mutation at position 40 with respect to SEQ ID NO: 2.

4. The polypeptide of claim 1, wherein the polypeptide further comprises a mutation at one or more positions selected from positions 16, 24, 25, 27, 28, 29, 33, 41, 42, 48, 49, 50, 51, 52, 53, 54, 58, 59, 60, 61, 63, 64, 65, 69, 70, 80, 85, 93, 94, 96, and 10$^{5}$ with respect to SEQ ID NO: 2.

5. The polypeptide of claim 1, further comprising an amino acid substitution selected from the group consisting of: G27DKA, A40T, K93M, G27DK, G27H, and P117S, with respect to SEQ ID NO: 2.

6. The polypeptide of claim 1, further comprising at least one amino acid substitution selected from the group consisting of: A24E, G27H, G27D, A29S, R33W, D41G, T51N, K93M, K93N, and G10$^{5}$D, with respect to SEQ ID NO: 2.

7. The polypeptide of claim 1, comprising a combination of amino acid substitutions selected from the group consisting of: G27DKA/G68F, R33W/G68F, G27R/G68Y, G27H/G68F, G27DK/G68F, G27DK/G68D, G27DK/G68E, G27D/G68F, G27E/G68F, G27H/G68D, G27H/G68E, G27DKA/G68F, G27H/G68F, G27DK/G68F, G27DKA/G68F/D122H, G27DKA/G68F/A40T/D122H, G27DKA/G68F/A40T/P117S, G27DKA/G68F/L77V, G27DKA/G68F/C92S/K93M, G27DK/G68F/A49P/A50T, G27DK/G68F/A40T/D86N/G10$^{5}$S, G27KK/G68F, G27DKA/G68F/P117S, G27DKA/G68F/A49P/A50T, G27DK/G68F/A40T, G27DK/G68F/L77V/G10$^{5}$S/P117S, G27DK/G68F/L77V, G27DK/G68F/C92S/K93M, G27DK/G68F/P117S, G27DKA/G68F/G10$^{5}$S, G27DKA/G68F/D86N, G27DK/G68F/D122H, G27DK/G68F/A40T/G10$^{5}$S, G27DK/G68F/G10$^{5}$S, G27DK/G68F/D86N, G27DKA/G68F/A40T, G27DKA/G68F/K93M, G27DK/G68F/K93M, and G27DKA/A40T/G68F/K93M, with respect to SEQ ID NO: 2.

8. The polypeptide of claim 1, comprising a combination of amino acid substitutions G27DKA/A40T/G68F/K93M with respect to SEQ ID NO: 2.

9. The polypeptide of claim 1, comprising a combination of amino acid substitutions G27DKA/G68F/A40T with respect to SEQ ID NO: 2.

10. The polypeptide of claim 1, comprising a combination of amino acid substitutions G27DKA/G68F/K93M with respect to SEQ ID NO: 2.

11. The polypeptide of claim 1, comprising a combination of amino acid substitutions G27DKA/G68F with respect to SEQ ID NO: 2.

12. The polypeptide of claim 1, comprising a combination of amino acid substitutions G27DK/G68F/K93M with respect to SEQ ID NO: 2.

13. The polypeptide of claim 1, wherein the second amino acid sequence codes for an IgG Fc region.

14. The polypeptide of claim 13, wherein the IgG Fc region is from a human IgG molecule.

15. The polypeptide of claim 2, wherein the polypeptide has about or greater than 70%, 75%, 80%, 85%, 90%, 95%, 96%, 97%, 98%, 99%, 99.5% or 100% sequence identity to amino acids 1-359 of SEQ ID NO: 6.

16. A polypeptide-drug conjugate comprising the polypeptide of claim 1.

17. A method of treating a disease or condition comprising administering the polypeptide of claim 1 to a subject in need thereof.

18. A pharmaceutical composition comprising the polypeptide of claim 1 and a pharmaceutically acceptable excipient.

19. An isolated polynucleotide encoding the polypeptide of claim 1.

20. A vector comprising the isolated polynucleotide of claim 19.

21. A cell comprising the vector of claim 20.

* * * * *